US009611478B2

(12) United States Patent
Kelnar et al.

(10) Patent No.: US 9,611,478 B2
(45) Date of Patent: Apr. 4, 2017

(54) SYNTHETIC MIMICS OF MIR-124

(71) Applicant: Mirna Therapeutics, Inc., Austin, TX (US)

(72) Inventors: Kevin Kelnar, Kyle, TX (US); David Brown, Austin, TX (US)

(73) Assignee: MIRNA THERAPEUTICS, INC., Austin, TX (US)

( * ) Notice: Subject to any disclaimer, the term of this patent is extended or adjusted under 35 U.S.C. 154(b) by 0 days.

(21) Appl. No.: 14/938,350

(22) Filed: Nov. 11, 2015

(65) Prior Publication Data

US 2016/0060629 A1    Mar. 3, 2016

Related U.S. Application Data

(63) Continuation of application No. 13/365,646, filed on Feb. 3, 2012, now Pat. No. 9,222,085.

(60) Provisional application No. 61/439,272, filed on Feb. 3, 2011.

(51) Int. Cl.
| | |
|---|---|
| *A61K 48/00* | (2006.01) |
| *C07H 21/02* | (2006.01) |
| *C07H 21/04* | (2006.01) |
| *C12N 15/113* | (2010.01) |
| *A61K 31/713* | (2006.01) |
| *A61K 45/06* | (2006.01) |

(52) U.S. Cl.
CPC .......... *C12N 15/113* (2013.01); *A61K 31/713* (2013.01); *A61K 45/06* (2013.01); *C12N 2310/141* (2013.01); *C12N 2310/317* (2013.01); *C12N 2310/321* (2013.01)

(58) Field of Classification Search
CPC .............................. A61K 48/00; C12N 15/113
See application file for complete search history.

(56) References Cited

U.S. PATENT DOCUMENTS

| | | | |
|---|---|---|---|
| 5,998,203 A | 12/1999 | Matulic-Adamic et al. | |
| 7,056,704 B2 | 6/2006 | Tuschl et al. | |
| 7,078,196 B2 | 7/2006 | Tuschl et al. | |
| 7,232,806 B2 | 6/2007 | Tuschl et al. | |
| 7,365,058 B2 | 4/2008 | Stoffel et al. | |
| 7,683,036 B2 | 3/2010 | Esau et al. | |
| 7,723,030 B2 | 5/2010 | Croce et al. | |
| 7,723,510 B1 | 5/2010 | Tuschl et al. | |
| 7,772,389 B2 | 8/2010 | Tuschl et al. | |
| 7,960,359 B2 | 6/2011 | Brown et al. | |
| 8,058,250 B2 | 11/2011 | Brown et al. | |
| 8,071,562 B2 | 12/2011 | Bader et al. | |
| 8,137,910 B2 | 3/2012 | Cullen et al. | |
| 8,148,069 B2 | 4/2012 | Croce et al. | |
| 8,173,611 B2 | 5/2012 | Brown et al. | |
| 8,378,088 B2 | 2/2013 | Cleary et al. | |
| 8,563,708 B2 | 10/2013 | Brown et al. | |
| 8,586,727 B2 | 11/2013 | Kelnar et al. | |
| 8,729,036 B2 | 5/2014 | Zamore et al. | |
| 8,900,627 B2 | 12/2014 | Ford et al. | |
| 8,916,533 B2 | 12/2014 | Croce | |
| 8,946,177 B2 | 2/2015 | Brown et al. | |
| 9,222,085 B2 | 12/2015 | Kelnar et al. | |
| 2002/0086356 A1 | 7/2002 | Tuschl et al. | |
| 2003/0108923 A1 | 6/2003 | Tuschl et al. | |
| 2004/0175732 A1 | 9/2004 | Rana | |
| 2004/0259247 A1 | 12/2004 | Tuschl et al. | |
| 2005/0026278 A1 | 2/2005 | Tuschl et al. | |
| 2005/0075492 A1 | 4/2005 | Chen et al. | |
| 2005/0153337 A1 | 7/2005 | Manoharan | |
| 2005/0182005 A1 | 8/2005 | Tuschl et al. | |
| 2005/0234006 A1 | 10/2005 | Tuschl et al. | |
| 2005/0234007 A1 | 10/2005 | Tuschl et al. | |
| 2006/0105360 A1 | 5/2006 | Croce et al. | |
| 2007/0003960 A1 | 1/2007 | Tuschl et al. | |
| 2007/0003961 A1 | 1/2007 | Tuschl et al. | |
| 2007/0003962 A1 | 1/2007 | Tuschl et al. | |
| 2007/0003963 A1 | 1/2007 | Tuschl et al. | |
| 2007/0093445 A1 | 4/2007 | Tuschl et al. | |
| 2008/0132461 A1 | 6/2008 | Tuschl et al. | |
| 2008/0269147 A1 | 10/2008 | Tuschl et al. | |
| 2009/0186843 A1 | 7/2009 | Tuschl et al. | |
| 2011/0313025 A1 | 12/2011 | Brown et al. | |
| 2014/0107182 A1 | 4/2014 | Kelnar et al. | |
| 2014/0336370 A1 | 11/2014 | Esau et al. | |
| 2014/0348908 A1 | 11/2014 | Brown et al. | |
| 2015/0272981 A1 | 10/2015 | Bader et al. | |
| 2016/0053264 A1 | 2/2016 | Kelnar et al. | |

FOREIGN PATENT DOCUMENTS

| | | |
|---|---|---|
| CN | 102091333 A | 6/2011 |
| JP | 2008519606 A | 6/2008 |
| JP | 2011177139 A | 9/2011 |
| WO | WO-0244321 A2 | 6/2002 |
| WO | WO-03029459 A2 | 4/2003 |

(Continued)

OTHER PUBLICATIONS

Bader A. G. et al. The promise of microRNA replacement therapy. Cancer Res. vol. 70, pp. 7027-7030 (2010).
Bader A.G. et al. miR-34—a microRNA replacement therapy is headed to the clinic. Front Genet. vol. 3, p. 120 (2012).
Cao, X et al. A functional study of miR-124 in the developing neural tube. Genes & Development. (Mar. 1, 2007) 21( 5); 531-536.
Chui et al. siRNA function in RNAi: a chemical modification analysis. RNA 9: 1034-1048, 2003.
Conaco, C. et al. Reciprocal actions of REST and a microRNA promote neuronal identity. PNAS, Feb. 14, 2006, vol. 103, No. 7, pp. 2422-2427.

(Continued)

*Primary Examiner* — Amy Bowman
(74) *Attorney, Agent, or Firm* — Wilson Sonsini Goodrich & Rosati

(57) ABSTRACT

Embodiments concern methods and compositions involving miR-124 mimics. In some embodiments, there are double-stranded RNA molecules with modified nucleotides having an active strand with a miR-124 sequence and a complementary passenger strand.

24 Claims, No Drawings

(56) References Cited

FOREIGN PATENT DOCUMENTS

| WO | WO-2004066183 A2 | 8/2004 |
|---|---|---|
| WO | WO-2004074509 A2 | 9/2004 |
| WO | WO-2005013901 A2 | 2/2005 |
| WO | WO-2005079397 A2 | 9/2005 |
| WO | WO-2006128245 A1 | 12/2006 |
| WO | WO-2006137941 A2 | 12/2006 |
| WO | WO-2007081720 A2 | 7/2007 |
| WO | WO-2007081740 A2 | 7/2007 |
| WO | WO-2010056737 A2 | 5/2010 |
| WO | WO-2010151755 A2 | 12/2010 |
| WO | WO-2012041959 A1 | 4/2012 |
| WO | WO-2012106591 A1 | 8/2012 |
| WO | WO-2015153757 A1 | 10/2015 |

OTHER PUBLICATIONS

Furuta, M. et al. miR-124 and miR-203 are epigenetically silenced tumor-suppressive microRNAs in hepatocellular carcinoma. Carcinogenesis May 2010; 31 (5); 766-776 doi: 10.1093/carcin/bgp250. Epub Oct. 20, 2009.
International Application No. PCT/US2008/085178 International Search Report and Written Opinion Mailed Aug. 21, 2009.
International Application No. PCT/US2009/064015 International Search Report and Written Opinion Mailed Jul. 26, 2010.
International Application No. PCT/US2012/023755 International Search Report Mailed Apr. 12, 2012.
International Application No. PCT/US2015/023878 International Search Report and Written Opinion Mailed Jul. 10, 2015.
International Preliminary Report on Patentability and Written Opinion for International Application No. PCT/US2008/085178Mailed Jun. 10, 2010.
Karginov, F. et al. A biochemical approach to identifying microRNA targets. PNAS, Dec. 4, 2007, vol. 104, No. 49, pp. 19291-19296.
Lagos-Quintana et al. Identification of Tissue-Specific MicroRNAs from Mouse. Curr. Biol., Curr. Science, vol. 12, No. 9, Apr. 2002; 735-739.
Lim et al. Microarray analysis shows that some microRNAs downregulate large numbers of target mRNAs, Nature, 433(7027):769-773, 2005.
Lujambio et al. Genetic unmasking of an epigenetically silenced microRNA in human cancer cells, Cancer Research, 67(4):1424-1429, 2007.
Makeyev et al. The microRNA miR-124 promotes neuronal differentiation by triggering brain-specific alternative pre-mRNA splicing, Molecular Cell, 27(3):435-448, 2007.
Shelton et al. MicroRNAs and Human Cancer, Abstract submitted for a Cold Spring Symposium in early Jun. 2006—71st Symposium: Regulatory RNAs.
Silber et al. miR-124 and miR-137 inhibit proliferation of glioblastoma multiforme cells and induce differentiation of brain tumor stem cells. BMC Med. Jun. 24, 2008;6:14. doi: 10.1186/1741-7015-6-14.
U.S. Appl. No. 11/273,640 Office Action Mailed May 5, 2010.
U.S. Appl. No. 11/273,640 Office Action Mailed Nov. 20, 2009.
U.S. Appl. No. 11/837,487 Office Action Mailed May 28, 2010.
U.S. Appl. No. 11/837,487 Office Action Mailed Sep. 15, 2009.
U.S. Appl. No. 12/325,917 Office Action Mailed Apr. 22, 2011.
U.S. Appl. No. 12/325,917 Office Action Mailed Feb. 14, 2011.
U.S. Appl. No. 12/325,917 Office Action Mailed Jul. 28, 2010.
U.S. Appl. No. 13/365,646 Office Action Mailed Apr. 17, 2013.
U.S. Appl. No. 13/365,646 Office Action Mailed Dec. 26, 2013.
U.S. Appl. No. 13/365,646 Office Action Mailed Feb. 4, 2015.
U.S. Appl. No. 13/365,676 Office Action Mailed Mar. 19, 2013.
U.S. Appl. No. 13/887,008 Office Action Mailed Sep. 18, 2013.
U.S. Appl. No. 14/012,302 Office Action Mailed Nov. 26, 2013.
U.S. Appl. No. 14/081,295 Office Action Mailed Nov. 6, 2014.
U.S. Appl. No. 14/459,192 Office Action Mailed Mar. 10, 2015.
U.S. Appl. No. 14/459,192 Office Action Mailed Sep. 16, 2015.
U.S. Appl. No. 14/704,458 Third Party Submission Mailed Jan. 29, 2016.
U.S. Appl. No. 14/738,646 Office Action Mailed Oct. 6, 2015.
U.S. Appl. No. 11/273,640 Office Action Mailed Jul. 26, 2011.
Visvanathan, J. et al. The microRNA miR-124 antagonizes the anti-neural REST/SCP1 pathway during embryonic CNS development. Genes & Development. Apr. 1, 2007, vol. 21, No. 7, pp. 744-749.
Volinia et al. A microRNA expression signature of human solid tumors defines cance gene targets. PNAS USA 103(7):2257-2261 (2006).
Wang, X. et al. Systematic identification of microRNA functions by combining target prediction and expression profiling; Nucleic acids research. 2006, vol. 34, No. 5, pp. 1646-1652.
Weidhaas et al. MicroRNAs as potential agents to alter resistance to cytotoxic anticancer therapy, Cancer Res, 67(23):11111-11116, (2007).
Co-Pending U.S. Appl. No. 14/676,308, filed Apr. 1, 2015.
Khvorava, et al. Functional siRNAs and miRNAs exhibit strand bias. Cell, 2003, vol. 115, p. 209-216.
Sempere, LF, et al. Expression profiling of mammalian microRNAs uncovers a subset of brain-expressed microRNAs with possible roles in murine and human neuronal differentiation. Genome Biology 2004, 5:R13 (Feb. 16, 2004).
U.S. Appl. No. 13/602,933 Office Action Mailed Nov. 7, 2014.
U.S. Appl. No. 14/215,669 Office Action Mailed Jul. 20, 2016.
U.S. Appl. No. 14/459,192 Final Office Action Mailed Apr. 26, 2016.
U.S. Appl. No. 14/736,177 Office Action Mailed Jul. 19, 2016.

SYNTHETIC MIMICS OF MIR-124

CROSS-REFERENCE TO RELATED APPLICATIONS

This application is a continuation of U.S. patent application Ser. No. 13/365,646, filed Feb. 3, 2012, now issued as U.S. Pat. No. 9,222,085, which claims priority to U.S. Provisional Patent Application No. 61/439,272 filed on Feb. 3, 2011, both of which are hereby incorporated by reference in their entireties.

SEQUENCE LISTING

The present application contains a Sequence Listing which has been submitted in ASCII format via EFS-Web and is hereby incorporated by reference in its entirety. Said ASCII copy, created Nov. 9, 2015, is named "48436712301.txt" and is 47,180 bytes in size.

BACKGROUND OF THE INVENTION

I. Field of the Invention

The present invention relates to the fields of molecular biology and medicine. More specifically, there are methods and compositions involving RNA molecules with at least the functional properties of miR-124 and in some embodiments, enhanced characteristics related to miR-124 for the treatment of diseases and/or conditions.

II. Background

In 2001, several groups used a cloning method to isolate and identify a large group of "microRNAs" (miRNAs) from *C. elegans, Drosophila*, and humans (Lau et al., 2001; Lee and Ambros, 2001; Lagos-Quintana et al., 2003).

Published human mature microRNA sequences, described in the database miRBase 15.0 (Griffths-Jones et al., 2006), range in size from 16-27 nucleotides in length and arise from longer precursors. The precursors form structures that fold back on themselves in self-complementary regions and are processed by the nuclease Dicer (in animals) or DCL1 (in plants) to generate the short double-stranded mature miRNA. One of the mature miRNA strands is incorporated into a complex of proteins and miRNA called the RNA-induced silencing complex (RISC). The miRNA guides the RISC complex to a target mRNA, which is then cleaved or translationally silenced, depending on the degree of sequence complementarity of the miRNA to its target mRNA. Currently, it is believed that perfect or nearly perfect complementarity leads to mRNA degradation, as is most commonly observed in plants. In contrast, imperfect base pairing, as is primarily found in animals, leads to translational silencing. However, recent data suggest additional complexity (Bagga et al., 2005; Lim et al., 2005), and mechanisms of gene silencing by miRNAs remain under intense study.

Studies have shown that changes in the expression levels of numerous miRNAs are associated with various cancers (reviewed in Calin and Croce, 2006; Esquela-Kerscher and Slack, 2006; Wiemer, 2007). miRNAs have also been implicated in regulating cell growth and cell and tissue differentiation—cellular processes that associated with the development of cancer.

The activity of a variety of miRNAs has been identified and analyzed. Although effective miRNA mimics have been identified previously in U.S. Patent Application Publication 20080050744, which is hereby incorporated by reference, there is a need for miRNA mimics that greatly improve one or more properties of the naturally occurring miRNA, particularly as these molecules move from the laboratory to the clinic.

SUMMARY OF THE INVENTION

Therapeutic microRNAs should be stable, active, and specifically hybridize with the correct mRNA target. Embodiments concern miR-124 mimics that have maintained and/or enhanced resistance to nuclease digestion, hybridization capability with the correct target mRNAs, and/or functionality.

Embodiments concern different RNA molecules containing the sequence of a mature miR-124. RNA molecules may be double-stranded and/or blunt-ended, which means the molecule is double-stranded throughout the molecule and blunt-ended on both ends. Moreover, embodiments concern chemical modifications of such RNA molecules to yield miR-124 mimics with improved or enhanced properties. The active strand of a double stranded RNA molecule contains a mature miR-124 sequence. In certain embodiments, the sequence of one strand of a double stranded RNA molecule consists of the sequence of a mature miR-124 sequence.

In some embodiments there is an RNA molecule that is double-stranded, meaning the molecule is composed of two polynucleotides or strands that can be separated from one another. A double-stranded molecule does not include a hairpin molecule, which is one strand or polynucleotide. In some embodiments, the RNA molecule is blunt-ended on one or both ends. In a double-stranded RNA molecule, one or both strands may be 18, 19, 20, 21, 22, 23, 24, or 25 nucleotides in length, or any range derivable therein. In certain embodiments, a double-stranded, blunt-ended molecule is 20, 21, or 22 basepairs (bps) in length.

It is contemplated that in some embodiments a double-stranded RNA molecule contains two strands that are fully complementary to one another, which results in a molecule that is necessarily blunt-ended.

In certain embodiments, an RNA molecule has an active strand comprising a mature human miR-124 sequence (5'-UAAGGCACGCGGUGAAUGCC-3') (SEQ ID NO:1) (20-mer). In certain embodiments, the mature miR-124 sequence has the sequence of SEQ ID NO:1 and an additional U at the 5' end and an extra A at the 3' end (5'-UUAAGGCACGCG-GUGAAUGCCA-3') (SEQ ID NO:2) (22-mer). Thus, in certain embodiments, an RNA molecule has an active strand with the sequence of nucleotides 2 through 21 of SEQ ID NO:2. In additional embodiments, an RNA molecule has an active strand with the sequence of nucleotides 2 through 21 of SEQ ID NO:2, but is 21 or 22 nucleotides in length because 1) at the 5' end there is an additional nucleotide selected from the group consisting of A, C, G, and U and/or 2) at the 3' end there is an additional nucleotide selected from the group consisting of A, C, G, U. Thus, an RNA molecule with an active stand having the sequence of SEQ ID NO:2 is specifically contemplated in the embodiment discussed in the previous sentence. In some embodiments, the active strand has a modified nucleotide at one or more internal positions.

By convention, sequences discussed herein are set forth 5' to 3' unless other specified. Moreover, a strand containing the sequence of a SEQ ID NO has that sequence from 5' to 3' unless otherwise specified.

The term "internal positions" refers to a position that is neither the first nor last position in the strand. The term "modified nucleotide" means a nucleotide or nucleoside (if referring to the nucleobase at the 5' position) with an additional moiety or a replacement moiety compared to an unmodified nucleotide. With active strands containing one or more modified nucleotides, it is contemplated that there are, there are no fewer than, or there are no more than 2, 3, 4, 5, 6, 7, 8, 9, 10, 11, 12, 13, 14, or 15 modified nucleotides, or any range derivable therein. It is specifically contemplated that in some embodiments, fewer than every nucleotide in the active strand is modified, and that fewer than half of the nucleotides in the active strand are modified. Moreover, in some embodiments, it is specifically contemplated that an active strand having multiple modified nucleotides does not have every other nucleotide in the active strand is modified. The miRNA mimics disclosed herein are sequence- and position-specific.

In some embodiments, the active strand comprises at least two modified nucleotides. In additional embodiments, the active strand does not have a modified nucleotide in the first two positions at either end. In further embodiments, the active strand does not comprise a modified nucleotide in the first four positions from the 5' end.

In some embodiments, an active strand may comprise a mature miR-124 sequence of SEQ ID NO:1 (5'-UAAGGCACGCGGUGAAUGCC-3') or comprise the sequence of nucleotides 2 through 21 of SEQ ID NO:2 (5'-UUAAGGCACGCGGUGAAUGCCA-3'). SEQ ID NO:2 has the mature miR-124 sequence of SEQ ID NO:1 in conjunction with an additional U at the 5' end and an extra A at the 3' end. In either of these embodiments, the active strand comprises the same sequence. In additional embodiments, an active strand has a sequence that comprises or consists of SEQ ID NO:2. In some embodiments, an active strand may have modified nucleotides in which the identity of those modified nucleotides is relative to the SEQ ID NO: being referred to.

In specific embodiments, the modified nucleotides in the active strand are the nucleotides located at positions 5 (G), 6 (G), 7 (C), 8 (A), 11 (C), 12 (G), 17 (A), 18 (U), 19 (G), and/or 20 (C) relative to SEQ ID NO:2. This means they are the nucleotides corresponding to those nucleotides in the recited position in the recited SEQ ID NO. Moreover, these recited nucleotides are situated at positions 4 (G), 5 (G), 6 (C), 7 (A), 10 (C), 11 (G), 16 (A), 17 (U), 18 (G), and/or 19 (C), respectively, in SEQ ID NO: 1. In other embodiments, an active strand has a modified nucleotide located at the following positions: 4, 5, 6, 7, 8, 10, 11, 12, 16, 17, 18, 19, and/or 20 in the active strand.

An active strand comprising the sequence of nucleotides 2 through 21 of SEQ ID NO:2 and having a modified nucleotide at position 5 relative to SEQ ID NO:2 means the first G in the sequence of 2-21 of SEQ ID NO:2 is modified. In other words, unless otherwise specified, modified nucleotides in the context of a SEQ ID NO are nucleotide-specific. With a 22-base active strand comprising SEQ ID NO:2 (22 residues in length), the positions of the modified nucleotides relative to SEQ ID NO:2 constitute the same recited positions in the 22-base active strand because the 22-base active strand has the same sequence as SEQ ID NO:2. Under these circumstances, the modified nucleotides in the active strand are the nucleotides located at positions 5 (G), 6 (G), 7 (C), 8 (A), 11 (C), 12 (G), 17 (A), 18 (U), 19 (G), and/or 20 (C) in SEQ ID NO:2.

Thus, in certain embodiments, an RNA molecule has an active strand having the sequence of nucleotides 2 through 21 of SEQ ID NO:2. In some embodiments, the active strand has a modified nucleotide at one or more internal positions. In additional embodiments, the active strand comprises at least two modified nucleotides located at positions 5 (G), 6 (G), 7 (C), 8 (A), 11 (C), 12 (G), 17 (A), 18 (U), 19 (G), and/or 20 (C) relative to SEQ ID NO:2. In further embodiments, there are at least 3, 4, 5, 6, 7, 8, 9, or 10 modified nucleotides (or any range derivable therein) located at positions 5 (G), 6 (G), 7 (C), 8 (A), 11 (C), 12 (G), 17 (A), 18 (U), 19 (G), and/or 20 (C) relative to SEQ ID NO:2.

When the particular nucleotide base is designated (as an "A," "C," "G," or "U") and is described as "relative" to a position in a sequence (such as a SEQ ID NO:2), this means that the modification of that particular designated nucleotide is contemplated in the strand even if its position changes by 1 or 2 positions (±1 or ±2 positions) (because of a deletion or insertion with respect to the reference sequence). In other embodiments, a modified nucleotide is described with respect to position in the strand and not as relative to a particular SEQ ID NO:2; in that case, position refers to the position in the strand, where the 5' end of the strand begins with position 1 and continues through 2, 3, 4, etc. until the nucleotide position at the 3' end is reached.

In certain embodiments, the active strand comprises no more than six modified nucleotides.

In other embodiments, the active strand has a modified nucleotide at one or more of the following positions 1 (U), 2 (U), 3 (A), 4 (A), 9 (C), 10 (G), 11 (C), 12 (G), 13 (G), 14 (U), 15 (G), 16 (A), 21 (C), and/or 22 (A) relative to SEQ ID NO:2. In other embodiments, the active strand has a modified nucleotide at position 1, 2, 3, 4, 8, 9, 10, 12, 13, 14, 15, 16, 20, 21, and/or 22 in the active strand. These may be instead of or in addition to modifications at other positions discussed herein.

In some embodiments, the active strand comprises a modified nucleotide at positions 7 (C) and 8 (A) relative to SEQ ID NO:2. In additional embodiments, the active strand further comprises a modified nucleotide at positions 17 (A) and 18 (U) relative to SEQ ID NO:2 or a modified nucleotide at positions 9 (C), 10 (G), 11 (C), and 12 (G) relative to SEQ ID NO:2. In other embodiments, the active strand has a modified nucleotide at position 8, 9, 10, 12, 16, 17, and/or 18 in the active strand. These may be instead or in addition to modifications at other positions discuss herein.

In some embodiments, RNA molecules that are double-stranded contain both an active strand comprising all of part of the sequence of a mature miRNA and a passenger strand fully or partially complementary to the active strand. In some embodiments, the passenger strand is, is at least, or is at most 80, 81, 82, 83, 84, 85, 86, 87, 88, 89, 90, 91, 92, 93, 94, 95, 96, 97, 98, 99, or 100% complementary, or any range derivable therein, to the active strand. In certain embodiments, the active and passenger strands are fully complementary to each other.

With passenger strands containing one or more modified nucleotides, it is contemplated that there are, there are no fewer than, or there are no more than 2, 3, 4, 5, 6, 7, 8, 9, 10, 11, 12, 13, 14, or 15 modified nucleotides, or any range derivable therein. It is specifically contemplated that in some embodiments, fewer than every nucleotide in the passenger strand is modified, and that fewer than half of the nucleotides in the passenger strand are modified in certain embodiments. Moreover, in some embodiments, it is specifically contemplated that a passenger strand having multiple modified nucleotides does not have every other nucleotide in the passenger strand modified.

In such embodiments, the passenger stand comprises a nucleotide modification at the 5' end, which may be referred to as a 5' terminal modification. Such a terminal modification may be with respect to the nucleotide (or nucleoside if it lacks a phosphate group) at the 5' end. This terminal modification is specifically contemplated in some embodiments to be a modification that is not a modification of a sugar molecule. It is specifically contemplated that this modification may be one of the following: NH$_2$, biotin, an amine group, a lower alkylamine group, NHCOCH$_3$, an acetyl group, 2'O-Me, DMTO, fluoroscein, a thiol, acridine, Spacer 18 (PEG) amidite (DMT-Hexa(ethylene glycol)), or any other group with this type of functionality. In specific embodiments, the 5' terminal modification on the passenger strand is a C6 amine linker. In further embodiments, the nucleotide at the 5' end of the passenger strand may have both a non-sugar modification and a sugar modification.

In some embodiments, a passenger strand contains at least one modified nucleotide in the first six nucleotides and/or the last six nucleotides with respect to the 5' end of the passenger strand. In other embodiments, the passenger strand has, has at least, or has at most 1, 2, 3, 4, 5, 6, 7, 8, 9, 10, 11, 12, 13, 14, 15 or more modified nucleotides, or any range derivable therein.

In certain embodiments, the passenger strand comprises a modified nucleotide located at positions 1 (U), 2 (G), 3 (G), 4 (C), 5 (A), 6 (U), 13 (C), 14 (G), 15 (U), 16 (G), 17 (C), 18 (C), 19 (U), 20 (U), 21 (A), and/or 22 (A) relative to SEQ ID NO:4 (5'-UGGCAUUCACCGCGUGCCUUAA-3'). SEQ ID NO:4 contains a sequence that is fully complementary to SEQ ID NO:2. SEQ ID NO:4t has an extra U at the 5' end and an extra A at the 3' end compared to the complement of the human miR-124 sequence in the miRBase 16.0 database (Griffths-Jones et al., 2006) (the mature miR-124 sequence is SEQ ID NO:1, and its complement is SEQ ID NO:3). The modified nucleotides relative to SEQ ID NO:4 (set forth above) correspond in SEQ ID NO:3 (5'-GGCAUUCACCGCGUGCCUUA-3') to those at positions 1 (G), 2 (G), 3 (C), 4 (A), 5 (U), 12 (C), 13 (G), 14 (U), 15 (G), 16 (C), 17 (C), 18 (U), 19 (U), and/or 20 (A).

In some embodiments, a passenger strand comprises a modified nucleotide as positions 1 (U) and 22 (A) relative to SEQ ID NO:4. In further embodiments, the passenger strand comprises a modified nucleotide as positions 2 (G) and 21 (A) relative to SEQ ID NO:4, which may be in addition to or instead of modifications at positions 1 (U) and 22 (A). In certain embodiments, the passenger strand comprises a modified nucleotide at positions 1 (U), 2 (G), 3 (G), 20 (U), 21 (A), and 22 (A) relative to SEQ ID NO:4. It is further contemplated that the passenger strand may comprise or further comprise a modified nucleotide at position 4 (C) relative to SEQ ID NO:4. In other embodiments, the passenger strand further comprises a modified nucleotide at positions 5 (A) and 6 (U) relative to SEQ ID NO:4 in addition to modified nucleotides at positions i) 1 (U) and 22 (A) and/or ii) 4 (C) relative to SEQ ID NO:4.

In certain embodiments, the passenger strand does not have a modified nucleotide located at positions 7 (U), 8 (C), 9 (A), 10 (C), 11 (C), or 12 (G) relative to SEQ ID NO:4, while in other embodiments, one or more positions relative to SEQ ID NO:4 are contemplated.

Combinations of a particular active strand and a particular passenger strand are contemplated. It is contemplated that any active strand described herein may be combined with any passenger strand described herein to form a double-stranded RNA molecule. In some embodiments, there is a passenger strand comprising modified nucleotides at positions 2 (G) and 21 (A) relative to SEQ ID NO:4 and an active strand comprising modified nucleotides at positions 7 (C) and 8 (A) relative to SEQ ID NO:2. In further embodiments, the passenger strand further comprises modified nucleotides at positions 1 (U) and 22 (A) in SEQ ID NO:4, which may be instead of or in addition to modifications at positions 3(G) and 20 (U) relative to SEQ ID NO:4. In additional embodiments, the active strand may further comprise modified nucleotides at positions 17 (A) and 18 (U) relative to SEQ ID NO:2.

In some embodiments, there is a double-stranded, blunt-ended RNA molecule with 1) an active strand with the sequence of SEQ ID NO:2 and modified nucleotides at positions 7 (C) and 8 (A), and optionally also at positions 9 (C), 10 (G), 11 (C), and 12 (G) and or positions 17 (A) and 18 (U) relative to SEQ ID NO:2; and 2) a passenger strand with a 5' terminal modification and nucleotide modifications in the first and last three nucleotides, and optionally nucleotide modifications also at position 4 (C), 5 (A), and/or 6 (U) relative to SEQ ID NO:4. In certain embodiments, this combination of active and passenger strands has a 5' terminal modification of the passenger strand in which the terminal modification is an alkyl amine such as a C6 amine linker, and the nucleotide modifications are on the sugar at the 2' position. In specific embodiments, the sugar modification is a 2'OMe.

In some embodiments, there is a double-stranded, blunt-ended RNA molecule of 20-22 basepairs in length comprising: a) an active strand comprising i) the sequence of nucleotides 2 through 21 of SEQ ID NO:2 and ii) a modified nucleotide at one or more internal positions, wherein the strand does not have a modified nucleotide at its 5' end and there are no more than 10 modified nucleotides; and, b) a separate passenger strand that is fully complementary to the active strand and comprises a 5' end nucleotide modification and at least one more modified nucleotide, wherein the nucleotides located at positions 7-19 relative to SEQ ID NO:2 are not modified. In specific embodiments, the active strand comprises the sequence of SEQ ID NO:2.

In further embodiments, there is a double-stranded RNA molecule of 20-22 basepairs in length, wherein the RNA molecule is blunt-ended at both ends, comprising an active strand having the sequence of nucleotides 2 through 21 of SEQ ID NO:2 and a separate and fully complementary passenger strand with a modified nucleotide at the 5' end, wherein the active strand comprises at least one modified internal nucleotide and wherein the double-stranded RNA molecule is more stable in the presence of a nuclease compared to a double-stranded, blunt-ended RNA molecule lacking any modification of an internal nucleotide.

In some embodiments, the RNA molecule has nucleotides that are modified with a sugar modification. In specific embodiments, the sugar modification is 2'-OMe.

Specific embodiments include pharmaceutical compositions containing one or more RNA molecules capable of acting as miRNA mimics, particularly in a human cell. In certain embodiments, the RNA molecules are comprised in a lipid formulation. In other embodiments, RNA molecules may be formulated with a liposome, polymer-based nanoparticle, cholesterol conjugate, cyclodextran complex, polyethylenimine polymer and/or a protein complex.

Methods for providing miR-124 activity to a cell are also set forth in embodiments. In some embodiments, there are methods for providing miR-124 activity to a cell comprising administering to the cell an effective amount of an RNA molecule having miR-124 activity. In some embodiments, the cell is a cancer cell. Such RNA molecules are discussed throughout this disclosure.

Other methods include a method for decreasing cell proliferation comprising administering to the cell an effective amount of a miR-124 RNA molecule, such as the double-stranded RNA molecules discussed herein. Additional embodiments include methods for inducing apoptosis in a cell comprising administering to the cell an effective amount of the RNA molecules. Other embodiments concern methods for treating cancer in a patient comprising administering to the patient a pharmaceutical composition comprising one or more of the RNA molecules that have miRNA function. Further embodiments concern methods of inhibiting progression through cell cycle by administering an effective amount of the one or more miR-124 mimics discussed herein. In some embodiments, methods further comprise administering to the patient an additional cancer therapy. In some embodiments, a patient has been tested for and/or diagnosed with cancer.

Other embodiments concern the use of RNA molecules for treating cancer cells, or their use in decreasing cell proliferation, inducing apoptosis or providing miR-124 function to a cell. It is specifically contemplated for use with human cells and human patients.

The compositions and methods for their use can "comprise," "consist essentially of," or "consist of" any of the molecules or steps disclosed throughout the specification. With respect to the transitional phase "consisting essentially of," and in one non-limiting aspect, a basic and novel characteristic of the compositions and methods disclosed in this specification includes the miRNA mimic activity.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

Embodiments are directed to compositions and methods relating to miRNAs, as well as use of miRNA mimics. Methods include preparing such mimics and using such mimics to provide miRNA activity or function to a cell. In certain embodiments, miRNA mimics are used for therapeutic, prognostic, and diagnostic applications, particularly those methods and compositions related to therapeutic applications for conditions or diseases in which miRNA activity or function is involved.

I. NUCLEIC ACIDS

Nucleic acids include the sequences or segments of sequence that are identical or complementary sequences to mature microRNA ("miRNA" or "miR") molecules. Mature miRNA molecules are generally 21 to 22 nucleotides in length, though lengths of 16 and up to 27 nucleotides have been reported. The miRNAs are each processed from a longer precursor RNA molecule ("precursor miRNA"). Precursor miRNAs are transcribed from non-protein-encoding genes. The precursor miRNAs have two regions of complementarity that enable them to form a stem-loop- or foldback-like structure, which is cleaved in animals by a ribonuclease III-like nuclease enzyme called Dicer. The processed miRNA is typically a portion of the stem.

The processed miRNA (also referred to as "mature miRNA") becomes part of a large complex to down-regulate a particular target gene. Examples of animal miRNAs include those that imperfectly basepair with the target, which halts translation (Olsen et al., 1999; Seggerson et al., 2002). siRNA molecules also are processed by Dicer, but from a long, double-stranded RNA molecule. siRNAs are not naturally found in animal cells, but they can direct the sequence-specific cleavage of an mRNA target through an RNA-induced silencing complex (RISC) (Denli et al., 2003).

A. miR-124

It was previously demonstrated that hsa-miR-124 is involved with the regulation of numerous cell activities that represent intervention points for cancer therapy and for therapy of other diseases and disorders (U.S. patent application Ser. No. 11/141,707 filed May 31, 2005 and Ser. No. 11/273,640 filed Nov. 14, 2005, each of which is incorporated herein by reference in its entirety). For example, cell proliferation, cell division, and cell survival are frequently altered in human cancers. Transfection of human lung carcinoma cells (A549) and human cervical cancer cells (HeLa) with synthetic hsa-miR-124 reduced viable cell numbers. In addition, the inventors showed that miR-124 significantly increased the capacity of two therapeutic compounds (TRAIL, an apoptosis pathway activator in cancer cells, and etoposide, a topoisomerase II inhibitor that activates the apoptosis pathway in cancer cells and normal cells) to induce cell death in A549 or HeLa cells. Overexpression of synthetic miR-124 in various cell lines decreased cell proliferation. In those studies, the inventors observed reduced proliferation of human breast cancer cells (BT549), normal human breast epithelial cells (MCF12A), human cervical cancer cells (HeLa), human prostate carcinoma cells (22RV1), human basal cell carcinoma cells (TE 354.T), normal human skin cells (TE 353.5 k), and human lung carcinoma cells (A549, CRL-5826, HTB-57). Overexpression of miR-124 in HeLa cells significantly reduced the number of cells in the G2/M phase of the cell cycle when compared to cells transfected with a negative control miRNA. The inventors previously demonstrated that hsa-miR-124 regulates the expression of many genes that function in intracellular signal transduction in response to mitotic or apoptotic stimuli (U.S. patent application Ser. No. 12/325, 971 filed Dec. 1, 2008, which is incorporated herein by reference in its entirety). Also, others have recently observed that epigenetic silencing of miR-124 in cancers cells modulates activity of the oncogene, CDK6 and the tumor suppressor gene, Rb (Lujambio et al., 2007).

Hsa-miR-124 affects intracellular signaling at various levels and controls the expression of secretory proteins, transmembrane growth factor receptors, and cytoplasmic signaling molecules. Secretory proteins include fibroblast growth factor 2 (FGF2), insulin growth factor binding protein 1 and 3 (IGFBP1, IGFBP3), transforming growth factor beta-2 (TGFB2), and the inflammatory chemokine interleukin 8 (U.S. patent application Ser. No. 12/325,971 filed Dec. 1, 2008). FGF-2 is a secretory protein with potent mitogenic and angiogenic activity that transmits its signal into cells via transmembrane receptors (FGFRs) composed of 2-3 extracellular immunoglobulin-like domains and an intracellular tyrosine kinase domain (Chandler et al., 1999). FGF-2 mRNAs levels are increased in renal, oral and non-small cell lung cancer cells (Chandler et al., 1999). Similarly, IL-8 is frequently upregulated in various cancers and correlates with tumor vascularization, metastasis and poor prognosis (Rosenkilde and Schwartz, 2004; Sparmann and Bar-Sagi, 2004). TGFB2 is the corresponding ligand to TGF-.beta. receptors (TGFBR), a class of receptors that may function as tumor suppressors (Massague et al., 2000).

Membrane-associated proteins regulated by hsa-miR-124 are platelet-derived growth factor receptor-like (PDGFRL; also referred to as PDGF receptor beta-like tumor suppressor, PRLTS) and the Ras association domain family protein 2 (RASSF2). (U.S. patent application Ser. No. 12/325,971 filed Dec. 1, 2008). RASSF2 is a tumor suppressor candidate that is frequently downregulated in lung tumor cell lines (Vos et al., 2003). RASSF2 interacts with K-Ras and promotes cell cycle arrest and apoptosis. PDGFRL also functions as a tumor suppressor that shows loss of function in a broad variety of cancers either by loss of heterozygosity (LOH) or mis-sense and frame-shift mutation (Fujiwara et al., 1995; Komiya et al., 1997). Since treatment of cancer cells with hsa-miR-124 leads to reduced expression levels of FGF2, IL8 and IGFBPs, and to increased expression levels of TGFB2, RASSF2 and PDGFRL, hsa-miR-124 is likely to induce a therapeutic response in cancer patients that show aberrant expression or function of these growth-stimulatory or inhibitory proteins (U.S. patent application Ser. No. 12/325,971 filed Dec. 1, 2008).

Intracellular signaling molecules regulated by hsa-miR-124 include IkappaB kinase alpha (IKKalpha, CHUK), c-Src (SRC), the catalytic subunit of class IA phosphoinositide 3-kinases p110.alpha. (PIK3CA) and phospholipase C beta-1 (PLCB1). PLC beta-1 catalyzes the generation of inositol-1,4,5-trisphosphate (IP3) and diacylglycerol (DAG) from phosphatidylinositol-bis-phosphate (PIP2), regulating proliferative signals and checkpoints of the cell cycle (Lo Vasco et al., 2004). (U.S. patent application Ser. No. 12/325, 971 filed Dec. 1, 2008). IKKalpha is a positive regulator of the intracellular signaling cascade and functions to activate the transcription factor nuclear factor kappa B (NFkappaB) (Karin et al., 2002). NFkappaB is constitutively activated in several cancer types and promotes anti-apoptotic and survival pathways. The proto-oncoprotein c-Src is the human homolog of avian v-Src that has been isolated as the tumorigenic component of Rous Sarcoma virus (RSV) (Rous, 1911; Stehelin et al., 1976; Yeatman, 2004). c-Src is a membrane-associated tyrosine kinase that is activated in response to intracellular signaling or indirectly to extracellular stimuli by binding to activated receptor tyrosine kinases, including EGFR, ERBB2, PDGFR and FGFR. Src is a crucial molecule in a complex network of interacting proteins, regulating cell adhesion, motility, invasion and proliferation. c-Src is frequently overexpressed or hyperactivated in numerous cancer types (Yeatman, 2004). The gene product of PIK3CA activates the Akt signaling pathway in response to most upstream receptor tyrosine kinases (Vanhaesebroeck et al., 1997). PIK3CA frequently acquires a gain of function in the vast majority of human cancers, either by amplification or overexpression, such as in ovarian and cervical cancers, or by activating somatic mutations (Bader and Vogt, 2004; Bader et al., 2005). PIK3CA has become a novel drug target in the pharmaceutical industry and is also a predicted target of hsa-miR-124. Based on the inventors previous data (U.S. patent application Ser. No. 12/325,971 filed Dec. 1, 2008, which is hereby incorporated by reference), hsa-miR-124 negatively regulates these proteins and therefore is likely to function as a tumor-suppressor miRNA.

Another class of genes and their corresponding proteins that are regulated by hsa-miR-124, functions in the progression of the cell cycle (U.S. patent application Ser. No. 12/325,971 filed Dec. 1, 2008). Some of these proteins are critical in the transition through G1 and S phases, such as cyclins A2 and E2 (CCNA2, CCNE2), cyclin dependent kinases 2, 4 and 6 (CDK2, CDK4, CDK6) and cell division cycle 6 (CDC6). Others are required for progressing through the G2/M spindle checkpoint and proper segregation of sister chromatids during mitosis to maintain chromosomal stability. These include aurora kinases A and B (AURKA, a.k.a. STK6; AURKB, a.k.a. STK12), breast cancer 1 and 2 (BRCA1; BRCA2), budding uninhibited by benzimidazoles 1 (BUB1), budding uninhibited by benzimidazoles 1 beta (BUB1B), polo-like kinase 1 (PLK1), cyclin dependent kinase 1 (CDK1, a.k.a. CDC2), cyclins B1 and B2 (CCNB1, CCNB2), and cell division cycle 20 and 23 (CDC20, CDC23, a.k.a. anaphase promoting complex subunit 8). Most of these transcripts are regulated in a manner that suggests that hsa-miR-124 blocks cell cycle progression.

Other molecules regulated by hsa-miR-124 that indirectly control cell cycle progression are SKP2, MDM2 and AKAP12 (U.S. patent application Ser. No. 12/325,971 filed Dec. 1, 2008). AKAP12, also referred to as gravin or SSeCKS (Src suppressed C kinase substrate), functions as a kinase scaffold protein that tethers the enzyme-substrate interaction (Nauert et al., 1997). Expression of AKAP12 interferes with oncogenic cell transformation induced by the Src or Jun oncoproteins in vitro and is lost or reduced in numerous cancers, such as leukemia and carcinomas of the rectum, lung and stomach (Lin and Gelman, 1997; Cohen et al., 2001; Xia et al., 2001; Wikman et al., 2002; Boultwood et al., 2004; Choi et al., 2004; Mori et al., 2006). An apparent anti-oncogenic activity of AKAP12 in prostate and gastric cancers marks this protein as a putative tumor suppressor (Xia et al., 2001; Choi et al., 2004). Skp2 is a component of the multi-subunit E3 ubiquitin ligase complex that ear-marks proteins for proteasomal degradation. A well characterized target is the CDK inhibitor p27 which offers an explanation for the cell cycle promoting activity of Skp2 (Carrano et al., 1999). Skp2 is inherently oncogenic and shows elevated levels in various cancer types (Gstaiger et al., 2001; Kamata et al., 2005; Saigusa et al., 2005; Einama et al., 2006).

Hsa-miR-124 also governs the expression of FAS, Bim (BCL2L11) and MCL1, all of which are functionally linked to the apoptotic pathway (U.S. patent application Ser. No. 12/325,971 filed Dec. 1, 2008).

miR-124 has been shown to have the following activities when provided to a cell: reduce cell viability, inhibit cell proliferation, decrease cell proliferation, and inhibit progression through cell cycle. These activities have been shown in diseased cells, such as cancer cells.

B. Oligomeric Compounds

Embodiments concern miRNA mimics, which contain molecules capable of mimicking the activity of an RNA molecule. An RNA molecule contains a nucleoside, which is a base-sugar combination. The base portion of the nucleoside is typically a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. It is contemplated that an RNA strand will be composed of nucleotides (ribonucleotides) and that the 5' end may be a nucleotide or a nucleoside. In other words, there may be a phosphate group linked to the sugar portion of the nucleoside or there may be only a hydroxyl group instead of the phosphate group. As discussed herein, in some embodiments, there is a modification of a terminal nucleoside or nucleotide in which a chemical moiety or group is attached to the sugar through what is, or was formerly, a hydroxyl or phosphate group.

In forming oligonucleotides, the phosphate groups covalently link adjacent nucleosides to one another to form a linear polymeric compound. The respective ends of this linear polymeric structure can be joined to form a circular structure by hybridization or by formation of a covalent bond. In addition, linear compounds may have internal nucleobase complementarity and may therefore fold in a manner as to produce a fully or partially double-stranded structure. Within the oligonucleotide structure, the phosphate groups are commonly referred to as forming the internucleoside linkages of the oligonucleotide. The normal internucleoside linkage of RNA and DNA is a 3' to 5' phosphodiester linkage.

In some embodiments, there is an RNA, RNA molecule, or RNA analog having a length of between 17 and 130 residues. Embodiments concern synthetic miRNA molecules that are, are at least, or are at most 15, 16, 17, 18, 19, 20, 21, 22, 23, 24, 25, 26, 27, 28, 29, 30, 31, 32, 33, 34, 35, 36, 37, 38, 39, or 40 or more residues in length, including any integer or any range derivable therein. Each strand or RNA molecule in a double-stranded RNA molecule may be such lengths as recited above. In some embodiments, an RNA molecule has a blunt end on one or both ends. In certain embodiments, the RNA molecule has a blunt end on the side having the 5' end of the active strand. In other embodiments, the RNA molecule has a blunt end on the side having the 5' end of the passenger strand. In certain embodiments RNA molecules described herein may have one or two strands. In molecules with two strands, the two strands may be hybridized to one another, but they are not connected to one another by an internucleoside linkage.

In certain embodiments, such RNA molecules that comprise or consist of SEQ ID NO:1 or SEQ ID NO:2 (or that consists of a sequence that has at least 90% identity with one of the recited SEQ ID Nos) have a modified nucleotide or nucleoside located at position 1, 2, 3, 4, 5, 6, 7, 8, 9, 10, 11, 12, 13, 14, 15, 16, 17, 18, 19, 20, and/or 21 in the active strand (position 1 is the 5' end). In further embodiments, a modified nucleotide or nucleoside is located at position 1, 2, 3, 4, 5, 6, 7, 8, 9, 10, 11, 12, 13, 14, 15, 16, 17, 18, 19, 20, and/or 21 in a passenger strand (position 1 is the 5' end) that comprises or consists of SEQ ID NO:3 or SEQ ID NO:4 (or that consists of a sequence that has at least 90% identity with one of the recited SEQ ID Nos). The designation of the modified nucleotide is position-specific, as opposed to nucleotide-specific. Accordingly, an embodiment in which nucleotide-specific modifications are discussed, for example, "a passenger strand comprising modified nucleotides at positions 2 (G) and 21 (A) relative to SEQ ID NO:4," may be implemented in other embodiments with respect to position; consequently, in further embodiments, an RNA molecule may comprise, for example, a passenger strand comprising a modified nucleotide at positions 2 and 21.

In some embodiments, the miRNA mimic or RNA molecule is not blunt-ended on both sides. It is contemplated that there may be a 1, 2, 3, 4, 5, or 6 base overhang on either the 3' or 5' end of the passenger or active strands of a double-stranded RNA mimic or molecule.

In some embodiments, the passenger strand and the active strand are not fully complementary. It is contemplated that there may be 1, 2, 3, 4, 5, 6 or more nucleotides between the two strands that are not complementary. In some embodiments, these nucleotides are within the first 10 nucleotides of the 5' end of the passenger strand.

It is contemplated that RNA mimics have RNA bases, which may or may not be modified. As such, RNA mimics are RNA or RNA molecules. Moreover, it is understood that a nucleic acid, including RNA, may have more than one-strand. As discussed herein, in some embodiments a miRNA mimic or RNA molecule is double-stranded. Unless otherwise specified, a double-stranded RNA molecule or miRNA mimic will be understood to have two strands that can be separated from each other and that are not simply connected to one another by a hairpin linker. A hairpin molecule has one strand that is capable of intramolecular hybridization. In some embodiments, the miRNA mimic is a hairpin molecule. In others, the miRNA mimic is a double-stranded RNA molecule.

In certain embodiments, therapeutic double-stranded nucleic acids have a first active strand with (a) a "miRNA region" whose sequence from 5' to 3' is identical to all or a segment of a mature miRNA sequence, and a second passenger strand having (b) a "complementary region" whose sequence from 5' to 3' is between 60% and 100% complementary to the miRNA sequence. In certain embodiments, these synthetic miRNA are also isolated, as defined below, or purified. The term "miRNA region" refers to a region on the synthetic miRNA that is at least 75, 80, 85, 90, 95, or 100% identical, including all integers there between, to the entire sequence of a mature, naturally occurring miRNA sequence. In certain embodiments, the miRNA region is or is at least 90, 91, 92, 93, 94, 95, 96, 97, 98, 99, 99.1, 99.2, 99.3, 99.4, 99.5, 99.6, 99.7, 99.8, 99.9 or 100% identical to the sequence of a naturally-occurring miRNA, such as the human miRNA sequence. Alternatively, the miRNA region can comprise 18, 19, 20, 21, 22, 23, 24 or more nucleotide positions in common with a naturally-occurring miRNA as compared by sequence alignment algorithms and methods well known in the art.

The term "complementary region" refers to a region of a synthetic miRNA that is or is at least 60% complementary to the mature, naturally occurring miRNA sequence that the miRNA region is identical to. The complementary region is or is at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein. With single polynucleotide sequences, there may be a hairpin loop structure as a result of chemical bonding between the miRNA region and the complementary region. In other embodiments, the complementary region is on a different nucleic acid strand than the miRNA region, in which case the complementary region is on the passenger strand and the miRNA region is on the active strand.

The term "oligonucleotide" is understood in the art to refer to an oligomer or polymer of ribonucleic acid (RNA) or deoxyribonucleic acid (DNA), typically one that is no more than 100 bases or base pairs in length. It is contemplated that an oligonucleotide may have a nucleoside at the 5' end. This term includes oligonucleotides composed of naturally occurring nucleobases, sugars and covalent internucleoside linkages. The term "oligonucleotide analog" refers to oligonucleotides that have one or more non-naturally occurring portions which function in a similar manner to oligonucleotides. Such non-naturally occurring oligonucleotides may have desirable properties compared to the naturally occurring oligonucleotides such as, for example, those disclosed herein, including, but not limited to, increased physiological activity, increased stability in the presence of a nuclease(s), and/or increased pharmacokinetic properties.

The term "oligonucleoside" refers to nucleosides that are chemically connected via internucleoside linkages that do not have phosphorus atoms. Internucleoside linkages include short chain alkyl, cycloalkyl, mixed heteroatom alkyl, mixed heteroatom cycloalkyl, one or more short chain heteroatomic and one or more short chain heterocyclic. These internucleoside linkages include, but are not limited to, siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and CH₂ component parts. In addition to the modifications described above, the nucleosides of the oligomeric compounds of the invention can have a variety of other modifications. Additional nucleosides amenable to embodiments having modified base moieties and or modified sugar moieties are disclosed in U.S. Pat. No. 6,383,808 and PCT application PCT/US89/02323, both of which are hereby incorporated by reference.

Altered base moieties or altered sugar moieties also include other modifications consistent with the purpose of an miRNA mimic. Such oligomeric compounds are best described as being structurally distinguishable from, yet functionally interchangeable with, naturally occurring or synthetic unmodified oligonucleotides. All such oligomeric compounds are comprehended by this invention so long as they function effectively to mimic the structure or function of a desired RNA or DNA oligonucleotide strand.

In some embodiments, RNA mimics include a base modification or substitution. The natural or unmodified bases in RNA are adenine (A) and guanine (G), and the pyrimidine bases cytosine (C) and uracil (U) (DNA has thymine (T)). In contrast, modified bases, also referred to as heterocyclic base moieties, include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (including 5-bromo, 5-trifluoromethyl and other 5-substituted uracils and cytosines), 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine.

One or more base or sugar modifications may be used to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA-like nucleosides so that particular properties of an oligomeric compound can be enhanced while maintaining the desired 3'-endo conformational geometry (see Scheme 1 of U.S. Patent Application Publication 2005/0261218, which is hereby incorporated by reference).

In some embodiments, an RNA mimic has a modification particularly of the 5' terminal residue of specifically the strand of an RNA mimic having the sequence that is complementary to the mature miRNA. This strand is referred to as the "passenger" strand herein. Without being bound to theory, it appears that the presence of a stable moiety other than a phosphate or hydroxyl at the 5' end of the complementary strand impairs or eliminates uptake of the passenger strand by the miRNA pathway complex and subsequently favors uptake of the active strand by the miRNA protein complex. 5' modifications include, but are not limited to, NH₂, biotin, an amine group, a lower alkylamine group, a lower alkyl group, NHCOCH₃, an acetyl group, 2' oxygen-methyl (2'O-Me), DMTO, fluoroscein, a thiol, or acridine or any other group with this type of functionality. In other embodiments, there is a Spacer 18 (PEG) amidite (DMT-Hexa(ethylene glycol)). In other embodiments, there is an alkylamine or alkyl group of 40 carbons or fewer. In embodiments involving a "lower" alkylamine or alkyl group, "lower" will be understood to refer to a molecule with 20 or fewer carbons.

In specific embodiments, there is a C4-C12 amine linker on the 5' end of the passenger strand. In specific embodiments, there is a C6 amine on the terminal phosphate of the first nucleotide of the passenger strand:

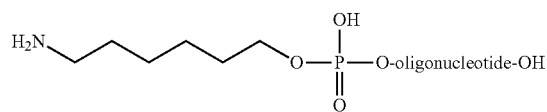

In specific embodiments, there is a C12 amine linker on the 5' end of the passenger strand. In other embodiments, there is a C8 amine linker on the terminal phosphate of the first nucleotide of the passenger strand.

In different miRNA mimics discussed herein, these RNA molecules can have nucleotides with sugar portions that correspond to naturally occurring sugars or modified sugars. Representative modified sugars include carbocyclic or acyclic sugars, sugars having substituent groups at one or more of their 2', 3' or 4' positions and sugars having substituents in place of one or more hydrogen atoms of the sugar. In certain embodiments, the sugar is modified by having a substituent group at the 2' position. In additional embodiments, the sugar is modified by having a substituent group at the 3' position. In other embodiments, the sugar is modified by having a substituent group at the 4' position. It is also contemplated that a sugar may have a modification at more than one of those positions, or that an RNA molecule may have one or more nucleotides with a sugar modification at one position and also one or more nucleotides with a sugar modification at a different position.

Sugar modifications contemplated in miRNA mimics include, but are not limited to, a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. In some embodiments, these groups may be chosen from: $O(CH_2)_xOCH_3$, $O((CH_2)_xO)_yCH_3$, $O(CH_2)_xNH_2$, $O(CH_2)_xCH_3$, $O(CH_2)_xONH_2$, and $O(CH_2)_xON((CH_2)_xCH_3)_2$, where x and y are from 1 to 10.

In some embodiments, miRNA mimics have a sugar substituent group selected from the following: C1 to $C_{10}$ lower alkyl, substituted lower alkyl, alkenyl, alkynyl, alkaryl, aralkyl, O-alkaryl or O-aralkyl, SH, $SCH_3$, Cl, Br, CN, OCN, $CF_3$, $OCF_3$, $SOCH_3$, $SO_2CH_3$, $ONO_2$, $NO_2$, $N_3$, $NH_2$, heterocycloalkyl, heterocycloalkaryl, amino alkylamino, polyalkylamino, substituted silyl, an RNA cleaving group, a reporter group, an intercalator, a group for improving the pharmacokinetic properties of a mimic, or a group for improving the pharmacodynamic properties of a mimic, and other substituents having similar properties. In one embodiment, the modification includes 2'-methoxyethoxy (2'-O—$CH_2CH_2OCH_3$, which is also known as 2'-O-(2-methoxyethyl) or 2'-MOE) (Martin et al., Helv. Chim. Acta, 78, 486-504, 1995), that is an alkoxyalkoxy group. Another modification includes 2'-dimethylaminooxyethoxy, that is, a $O(CH_2)_2ON(CH_3)_2$ group, also known as 2'-DMAOE and 2'-dimethylaminoethoxyethoxy (also known in the art as 2'-O-dimethyl-amino-ethoxy-ethyl or 2'-DMAEOE), that is, 2'-O—$CH_2$—O—$CH_2$—$N(CH_3)_2$.

Additional sugar substituent groups include allyl (—$CH_2$—CH=$CH_2$), —O-allyl (—O—$CH_2$—CH=$CH_2$), methoxy (—O—$CH_3$), aminopropoxy (—$OCH_2CH_2CH_2NH_2$), and fluoro (F). Sugar substituent groups on the 2' position (2'-) may be in the arabino (up) position or ribo (down) position. One 2'-arabino modification is 2'-F. Other similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics, for example, cyclobutyl moieties, in place of the pentofuranosyl sugar. Examples of U.S. patents that disclose the preparation of modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, which are herein incorporated by reference in its entirety.

Representative sugar substituent groups include groups described in U.S. Patent Application Publication 2005/0261218, which is hereby incorporated by reference. In particular embodiments, the sugar modification is a 2'O-Me modification, a 2'F modification, a 2'H modification, a 2'amino modification, a 4'thioribose modification or a phosphorothioate modification on the carboxy group linked to the carbon at position 6', or combinations thereof.

Additional modifications are disclosed in U.S. Patent Application Publication 2010/0267814, which is hereby incorporated by reference. While this reference discloses general modifications that might be made, it does not disclose what is set forth herein that modifications might be made in the context of a particular sequence at specific nucleotides and/or in specific and select positions.

In some embodiments, a therapeutic nucleic acid contains one or more design elements. These design elements include, but are not limited to: (i) a replacement group for the phosphate or hydroxyl of the nucleotide or nucleoside, respectively, at the 5' terminus of the complementary region; (ii) one or more sugar modifications in the first or last 1 to 6 residues of the complementary region; or, (iii) non-complementarity between one or more nucleotides in the last 1 to 5 residues at the 3' end of the complementary region and the corresponding nucleotides of the miRNA region.

In certain embodiments, a synthetic miRNA has a nucleotide at its 5' end of the complementary region in which the phosphate and/or hydroxyl group has been replaced with another chemical group (referred to as the "replacement design"). In some cases, the phosphate group is replaced or added onto with an additional moiety, while in others, the hydroxyl group has been replaced or added onto with an additional moiety, such as described above with the C6 amine linker. In particular embodiments, the moiety is biotin, an amine group, a lower alkylamine group, an acetyl group, 2'O-Me (2' oxygen-methyl), DMTO (4,4'-dimethoxytrityl with oxygen), fluorescein, a thiol, or acridine, though other moieties are well known to those of skill in the art and can be used as well.

In other embodiments of the invention, there is a synthetic miRNA in which one or more nucleotides in the last 1 to 5 residues at the 3' end of the complementary region are not complementary to the corresponding nucleotides of the miRNA region ("non-complementarity") (referred to as the "non-complementarity design"). The non-complementarity may be in the last 1, 2, 3, 4, and/or 5 residues of the complementary miRNA. In certain embodiments, there is non-complementarity with at least 2 nucleotides in the complementary region.

It is contemplated that synthetic miRNA of the invention have one or more of the replacement, sugar modification, or non-complementarity designs. In certain cases, synthetic RNA molecules have two of them, while in others these molecules have all three designs in place.

The miRNA region and the complementary region may be on the same or separate polynucleotides. In cases in which they are contained on or in the same polynucleotide, the miRNA molecule will be considered a single polynucleotide. In embodiments in which the different regions are on separate polynucleotides, the synthetic miRNA will be considered to be comprised of two polynucleotides.

When the RNA molecule is a single polynucleotide, there is a linker region between the miRNA region and the complementary region. In some embodiments, the single polynucleotide is capable of forming a hairpin loop structure as a result of bonding between the miRNA region and the complementary region. The linker constitutes the hairpin loop. It is contemplated that in some embodiments, the linker region is, is at least, or is at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 residues in length, or any range derivable therein. In certain embodiments, the linker is between 3 and 30 residues (inclusive) in length.

In addition to having a miRNA region and a complementary region, there may be flanking sequences as well at either the 5' or 3' end of the region. In some embodiments, there is or is at least 1, 2, 3, 4, 5, 6, 7, 8, 9, 10 nucleotides or more, or any range derivable therein, flanking one or both sides of these regions.

RNA molecules with miRNA function may be, be at least, or be at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides, or any range derivable therein, in length. Such lengths cover the lengths of processed miRNA, miRNA probes, precursor miRNA, miRNA containing vectors, control nucleic acids, and other probes and primers. In many embodiments, miRNA are 19-24 nucleotides in length, while miRNA probes are 5, 10, 15, 20, 25, 30, to 35 nucleotides in length, including all values and ranges there between, depending on the length of the processed miRNA and any flanking regions added. miRNA precursors are generally between 62 and 110 nucleotides in humans.

Nucleic acids of the invention may have regions of identity or complementarity to another nucleic acid. It is contemplated that the region of complementarity or identity can be at least 5 contiguous residues, though it is specifically contemplated that the region is, is at least, or is at most 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or 110 contiguous nucleotides. It is further understood that the length of complementarity within a precursor miRNA or between a miRNA probe and a miRNA or a miRNA gene are such lengths. Moreover, the complementarity may be expressed as a percentage, meaning that the complementarity between a probe and its target is at least 90% identical or greater over the length of the probe. In some embodiments, complementarity is or is at least 90%, 95% or 100% identical. In particular, such lengths may be applied to any nucleic acid comprising a nucleic acid sequence identified in any of SEQ ID NOs disclosed herein.

The term "recombinant" may be used and this generally refers to a molecule that has been manipulated in vitro or that is a replicated or expressed product of such a molecule.

The term "miRNA" generally refers to an RNA molecule having a sequence and function of an miRNA molecule. In specific embodiments, molecules implemented in the invention will also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complement(s)" of a particular sequence comprising a molecule. For example, precursor miRNA may have a self-complementary region, which is up to 100% complementary. miRNA probes or nucleic acids of the invention can include, can be or can be at least 60, 65, 70, 75, 80, 85, 90, 95, 96, 97, 98, 99 or 100% complementary to their target.

Nucleic acids of the invention may be made by any technique known to one of ordinary skill in the art, such as for example, chemical synthesis, enzymatic production or biological production. It is specifically contemplated that miRNA probes of the invention are chemically synthesized.

In some embodiments of the invention, miRNAs are recovered or isolated from a biological sample. The miRNA may be recombinant or it may be natural or endogenous to the cell (produced from the cell's genome). It is contemplated that a biological sample may be treated in a way so as to enhance the recovery of small RNA molecules such as miRNA. U.S. patent application Ser. No. 10/667,126 describes such methods and it is specifically incorporated by reference herein. Generally, methods involve lysing cells with a solution having guanidinium and a detergent.

In certain aspects, synthetic miRNA of the invention are RNA or RNA analogs. miRNA inhibitors may be DNA and/or RNA, or analogs thereof. miRNA and miRNA inhibitors of the invention are collectively referred to as "synthetic nucleic acids."

In some embodiments, a therapeutic nucleic acid can have a miRNA or a synthetic miRNA sequence of between 10-200 to between 17-130 residues, including all values and ranges there between. The present invention concerns miRNA or synthetic miRNA molecules that are, are at least, or are at most 10, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 140, 150, 160, 170, 180, 190, 200 or more residues in length, including any integer or any range there between.

In certain aspects, synthetic nucleic acids have (a) a "miRNA region" whose sequence or binding region from 5' to 3' is identical or complementary to all or a segment of a mature miRNA sequence, and (b) a "complementary region" whose sequence from 5' to 3' is between 60% and 100% complementary to the miRNA sequence in (a). In certain embodiments, these synthetic nucleic acids are also isolated, as defined below. The term "miRNA region" refers to a region on the synthetic nucleic acid that is at least 75, 80, 85, 90, 95, or 100% identical, including all integers there between, to the entire sequence of a mature, naturally occurring miRNA sequence or a complement thereof. In certain embodiments, the miRNA region is or is at least 90, 91, 92, 93, 94, 95, 96, 97, 98, 99, 99.1, 99.2, 99.3, 99.4, 99.5, 99.6, 99.7, 99.8, 99.9 or 100% identical to the sequence of a naturally-occurring miRNA, or segment thereof, or complement thereof.

Discussed herein are embodiments involving miR-124 mimics. Different active and passenger strands for these mimics are described throughout the disclosure. It is contemplated that embodiments discussed in the context of a particular SEQ ID NO may be implemented in addition to or instead of other embodiments discussing the same SEQ ID NO. For example, an active strand that has at least 90% identity to SEQ ID NO:2 and also has a substitution of one of the nucleotides/nucleosides may be combined with an embodiment of an active strand involving SEQ ID NO:2 that also has an insertion in the sequence; accordingly, an active strand that has at least 90% identity to SEQ ID NO:2 would have both a substitution and an insertion with respect to SEQ ID NO:5.

It is contemplated that an RNA molecule may contain an active strand that is or is at least 90, 91, 92, 93, 94, 95, 96, 97, 98, 99 or 100% identical, or any range derivable therein, to SEQ ID NO:1. In other embodiments, the active strand is or is at least 90, 91, 92, 93, 94, 95, 96, 97, 98, 99 or 100% identical, or any range derivable therein, to SEQ ID NO:2.

In some embodiments, an active strand is 95% identical to SEQ ID NO:1 (UAAGGCACGCGGUGAAUGCC). In certain embodiments, the active strand has the following sequence from 5' to 3' in which one nucleotide from SEQ ID NO:1 is deleted:

```
                                          (SEQ ID NO: 5)
UAAGGCACGCGGUGAAUGC (C formerly at position
20 deleted)

(SEQ ID NO: 5)
UAAGGCACGCGGUGAAUGC (C formerly at position
19 deleted)

(SEQ ID NO: 6)
UAAGGCACGCGGUGAAUCC (G formerly at position
18 deleted)

(SEQ ID NO: 7)
UAAGGCACGCGGUGAAGCC (U formerly at position
17 deleted)

(SEQ ID NO: 8)
UAAGGCACGCGGUGAUGCC (A formerly at position
16 deleted)

(SEQ ID NO: 8)
UAAGGCACGCGGUGAUGCC (A formerly at position
15 deleted)

(SEQ ID NO: 9)
UAAGGCACGCGGUAAUGCC (G formerly at position
14 deleted)

(SEQ ID NO: 10)
UAAGGCACGCGGAAUGCC (U formerly at position
13 deleted)

(SEQ ID NO: 11)
UAAGGCACGCGUGAAUGCC (G formerly at position
12 deleted)

(SEQ ID NO: 11)
UAAGGCACGCGUGAAUGCC (G formerly at position
11 deleted)

(SEQ ID NO: 12)
UAAGGCACGGGUGAAUGCC (C formerly at position
10 deleted)

(SEQ ID NO: 13)
UAAGGCACCGGUGAAUGCC (G formerly at position
9 deleted)

(SEQ ID NO: 14)
UAAGGCAGCGGUGAAUGCC (C formerly at position
8 deleted)

(SEQ ID NO: 15)
UAAGGCCGCGGUGAAUGCC (A formerly at position
7 deleted)

(SEQ ID NO: 16)
UAAGGACGCGGUGAAUGCC (C formerly at position
6 deleted)

(SEQ ID NO: 17)
UAAGCACGCGGUGAAUGCC (G formerly at position
5 deleted)

(SEQ ID NO: 17)
UAAGCACGCGGUGAAUGCC (G formerly at position
4 deleted)

(SEQ ID NO: 18)
UAGGCACGCGGUGAAUGCC (A formerly at position
3 deleted)

(SEQ ID NO: 18)
UAGGCACGCGGUGAAUGCC (A formerly at position
2 deleted)

(SEQ ID NO: 19)
AAGGCACGCGGUGAAUGCC (U formerly at position
1 deleted)
```

In embodiments where a nucleotide has been deleted with respect to SEQ ID NO:1, it is contemplated that the designation of a modified nucleotide may be adjusted accordingly. In some embodiments, it is contemplated that an active strand having a sequence that is at least 95% identical to SEQ ID NO:1 has a modification of a nucleotide at one or more of the following positions: 1, 2, 3, 4, 5, 6, 7, 8, 9, 10, 11, 12, 13, 14, 15, 16, 17, 18, 19, 20, or 21 with respect to either the 5' or 3' end of the strand. In other embodiments, it is contemplated that an active strand may have the following nucleotides modified: U at position 1 relative to SEQ ID NO:1; A at position 2 relative to SEQ ID NO:1; A at position 3 relative to SEQ ID NO:1; G at position 4 relative to SEQ ID NO:1; G at position 5 relative to SEQ ID NO:1; C at position 6 relative to SEQ ID NO:1; A at position 7 relative to SEQ ID NO:1; C at position 8 relative to SEQ ID NO:1; G at position 9 relative to SEQ ID NO:1; C at position 10 relative to SEQ ID NO:1; G at position 11 relative to SEQ ID NO:1; G at position 12 relative to SEQ ID NO:1; U at position 13 relative to SEQ ID NO:1; G at position 14 relative to SEQ ID NO:1; A at position 15 relative to SEQ ID NO:1; A at position 16 relative to SEQ ID NO:1; U at position 17 relative to SEQ ID NO:1; G at position 18 relative to SEQ ID NO:1; C at position 19 relative to SEQ ID NO:1; and/or, C at position 20 relative to SEQ ID NO:1. This means that the active strand may no longer have the nucleotide at that position, but in the context of the sequence of SEQ ID NO:1, the particular nucleotide in the active strand is modified. This means its position may be altered by −1 or +1; for example, the G at position 11 relative to SEQ ID NO:1, may be at position 10 or at position 12 in the active strand because there has been an insertion or deletion that affects its position number.

In some embodiments, an active strand is 95% identical to SEQ ID NO:2 (UUAAGGCACGCGGUGAAUGCCA), which is 2 bases longer than SEQ ID NO:1. In certain embodiments, the active strand has the following sequence from 5' to 3' in which one nucleotide from SEQ ID NO:2 is deleted:

```
                                         (SEQ ID NO: 20)
UUAAGGCACGCGGUGAAUGCC (A formerly at position
22 deleted)

(SEQ ID NO: 21)
UUAAGGCACGCGGUGAAUGCA (C formerly at position
21 deleted)

(SEQ ID NO: 21)
UUAAGGCACGCGGUGAAUGCA (C formerly at position
20 deleted)

(SEQ ID NO: 22)
UUAAGGCACGCGGUGAAUCCA (G formerly at position
19 deleted)
```

-continued

UUAAGGCACGCGGUGAAGCCA (U formerly at position 18 deleted) (SEQ ID NO: 23)

UUAAGGCACGCGGUGAUGCCA (A formerly at position 17 deleted) (SEQ ID NO: 24)

UUAAGGCACGCGGUGAUGCCA (A formerly at position 16 deleted) (SEQ ID NO: 24)

UUAAGGCACGCGGUAAUGCCA (G formerly at position 15 deleted) (SEQ ID NO: 25)

UUAAGGCACGCGGGAAUGCCA (U formerly at position 14 deleted) (SEQ ID NO: 26)

UUAAGGCACGCGUGAAUGCCA (G formerly at position 13 deleted) (SEQ ID NO: 27)

UUAAGGCACGCGUGAAUGCCA (G formerly at position 12 deleted) (SEQ ID NO: 27)

UUAAGGCACGGGUGAAUGCCA (C formerly at position 11 deleted) (SEQ ID NO: 28)

UUAAGGCACCGGUGAAUGCCA (G formerly at position 10 deleted) (SEQ ID NO: 29)

UUAAGGCAGCGGUGAAUGCCA (C formerly at position 9 deleted) (SEQ ID NO: 30)

UUAAGGCCGCGGUGAAUGCCA (A formerly at position 8 deleted) (SEQ ID NO: 31)

UUAAGGACGCGGUGAAUGCCA (C formerly at position 7 deleted) (SEQ ID NO: 32)

UUAAGCACGCGGUGAAUGCCA (G formerly at position 6 deleted) (SEQ ID NO: 33)

UUAAGCACGCGGUGAAUGCCA (G formerly at position 5 deleted) (SEQ ID NO: 33)

UUAGGCACGCGGUGAAUGCCA (A formerly at position 4 deleted) (SEQ ID NO: 34)

UUAGGCACGCGGUGAAUGCCA (A formerly at position 3 deleted) (SEQ ID NO: 34)

UAAGGCACGCGGUGAAUGCCA (U formerly at position 2 deleted) (SEQ ID NO: 35)

UAAGGCACGCGGUGAAUGCCA (U formerly at position 1 deleted) (SEQ ID NO: 35)

In embodiments where a nucleotide has been deleted with respect to SEQ ID NO:2, it is contemplated that the designation of a modified nucleotide may be adjusted accordingly.

In some embodiments, it is contemplated that an active strand having a sequence that is at least 95% identical to SEQ ID NO:2 has a modification of a nucleotide at one or more of the following positions: 1, 2, 3, 4, 5, 6, 7, 8, 9, 10, 11, 12, 13, 14, 15, 16, 17, 18, 19, 20, 21 or 22 with respect to either the 5' or 3' end of the strand. In other embodiments, it is contemplated that an active strand may have the following nucleotides modified: U at position 1 relative to SEQ ID NO:2; U at position 2 relative to SEQ ID NO:2; A at position 3 relative to SEQ ID NO:2; A at position 4 relative to SEQ ID NO:2; G at position 5 relative to SEQ ID NO:2; G at position 6 relative to SEQ ID NO:2; C at position 7 relative to SEQ ID NO:2; A at position 8 relative to SEQ ID NO:2; C at position 9 relative to SEQ ID NO:2; G at position 10 relative to SEQ ID NO:2; C at position 11 relative to SEQ ID NO:2; G at position 12 relative to SEQ ID NO:2; G at position 13 relative to SEQ ID NO:12 U at position 14 relative to SEQ ID NO:2; G at position 15 relative to SEQ ID NO:2; A at position 16 relative to SEQ ID NO:2; A at position 17 relative to SEQ ID NO:2; U at position 18 relative to SEQ ID NO:2; G at position 19 relative to SEQ ID NO:2; C at position 20 relative to SEQ ID NO:2; C at position 21 relative to SEQ ID NO:2; and/or, A at position 22 relative to SEQ ID NO:2. This means that the active strand may no longer have the nucleotide at that position, but in the context of the sequence of SEQ ID NO:2, the particular nucleotide in the active strand is modified. This means its position may be altered by −1 or −2; for example, the C at position 11 relative to SEQ ID NO:2, may be at position 10 in the active strand because there has been a deletion that affects its position number.

In some embodiments, an active strand is 95% identical to SEQ ID NO:1 (UAAGGCACGCGGUGAAUGCC). In certain embodiments such an active strand has the following sequence from 5' to 3' in which one nucleotide is substituted with a different ribonucleotide (A, C, G, or U), as represented by N:

NAAGGCACGCGGUGAAUGCC (SEQ ID NO: 36)

UNAGGCACGCGGUGAAUGCC (SEQ ID NO: 37)

UANGGCACGCGGUGAAUGCC (SEQ ID N0: 38)

UAANGCACGCGGUGAAUGCC (SEQ ID NO: 39)

UAAGNCACGCGGUGAAUGCC (SEQ ID NO: 40)

UAAGGNACGCGGUGAAUGCC (SEQ ID NO: 41)

UAAGGCNCGCGGUGAAUGCC (SEQ ID NO: 42)

UAAGGCANGCGGUGAAUGCC (SEQ ID NO: 43)

UAAGGCACNGCGGUGAAUGCC (SEQ ID NO: 44)

UAAGGCACGNGGUGAAUGCC (SEQ ID NO: 45)

UAAGGCACGCNGUGAAUGCC (SEQ ID NO: 46)

UAAGGCACGCGNUGAAUGCC (SEQ ID NO: 47)

UAAGGCACGCGGNGAAUGCC (SEQ ID NO: 48)

```
                                  (SEQ ID NO: 49)
UAAGGCACGCGGUNAAUGCC (SEQ ID NO: 50)
UAAGGCACGCGGUGNAUGCC (SEQ ID NO: 51)
UAAGGCACGCGGUGANUGCC (SEQ ID NO: 52)
UAAGGCACGCGGUGAANGCC (SEQ ID NO: 53)
UAAGGCACGCGGUGAAUNCC (SEQ ID NO: 54)
UAAGGCACGCGGUGAAUGNC (SEQ ID NO: 55)
UAAGGCACGCGGUGAAUGCN
```

In some embodiments, an active strand is 95-100% identical to SEQ ID NO:1, which should include the sequences disclosed above. Other examples of such active strands include active strands with an insertion of a single nucleotide, as discussed below, in which the following sequences from 5' to 3' have an insertion of a nucleotide designated as X, which may be an A, C, G, or U:

```
                                  (SEQ ID NO: 56)
NUAAGGCACGCGGUGAAUGCC (SEQ ID NO: 57)
UNAAGGCACGCGGUGAAUGCC (SEQ ID NO: 58)
UANAGGCACGCGGUGAAUGCC (SEQ ID NO: 59)
UAANGGCACGCGGUGAAUGCC (SEQ ID NO: 60)
UAAGNGCACGCGGUGAAUGCC (SEQ ID NO: 61)
UAAGGNCACGCGGUGAAUGCC (SEQ ID NO: 62)
UAAGGCNACGCGGUGAAUGCC (SEQ ID NO: 63)
UAAGGCANCGCGGUGAAUGCC (SEQ ID NO: 64)
UAAGGCACNGCGGUGAAUGCC (SEQ ID NO: 65)
UAAGGCACGNCGGUGAAUGCC (SEQ ID NO: 66)
UAAGGCACGCNGGUGAAUGCC (SEQ ID NO: 67)
UAAGGCACGCGNGUGAAUGCC (SEQ ID NO: 68)
UAAGGCACGCGGNUGAAUGCC (SEQ ID NO: 69)
UAAGGCACGCGGUNGAAUGCC (SEQ ID NO: 70)
UAAGGCACGCGGUGNAAUGCC (SEQ ID NO: 71)
UAAGGCACGCGGUGANAUGCC (SEQ ID NO: 72)
UAAGGCACGCGGUGAANUGCC (SEQ ID NO: 73)
UAAGGCACGCGGUGAAUNGCC (SEQ ID NO: 74)
UAAGGCACGCGGUGAAUGNCC (SEQ ID NO: 75)
UAAGGCACGCGGUGAAUGCNC (SEQ ID NO: 76)
UAAGGCACGCGGUGAAUGCCN
```

In some embodiments, in addition to the single insertion shown above, there is a second insertion or addition elsewhere in the sequence relative to SEQ ID NO:1. In some embodiments, in addition to the single insertion shown above, there is a second insertion or addition elsewhere in the sequence relative to SEQ ID NO:1. It is contemplated that the second insertion may be after the nucleotide newly or previously located at position 1, 2, 3, 4, 5, 6, 7, 8, 9, 10, 11, 12, 13, 14, 15, 16, 17, 18, 19, 20, 21, 22, or 23.

In some embodiments, an active strand is or isn't at least 90% identical to SEQ ID NO:2 (UUAAGGCACGCGGUGAAUGCCA). In certain embodiments, such an active strand has the following sequence from 5' to 3' in which one or two nucleotides is substituted with a different ribonucleotide. In certain embodiment there is one substitution as represented by N:

```
                                  (SEQ ID NO: 77)
NUAAGGCACGCGGUGAAUGCCA (SEQ ID NO: 78)
UNAAGGCACGCGGUGAAUGCCA (SEQ ID NO: 79)
UUNAGGCACGCGGUGAAUGCCA (SEQ ID NO: 80)
UUANGGCACGCGGUGAAUGCCA (SEQ ID NO: 81)
UUAANGCACGCGGUGAAUGCCA (SEQ ID NO: 82)
UUAAGNCACGCGGUGAAUGCCA (SEQ ID NO: 83)
UUAAGGNACGCGGUGAAUGCCA (SEQ ID NO: 84)
UUAAGGCNCGCGGUGAAUGCCA (SEQ ID NO: 85)
UUAAGGCANGCGGUGAAUGCCA (SEQ ID NO: 86)
UUAAGGCACNGCGGUGAAUGCCA (SEQ ID NO: 87)
UUAAGGCACGNGGUGAAUGCCA (SEQ ID NO: 88)
UUAAGGCACGCNGUGAAUGCCA (SEQ ID NO: 89)
UUAAGGCACGCGNUGAAUGCCA (SEQ ID NO: 90)
UUAAGGCACGCGGNGAAUGCCA
```

-continued

UUAAGGCACGCGGUNAAUGCCA (SEQ ID NO: 91)

UUAAGGCACGCGGUGNAUGCCA (SEQ ID NO: 92)

UUAAGGCACGCGGUGANUGCCA (SEQ ID NO: 93)

UUAAGGCACGCGGUGAANGCCA (SEQ ID NO: 94)

UUAAGGCACGCGGUGAAUNCCA (SEQ ID NO: 95)

UUAAGGCACGCGGUGAAUGNCA (SEQ ID NO: 96)

UUAAGGCACGCGGUGAAUGCNA (SEQ ID NO: 97)

UUAAGGCACGCGGUGAAUGCCN (SEQ ID NO: 98)

In some embodiments, in addition to the single substitution shown above, there is a second substitution elsewhere in the sequence relative to SEQ ID NO:2. It is further contemplated that there may be a second substitution with one of the substitutions described in an active strand described above, or one or two deletions of nucleotides in addition to the substitution described above.

In some embodiments, an active strand is 95-100% identical to SEQ ID NO:2, which should include the sequences disclosed above. Other examples of such active strands include active strands with an insertion of a single nucleotide into the sequence of SEQ ID NO:2.

In certain embodiments, the active strand has a sequence that is or is at least 95% identical to SEQ ID NO:1 or SEQ ID NO:2. SEQ ID NO:1 (20 nucleotides in length) is approximately 90.9% identical to SEQ ID NO:2 (22 nucleotides in length), and a fragment of 20 contiguous nucleotides in SEQ ID NO:2 is 100% identical to SEQ ID:1.

It is noted that in some embodiments the sequence of the active strand consists of SEQ ID NO:1, which means the active strand has a sequence that is 100% identical to SEQ ID NO:1. In other embodiments, the sequence of the active strand consists of SEQ ID NO:2, which means the active strand has a sequence that is 100% identical to SEQ ID NO:2. In any of these embodiments, it is contemplated that an active strand may include a modification of a nucleotide located at position 1, 2, 3, 4, 5, 6, 7, 8, 9, 10, 11, 12, 13, 14, 15, 16, 171, 18, 19, 20, 21, and/or 22 (where position 1 is the 5' end of the strand) with respect to the 5' end of the active strand. This means the nucleotide at the recited position is modified, and this designation is independent of the identity of the particular nucleotide at that recited position. This designation is position-based, as opposed to nucleotide-based. In other embodiments, the designations are nucleotide-based. In certain embodiments, a designation may be position based with respect to the 3' end of the active strand; in such a case, the active strand may include a modification of a nucleotide located 1, 2, 3, 4, 5, 6, 7, 8, 9, 10, 11, 12, 13, 14, 15, 16, 171, 18, 19, 20, 21, and/or 22 nucleotides away from the 3' end of the active strand. Any embodiments discussed herein in which a modified nucleotide was identified as nucleotide-based may be implemented in other embodiments as a modified nucleotide that is position-based using the position of the identified nucleotide. This applies to active strands, as well as passenger strands.

In some embodiments, nucleotide-based designations set forth that an active strand may be modified at the following nucleotides: U at position 1 in SEQ ID NO:2; U at position 1 in SEQ ID NO:1 and at position 2 in SEQ ID NO:2; A at position 2 in SEQ ID NO:1 and at position 3 in SEQ ID NO:2; A at position 3 in SEQ ID NO:1 and at position 4 in SEQ ID NO:2; G at position 4 in SEQ ID NO:1 and at position 5 in SEQ ID NO:2; G at position 5 in SEQ ID NO:1 and at position 6 in SEQ ID NO:2; C at position 6 in SEQ ID NO:1 and at position 7 in SEQ ID NO:2; A at position 7 in SEQ ID NO:1 and at position 8 in SEQ ID NO:2; C at position 8 in SEQ ID NO:1 and at position 9 in SEQ ID NO:2; G at position 9 in SEQ ID NO:1 and at position 10 in SEQ ID NO:2; C at position 10 in SEQ ID NO:1 and at position 11 in SEQ ID NO:2; G at position 11 in SEQ ID NO:1 and at position 12 in SEQ ID NO:2; G at position 12 in SEQ ID NO:1 and at position 13 in SEQ ID NO:2; U at position 13 in SEQ ID NO:1 and at position 14 in SEQ ID NO:2; G at position 14 in SEQ ID NO:1 and at position 15 in SEQ ID NO:2; A at position 15 in SEQ ID NO:1 and at position 16 in SEQ ID NO:2; A at position 16 in SEQ ID NO:1 and at position 17 in SEQ ID NO:2; U at position 17 in SEQ ID NO:1 and at position 18 in SEQ ID NO:2; G at position 18 in SEQ ID NO:1 and at position 19 in SEQ ID NO:2; C at position 19 in SEQ ID NO:1 and at position 20 in SEQ ID NO:2; C at position 20 in SEQ ID NO:1 and at position 21 in SEQ ID NO:2; and/or A at position 22 in SEQ ID NO:2.

In certain embodiments, the passenger strand has a sequence that is or is at least 95% identical to SEQ ID NO:3 or SEQ ID NO:4. SEQ ID NO:3 (20 nucleotides in length) is approximately 90.9% identical to SEQ ID NO:4 (22 nucleotides in length), and a fragment of 20 contiguous nucleotides in SEQ ID NO:4 is 100% identical to SEQ ID:3.

It is noted that in some embodiments the sequence of the passenger strand consists of SEQ ID NO:3, which means the passenger strand has a sequence that is 100% identical to SEQ ID NO:3. In other embodiments, the sequence of the passenger strand consists of SEQ ID NO:4, which means the passenger strand has a sequence that is 100% identical to SEQ ID NO:4. In any of these embodiments, it is contemplated that an passenger strand may include a modification of a nucleotide located at position 1, 2, 3, 4, 5, 6, 7, 8, 9, 10, 11, 12, 13, 14, 15, 16, 171, 18, 19, 20, 21, and/or 22 (where position 1 is the 5' end of the strand) with respect to the 5' end of the passenger strand. This means the nucleotide at the recited position is modified, and this designation is independent of the identity of the particular nucleotide at that recited position. This designation is position-based, as opposed to nucleotide-based. In other embodiments, the designations are nucleotide-based. In certain embodiments, a designation may be position based with respect to the 3' end of the passenger strand; in such a case, the passenger strand may include a modification of a nucleotide located 1, 2, 3, 4, 5, 6, 7, 8, 9, 10, 11, 12, 13, 14, 15, 16, 171, 18, 19, 20, 21, and/or 22 nucleotides away from the 3' end of the passenger strand.

It is contemplated that an RNA molecule may contain a passenger strand that is or is at least 90, 91, 92, 93, 94, 95, 96, 97, 98, 99 or 100% identical, or any range derivable therein, to SEQ ID NO:3. In other embodiments, a passenger strand is or is at least 90, 91, 92, 93, 94, 95, 96, 97, 98, 99 or 100% identical, or any range derivable therein, to SEQ ID NO:4.

In some embodiments, a passenger strand is 95% identical to SEQ ID NO:3 (GGCAUUCACCGCGUGCCUUA). In certain embodiments, the active strand has the following sequence from 5' to 3' in which one nucleotide from SEQ ID NO:1 is deleted:

GGCAUUCACCGCGUGCCUU (SEQ ID NO: 99)
(A formerly at position 20 deleted)

GGCAUUCACCGCGUGCCUA (SEQ ID NO: 100)
(U formerly at position 19 deleted)

GGCAUUCACCGCGUGCCUA (SEQ ID NO: 100)
(U formerly at position 18 deleted)

GGCAUUCACCGCGUGCUA (SEQ ID NO: 101)
(C formerly at position 17 deleted)

GGCAUUCACCGCGUGCUA (SEQ ID NO: 101)
(C formerly at position 16 deleted)

GGCAUUCACCGCGUCCUA (SEQ ID NO: 102)
(G formerly at position 15 deleted)

GGCAUUCACCGCGGCCUA (SEQ ID NO: 103)
(U formerly at position 14 deleted)

GGCAUUCACCGCUGCCUA (SEQ ID NO: 104)
(G formerly at position 13 deleted)

GGCAUUCACCGGUGCCUA (SEQ ID NO: 105)
(C formerly at position 12 deleted)

GGCAUUCACCCGUGCCUA (SEQ ID NO: 106)
(G formerly at position 11 deleted)

GGCAUUCACGCGUGCCUA (SEQ ID NO: 107)
(C formerly at position 10 deleted)

GGCAUUCACGCGUGCCUA (SEQ ID NO: 107)
(C formerly at position 9 deleted)

GGCAUUCCCGCGUGCCUA (SEQ ID NO: 108)
(A formerly at position 8 deleted)

GGCAUUACCGCGUGCCUA (SEQ ID NO: 109)
(C formerly at position 7 deleted)

GGCAUCACCGCGUGCCUA (SEQ ID NO: 110)
(U formerly at position 6 deleted)

GGCAUCACCGCGUGCCUA (SEQ ID NO: 110)
(U formerly at position 5 deleted)

GGCUUCACCGCGUGCCUA (SEQ ID NO: 111)
(A formerly at position 4 deleted)

GGAUUCACCGCGUGCCUA (SEQ ID NO: 112)
(C formerly at position 3 deleted)

GCAUUCACCGCGUGCCUA (SEQ ID NO: 113)
(G formerly at position 2 deleted)

GCAUUCACCGCGUGCCUA (SEQ ID NO: 113)
(G formerly at position 1 deleted)

In embodiments where a nucleotide has been deleted with respect to SEQ ID NO:3, it is contemplated that the designation of a modified nucleotide may be adjusted accordingly.

In some embodiments, it is contemplated that an active strand having a sequence that is at least 95% identical to SEQ ID NO:3 has a modification of a nucleotide at one or more of the following positions: 1, 2, 3, 4, 5, 6, 7, 8, 9, 10, 11, 12, 13, 14, 15, 16, 17, 18, 19, 20, or 21 with respect to either the 5' or 3' end of the strand: G at position 1 relative to SEQ ID NO:3; G at position 2 relative to SEQ ID NO:3; C at position 3 relative to SEQ ID NO:3; A at position 4 relative to SEQ ID NO:3; U at position 5 relative to SEQ ID NO:3; U at position 6 relative to SEQ ID NO:3; C at position 7 relative to SEQ ID NO:3; A at position 8 relative to SEQ ID NO:3; C at position 9 relative to SEQ ID NO:3; C at position 2 relative to SEQ ID NO:10; G at position 11 relative to SEQ ID NO:3; C at position 12 relative to SEQ ID NO:3; G at position 13 relative to SEQ ID NO:3; U at position 14 relative to SEQ ID NO:3; G at position 15 relative to SEQ ID NO:3; C at position 16 relative to SEQ ID NO:3; C at position 17 relative to SEQ ID NO:3; U at position 18 relative to SEQ ID NO:3; U at position 19 relative to SEQ ID NO:3; and/or, A at position 20 relative to SEQ ID NO:3. This means that the passenger strand may no longer have the nucleotide at that position, but in the context of the sequence of SEQ ID NO:3, the particular nucleotide in the active strand is modified. This means its position may be altered by −1 or +1; for example, the G at position 11 relative to SEQ ID NO:3, may be at position 10 or at position 12 in a passenger strand because there has been an insertion or deletion that affects its position number.

In some embodiments, a passenger strand is 95% identical to SEQ ID NO:4 (UGGCAUUCACCGCGUGCCUUAA), which is 2 bases longer than SEQ ID NO:3. In certain embodiments, the passenger strand has the following sequence from 5' to 3' in which one nucleotide from SEQ ID NO:4 is deleted:

UGGCAUUCACCGCGUGCCUUA (SEQ ID NO: 114)
(A formerly at position 22 deleted)

UGGCAUUCACCGCGUGCCUUA (SEQ ID NO: 114)
(A formerly at position 21 deleted)

UGGCAUUCACCGCGUGCCUAA (SEQ ID NO: 115)
(U formerly at position 20 deleted)

UGGCAUUCACCGCGUGCCUAA (SEQ ID NO: 115)
(U formerly at position 19 deleted)

UGGCAUUCACCGCGUGCUUAA (SEQ ID NO: 116)
(C formerly at position 18 deleted)

UGGCAUUCACCGCGUGCUUAA (SEQ ID NO: 116)
(C formerly at position 17 deleted)

UGGCAUUCACCGCGUCCUUAA (SEQ ID NO: 117)
(G formerly at position 16 deleted)

-continued

UGGCAUUCACCGCGGCCUUAA (U formerly at position 15 deleted) (SEQ ID NO: 118)

UGGCAUUCACCGCUGCCUUAA (G formerly at position 14 deleted) (SEQ ID NO: 119)

UGGCAUUCACCGGUGCCUUAA (C formerly at position 13 deleted) (SEQ ID NO: 120)

UGGCAUUCACCCGUGCCUUAA (G formerly at position 12 deleted) (SEQ ID NO: 121)

UGGCAUUCACGCGUGCCUUAA (C formerly at position 11 deleted) (SEQ ID NO: 122)

UGGCAUUCACGCGUGCCUUAA (C formerly at position 10 deleted) (SEQ ID NO: 122)

UGGCAUUCCCGCGUGCCUUAA (A formerly at position 9 deleted) (SEQ ID NO: 123)

UGGCAUUACCGCGUGCCUUAA (C formerly at position 8 deleted) (SEQ ID NO: 124)

UGGCAUCACCGCGUGCCUUAA (U formerly at position 7 deleted) (SEQ ID NO: 125)

UGGCAUCACCGCGUGCCUUAA (U formerly at position 6 deleted) (SEQ ID NO: 125)

UGGCUUCACCGCGUGCCUUAA (A formerly at position 5 deleted) (SEQ ID NO: 126)

UGGAUUCACCGCGUGCCUUAA (C formerly at position 4 deleted) (SEQ ID NO: 127)

UGCAUUCACCGCGUGCCUUAA (G formerly at position 3 deleted) (SEQ ID NO: 128)

UGCAUUCACCGCGUGCCUUAA (G formerly at position 2 deleted) (SEQ ID NO: 129)

GGCAUUCACCGCGUGCCUUAA (U formerly at position 1 deleted) (SEQ ID NO: 130)

In embodiments where a nucleotide has been deleted with respect to SEQ ID NO:4, it is contemplated that the designation of a modified nucleotide may be adjusted accordingly. In some embodiments, it is contemplated that an active strand having a sequence that is at least 95% identical to SEQ ID NO:4 has a modification of a nucleotide at one or more of the following positions: 1, 2, 3, 4, 5, 6, 7, 8, 9, 10, 11, 12, 13, 14, 15, 16, 17, 18, 19, 20, 21 or 22 with respect to either the 5' or 3' end of the strand. In other embodiments, it is contemplated that an active strand may have the following nucleotides modified:

U at position 1 relative to SEQ ID NO:4; G at position 2 relative to SEQ ID NO:4; G at position 3 relative to SEQ ID NO:4; C at position 4 relative to SEQ ID NO:4; A at position 5 relative to SEQ ID NO:4; U at position 6 relative to SEQ ID NO:4; U at position 7 relative to SEQ ID NO:4; C at position 8 relative to SEQ ID NO:4; A at position 9 relative to SEQ ID NO:4; C at position 10 relative to SEQ ID NO:4; C at position 11 relative to SEQ ID NO:4; G at position 12 relative to SEQ ID NO:4; C at position 13 relative to SEQ ID NO:4; G at position 14 relative to SEQ ID NO:4; U at position 15 relative to SEQ ID NO:4; G at position 16 relative to SEQ ID NO:4; C at position 17 relative to SEQ ID NO:4; C at position 18 relative to SEQ ID NO:4; U at position 19 relative to SEQ ID NO:4; U at position 20 relative to SEQ ID NO:4; A at position 21 relative to SEQ ID NO:4; and/or A at position 20 relative to SEQ ID NO:4. This means that the active strand may no longer have the nucleotide at that position, but in the context of the sequence of SEQ ID NO:2, the particular nucleotide in the active strand is modified. This means its position may be altered by −1 or −2; for example, the C at position 11 relative to SEQ ID NO:2, may be at position 10 in the active strand because there has been a deletion that affects its position number.

In some embodiments, a passenger strand is 95% identical to SEQ ID NO:3 (GGCAUUCACCGCGUGCCUUA). In certain embodiments such a passenger strand has the following sequence from 5' to 3' in which one nucleotide is substituted with a different ribonucleotide (A, C, G, or U), as represented by N:

NGCAUUCACCGCGUGCCUUA (SEQ ID NO: 131)

GNCAUUCACCGCGUGCCUUA (SEQ ID NO: 132)

GGNAUUCACCGCGUGCCUUA (SEQ ID NO: 133)

GGCNUUCACCGCGUGCCUUA (SEQ ID NO: 134)

GGCANUCACCGCGUGCCUUA (SEQ ID NO: 135)

GGCAUNCACCGCGUGCCUUA (SEQ ID NO: 136)

GGCAUUNACCGCGUGCCUUA (SEQ ID NO: 137)

GGCAUUCNCCGCGUGCCUUA (SEQ ID NO: 138)

GGCAUUCANCGCGUGCCUUA (SEQ ID NO: 139)

GGCAUUCACNGCGUGCCUUA (SEQ ID NO: 140)

GGCAUUCACCNCGUGCCUUA (SEQ ID NO: 141)

GGCAUUCACCGNGUGCCUUA (SEQ ID NO: 142)

GGCAUUCACCGCNUGCCUUA (SEQ ID NO: 143)

GGCAUUCACCGCGNGCCUUA (SEQ ID NO: 144)

GGCAUUCACCGCGUNCCUUA (SEQ ID NO: 145)

GGCAUUCACCGCGUGNCUUA (SEQ ID NO: 146)

GGCAUUCACCGCGUGCNUUA (SEQ ID NO: 147)

GGCAUUCACCGCGUGCCNUA (SEQ ID NO: 148)

GGCAUUCACCGCGUGCCUNA (SEQ ID NO: 149)

GGCAUUCACCGCGUGCCUUN (SEQ ID NO: 150)

In some embodiments, in addition to the single substitution shown above, there is a second substitution elsewhere in the sequence relative to SEQ ID NO:3. It is further contemplated that there may be a second substitution with one of the substitutions described in a passenger strand described above, or one or two deletions of nucleotides in addition to the substitution described above.

In some embodiments, a passenger strand is 95-100% identical to SEQ ID NO:3, which should include the sequences disclosed above. Other examples of such active strands include active strands with an insertion of a single nucleotide, as discussed below, in which the following sequences from 5' to 3' have an insertion of a nucleotide designated as X, which may be an A, C, G, or U:

NGGCAUUCACCGCGUGCCUUA (SEQ ID NO: 151)

GNGCAUUCACCGCGUGCCUUA (SEQ ID NO: 152)

GGNCAUUCACCGCGUGCCUUA (SEQ ID NO: 153)

GGCNAUUCACCGCGUGCCUUA (SEQ ID NO: 154)

GGCANUUCACCGCGUGCCUUA (SEQ ID NO: 155)

GGCAUNUCACCGCGUGCCUUA (SEQ ID NO: 156)

GGCAUUNCACCGCGUGCCUUA (SEQ ID NO: 157)

GGCAUUCNACCGCGUGCCUUA (SEQ ID NO: 158)

GGCAUUCANCCGCGUGCCUUA (SEQ ID NO: 159)

GGCAUUCACNCGCGUGCCUUA (SEQ ID NO: 160)

GGCAUUCACCNGCGUGCCUUA (SEQ ID NO: 161)

GGCAUUCACCGNCGUGCCUUA (SEQ ID NO: 162)

GGCAUUCACCGCNGUGCCUUA (SEQ ID NO: 163)

GGCAUUCACCGCGNUGCCUUA (SEQ ID NO: 164)

GGCAUUCACCGCGUNGCCUUA (SEQ ID NO: 165)

GGCAUUCACCGCGUGNCCUUA (SEQ ID NO: 166)

GGCAUUCACCGCGUGCNCUUA (SEQ ID NO: 167)

GGCAUUCACCGCGUGCCNUUA (SEQ ID NO: 168)

GGCAUUCACCGCGUGCCUNUA (SEQ ID NO: 169)

GGCAUUCACCGCGUGCCUUNA (SEQ ID NO: 170)

GGCAUUCACCGCGUGCCUUAN (SEQ ID NO: 171)

In some embodiments, in addition to the insertion in the passenger strand shown above relative to SEQ ID NO:3, there may be a second insertion elsewhere in the strand. Combinations of insertions in the passengers strands shown above are also contemplated for additional passenger strands.

In some embodiments, a passenger strand is or is at least 90% identical to SEQ ID NO:4 (UGGCAUUCACCGCGUGCCUUAA). In certain embodiments, such a passenger strand has the following sequence from 5' to 3' in which one or two nucleotides is substituted with a different ribonucleotide. In certain embodiment there is one substitution as represented by N:

NGGCAUUCACCGCGUGCCUUAA (SEQ ID NO: 172)

UNGCAUUCACCGCGUGCCUUAA (SEQ ID NO: 173)

UGNCAUUCACCGCGUGCCUUAA (SEQ ID NO: 174)

UGGNAUUCACCGCGUGCCUUAA (SEQ ID NO: 175)

UGGCNUUCACCGCGUGCCUUAA (SEQ ID NO: 176)

UGGCANUCACCGCGUGCCUUAA (SEQ ID NO: 177)

UGGCAUNCACCGCGUGCCUUAA (SEQ ID NO: 178)

UGGCAUUNACCGCGUGCCUUAA (SEQ ID NO: 179)

UGGCAUUCNCCGCGUGCCUUAA (SEQ ID NO: 180)

UGGCAUUCANCGCGUGCCUUAA (SEQ ID NO: 181)

UGGCAUUCACNGCGUGCCUUAA (SEQ ID NO: 182)

UGGCAUUCACCNCGUGCCUUAA (SEQ ID NO: 183)

UGGCAUUCACCGNGUGCCUUAA (SEQ ID NO: 184)

UGGCAUUCACCGCNUGCCUUAA (SEQ ID NO: 185)

UGGCAUUCACCGCGNGCCUUAA (SEQ ID NO: 186)

UGGCAUUCACCGCGUNCCUUAA (SEQ ID NO: 187)

UGGCAUUCACCGCGUGNCUUAA (SEQ ID NO: 188)

-continued

UGGCAUUCACCGCGUGCNUUAA (SEQ ID NO: 189)

UGGCAUUCACCGCGUGCCNUAA (SEQ ID NO: 190)

UGGCAUUCACCGCGUGCCUNAA (SEQ ID NO: 191)

UGGCAUUCACCGCGUGCCUUNA (SEQ ID NO: 192)

UGGCAUUCACCGCGUGCCUUAX (SEQ ID NO: 193)

In some embodiments, in addition to the single substitution shown above, there is a second substitution elsewhere in the sequence relative to SEQ ID NO:4. Moreover, any combination of substitutions shown above in the passenger strands is contemplated.

In some embodiments, a passenger strand is 95-100% identical to SEQ ID NO:4, which should include the sequences disclosed above. Other examples of such passenger strands include passenger strands with an insertion of a single nucleotide into the sequence of SEQ ID NO:4.

It is noted that in some embodiments the sequence of the passenger strand consists of SEQ ID NO:3, which means the passenger strand has a sequence that is 100% identical to SEQ ID NO:3. In other embodiments, the sequence of the passenger strand consists of SEQ ID NO:4, which means the passenger strand has a sequence that is 100% identical to SEQ ID NO:4. In any of these embodiments, it is contemplated that a passenger strand may include a modification of a nucleotide located at position 1, 2, 3, 4, 5, 6, 7, 8, 9, 10, 11, 12, 13, 14, 15, 16, 171, 18, 19, 20, 21, and/or 22 (where position 1 is the 5' end of the strand) with respect to the 5' end of the passenger strand. This means the nucleotide at the recited position is modified, and this designation is independent of the identity of the particular nucleotide at that recited position. This designation is position-based, as opposed to nucleotide-based. In other embodiments, the designations are nucleotide-based. In certain embodiments, a designation may be position based with respect to the 3' end of the passenger strand; in such a case, the passenger strand may include a modification of a nucleotide located 1, 2, 3, 4, 5, 6, 7, 8, 9, 10, 11, 12, 13, 14, 15, 16, 171, 18, 19, 20, 21, and/or 22 nucleotides away from the 3' end of the passenger strand.

In some embodiments, nucleotide-based designations set forth that a passenger strand may be modified at the following nucleotides: U at position 1 in SEQ ID NO:4; G at position 2 in SEQ ID NO:4; G at position 3 in SEQ ID NO:4; C at position 4 in SEQ ID NO:4; A at position 5 in SEQ ID NO:4; U at position 6 in SEQ ID NO:4; U at position 7 in SEQ ID NO:4; C at position 8 in SEQ ID NO:4; A at position 9 in SEQ ID NO:4; C at position 10 in SEQ ID NO:4; C at position 11 in SEQ ID NO:4; G at position 12 in SEQ ID NO:4; C at position 13 in SEQ ID NO:4; G at position 14 in SEQ ID NO:4; U at position 15 in SEQ ID NO:4; G at position 16 in SEQ ID NO:4; C at position 17 in SEQ ID NO:4; C at position 18 in SEQ ID NO:4; U at position 19 in SEQ ID NO:4; U at position 20 in SEQ ID NO:4; A at position 21 in SEQ ID NO:4; and/or, A at position 22 in SEQ ID NO:4.

The term "complementary region" or "complement" refers to a region of a nucleic acid or mimic that is or is at least 60% complementary to the mature, naturally occurring miRNA sequence. The complementary region is or is at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein. With single polynucleotide sequences, there may be a hairpin loop structure as a result of chemical bonding between the miRNA region and the complementary region. In other embodiments, the complementary region is on a different nucleic acid molecule than the miRNA region, in which case the complementary region is on the complementary strand and the miRNA region is on the active strand.

When the RNA molecule is a single polynucleotide, there can be a linker region between the miRNA region and the complementary region. In some embodiments, the single polynucleotide is capable of forming a hairpin loop structure as a result of bonding between the miRNA region and the complementary region. The linker constitutes the hairpin loop. It is contemplated that in some embodiments, the linker region is, is at least, or is at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 residues in length, or any range derivable therein. In certain embodiments, the linker is between 3 and 30 residues (inclusive) in length.

A. Isolation of Nucleic Acids

Nucleic acids may be isolated using techniques well known to those of skill in the art, though in particular embodiments, methods for isolating small nucleic acid molecules, and/or isolating RNA molecules can be employed. Chromatography is a process often used to separate or isolate nucleic acids from protein or from other nucleic acids. Such methods can involve electrophoresis with a gel matrix, filter columns, capillary electrophoresis, alcohol precipitation, and/or other chromatography. If miRNA from cells is to be used or evaluated, methods generally involve lysing the cells with a chaotropic agent (e.g., guanidinium isothiocyanate) and/or detergent (e.g., N-lauroyl sarcosine) prior to implementing processes for isolating particular populations of RNA.

In particular methods for separating miRNA from other nucleic acids, a gel matrix is prepared using polyacrylamide, though agarose can also be used. The gels may be graded by concentration or they may be uniform. Plates or tubing can be used to hold the gel matrix for electrophoresis. Usually one-dimensional electrophoresis is employed for the separation of nucleic acids. Plates are used to prepare a slab gel, while the tubing (glass or rubber, typically) can be used to prepare a tube gel. The phrase "tube electrophoresis" refers to the use of a tube or tubing, instead of plates, to form the gel. Materials for implementing tube electrophoresis can be readily prepared by a person of skill in the art or purchased, such as from C.B.S. Scientific Co., Inc. or Scie-Plas.

Methods may involve the use of organic solvents and/or alcohol to isolate nucleic acids, particularly miRNA used in methods and compositions of the invention. Some embodiments are described in U.S. patent application Ser. No. 10/667,126, which is hereby incorporated by reference. Generally, this disclosure provides methods for efficiently isolating small RNA molecules from cells comprising: adding an alcohol solution to a cell lysate and applying the alcohol/lysate mixture to a solid support before eluting the RNA molecules from the solid support. In some embodiments, the amount of alcohol added to a cell lysate achieves an alcohol concentration of about 55% to 60%. While different alcohols can be employed, ethanol works well. A solid support may be any structure, and it includes beads, filters, and columns, which may include a mineral or polymer support with electronegative groups. A glass fiber filter or column has worked particularly well for such isolation procedures.

In specific embodiments, miRNA isolation processes include: a) lysing cells in the sample with a lysing solution comprising guanidinium, wherein a lysate with a concentration of at least about 1 M guanidinium is produced; b) extracting miRNA molecules from the lysate with an extraction solution comprising phenol; c) adding to the lysate an alcohol solution for form a lysate/alcohol mixture, wherein the concentration of alcohol in the mixture is between about 35% to about 70%; d) applying the lysate/alcohol mixture to a solid support; e) eluting the miRNA molecules from the solid support with an ionic solution; and, f) capturing the miRNA molecules. Typically the sample is dried down and resuspended in a liquid and volume appropriate for subsequent manipulation.

B. Preparation of Nucleic Acids

Alternatively, nucleic acid synthesis is performed according to standard methods. See, for example, Itakura and Riggs (1980). Additionally, U.S. Pat. Nos. 4,704,362, 5,221,619, and 5,583,013 each describe various methods of preparing synthetic nucleic acids. Non-limiting examples of a synthetic nucleic acid (e.g., a synthetic oligonucleotide), include a nucleic acid made by in vitro chemically synthesis using phosphotriester, phosphite, or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods described herein, one or more oligonucleotide may be used. Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid includes one produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference. Non-limiting examples of a biologically produced nucleic acid include a recombinant nucleic acid produced (i.e., replicated) in a living cell, such as a recombinant DNA vector replicated in bacteria or recombinant RNA or RNA vectors replicated in viruses (see for example, Sambrook et al., 2001, incorporated herein by reference).

Recombinant methods for producing nucleic acids in a cell are well known to those of skill in the art. These include the use of vectors (viral and non-viral), plasmids, cosmids, and other vehicles for delivering a nucleic acid to a cell, which may be the target cell (e.g., a cancer cell) or simply a host cell (to produce large quantities of the desired RNA molecule). Alternatively, such vehicles can be used in the context of a cell free system so long as the reagents for generating the RNA molecule are present. Such methods include those described in Sambrook, 2003, Sambrook, 2001 and Sambrook, 1989, which are hereby incorporated by reference.

In certain embodiments, the present invention concerns nucleic acid molecules that are not synthetic. In some embodiments, the nucleic acid molecule has a chemical structure of a naturally occurring nucleic acid and a sequence of a naturally occurring nucleic acid, such as the exact and entire sequence of a single stranded primary miRNA (see Lee, 2002), a single-stranded precursor miRNA, or a single-stranded mature miRNA.

II. THERAPEUTIC METHODS

Certain embodiments concern nucleic acids that perform the activities of endogenous miR-124 when introduced into cells. In certain aspects, therapeutic nucleic acids (also referred to as nucleic acids) can be synthetic, non-synthetic, or a combination of synthetic and non-synthetic miRNA sequences. Embodiments concern, in certain aspects, short nucleic acid molecules (therapeutic nucleic acids) that function as miR-124. The nucleic acid molecules are typically synthetic. The term "synthetic" refers to a nucleic acid molecule that is chemically synthesized by a machine or apparatus and not produced naturally in a cell.

In certain aspects, RNA molecules may not have an entire sequence that is identical or complementary to a sequence of a naturally-occurring mature miRNA. Such molecules may encompass all or part of a naturally-occurring sequence or a complement thereof. For example, a synthetic nucleic acid may have a sequence that differs from the sequence of a mature miRNA, but that altered sequence may provide one or more functions that can be achieved with the natural sequence.

The term "isolated" means that the nucleic acid molecules are initially separated from different molecules (in terms of sequence or structure) and unwanted nucleic acid molecules such that a population of isolated nucleic acids is at least about 90% homogenous, and may be at least about 95, 96, 97, 98, 99, or 100% homogenous with respect to other polynucleotide molecules. In many aspects of the invention, a nucleic acid is isolated by virtue of it having been synthesized in vitro separate from endogenous nucleic acids in a cell. It will be understood, however, that isolated nucleic acids may be subsequently mixed or pooled together.

In certain methods, there is a further step of administering the selected miRNA mimic or RNA molecule to a cell, tissue, organ, or organism (collectively "biological matter") in need of treatment related to modulation of the targeted miRNA or in need of the physiological or biological results discussed herein (such as with respect to a particular cellular pathway or result like decrease in cell viability). Consequently, in some methods there is a step of identifying a patient in need of treatment that can be provided by the miRNA mimic(s). It is contemplated that an effective amount of an miRNA mimic can be administered in some embodiments. In particular embodiments, there is a therapeutic benefit conferred on the biological matter, where a "therapeutic benefit" refers to an improvement in the one or more conditions or symptoms associated with a disease or condition or an improvement in the prognosis, duration, or status with respect to the disease. It is contemplated that a therapeutic benefit includes, but is not limited to, a decrease in pain, a decrease in morbidity, a decrease in a symptom. For example, with respect to cancer, it is contemplated that a therapeutic benefit can be inhibition of tumor growth, prevention of metastasis, reduction in number of metastases, inhibition of cancer cell proliferation, inhibition of cancer cell proliferation, induction of cell death in cancer cells, inhibition of angiogenesis near cancer cells, induction of apoptosis of cancer cells, reduction in pain, reduction in risk of recurrence, induction of chemo- or radiosensitivity in cancer cells, prolongation of life, and/or delay of death directly or indirectly related to cancer.

In certain embodiments, an miRNA mimic is used to treat cancer. Cancer includes, but is not limited to, malignant cancers, tumors, metastatic cancers, unresectable cancers, chemo- and/or radiation-resistant cancers, and terminal cancers.

Cancers that may be evaluated, diagnosed, and/or treated by methods and compositions of the invention include cancer cells from the bladder, blood, bone, bone marrow, brain, breast, cardiovascular system, cervix, colon, connective tissue, endometrium, epithelium, esophagus, fat, gastrointestine, glands, gum, head, kidney, liver, lung, meninges, muscle, nasopharynx, neck, neurons, ovary, pancreas, prostate, rectum, retina, skin, spleen, stomach, testis, thymus, thyroid, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyo sarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Moreover, miRNA mimics can be used for precancerous cells, such as those cells in metaplasia, dysplasia, and hyperplasia.

Methods include supplying or enhancing the activity of one or more miRNAs in a cell. Methods also concern inducing certain cellular characteristics by providing to a cell a particular nucleic acid, such as a specific therapeutic nucleic acid molecule, i.e., a miRNA mimic molecule. The therapeutic miRNA mimic may have a sequence that is identical to a naturally occurring miRNA with one or more design modifications.

In certain aspects, a particular nucleic acid molecule provided to the cell is understood to correspond to a particular miRNA in the cell, and thus, the miRNA in the cell is referred to as the "corresponding miRNA." In situations in which a named miRNA molecule is introduced into a cell, the corresponding miRNA will be understood to provide miRNA function. It is contemplated, however, that the therapeutic nucleic acid introduced into a cell is not a mature miRNA but is capable of becoming or functioning as a mature miRNA under the appropriate physiological conditions. In cases in which a particular corresponding gene or gene transcript is being targeted by an miRNA mimic, the particular gene or gene transcript will be referred to as the "targeted gene." It is contemplated that multiple corresponding genes may be targeted by one or more different miRNA mimics. In particular embodiments, more than one therapeutic nucleic acid is introduced into a cell. Moreover, in other embodiments, more than one miRNA inhibitor is introduced into a cell. Furthermore, a combination of therapeutic nucleic acid(s) may be introduced into a cell. The inventors contemplate that a combination of therapeutic nucleic acids may act at one or more points in cellular pathways of cells and that such combination may have increased efficacy on the target cell while not adversely effecting normal or non-targeted cells. Thus, a combination of therapeutic nucleic acids may have a minimal adverse effect on a subject or patient while supplying a sufficient therapeutic effect, such as amelioration of a condition, growth inhibition of a cell, death of a targeted cell, alteration of cell phenotype or physiology, slowing of cellular growth, sensitization to a second therapy, sensitization to a particular therapy, and the like.

Methods include identifying a cell or patient in need of inducing those therapeutics effects or cellular characteristics. Also, it will be understood that an amount of a therapeutic nucleic acid that is provided to a cell or organism is an "effective amount," which refers to an amount needed (or a sufficient amount) to achieve a desired goal, such as inducing a particular therapeutic effect or cellular characteristic(s) or reducing cancer growth or killing cancer cells or alleviating symptoms associated with a cancer.

In certain aspects methods can include providing or introducing to a cell a nucleic acid molecule corresponding to a mature miRNA in the cell in an amount effective to achieve a desired physiological result. Moreover, methods can involve providing multiple synthetic therapeutic nucleic acids. It is contemplated that in these embodiments, methods may or may not be limited to providing only one or more synthetic molecules. In this situation, a cell or cells may be provided with a synthetic molecule corresponding to a particular miRNA and a synthetic molecule corresponding to a different miRNA. Furthermore, any method articulated using a list of miRNA targets using Markush group language may be articulated without the Markush group language and a disjunctive article (i.e., or) instead, and vice versa.

In some embodiments, there is a method for reducing or inhibiting cell proliferation, propagation, or renewal in a cell comprising introducing into or providing to the cell an effective amount of (i) a therapeutic nucleic acid or (ii) a synthetic molecule that corresponds to a miRNA sequence. In certain embodiments the methods involve introducing into the cell an effective amount of (i) a miRNA inhibitor molecule having a 5' to 3' sequence that is at least 90% complementary to the 5' to 3' sequence of one or more miRNA.

Certain aspects of the invention include methods of treating a pathologic condition, such as cancer or precancerous conditions. In one aspect, the method comprises contacting a target cell with one or more nucleic acids comprising at least one nucleic acid segment having all or a portion of a miRNA sequence or a complement thereof. The segment may be 5, 6, 7, 8, 9, 10, 11, 12, 13, 14, 15, 16, 17, 18, 19, 20, 21, 22, 23, 24, 25, 30 or more nucleotides or nucleotide analog, including all integers there between. An aspect of the invention includes the modulation of gene expression, miRNA expression or function or mRNA expression or function within a target cell, such as a prostate cancer cell or cancer stem cell (CSC).

Typically, an endogenous gene, miRNA or mRNA is modulated in the cell. In certain aspects, a therapeutic nucleic acid sequence comprises at least one segment that is at least 70, 75, 80, 85, 90, 95, or 100% identical in nucleic acid sequence to one or more miRNA or gene sequence or complement thereof. Modulation of the expression or processing of a gene, miRNA, or mRNA of the cell or a virus can be through modulation of the processing of a nucleic acid, such processing including transcription, transportation and/or translation within a cell. Modulation may also be effected by the inhibition or enhancement of miRNA activity with a cell, tissue, or organ. Such processing may affect the expression of an encoded product or the stability of the mRNA.

It will be understood in methods of the invention that a cell or other biological matter such as an organism (including patients) can be provided a therapeutic nucleic acid corresponding to or targeting a particular miRNA by administering to the cell or organism a nucleic acid molecule that functions as the corresponding miRNA once inside the cell. Thus, it is contemplated that a nucleic acid is provided such that it becomes processed into a mature and active miRNA once it has access to the cell's processing machinery. In certain aspects, it is specifically contemplated that the miRNA molecule provided is not a mature molecule but a nucleic acid molecule that can be processed into the mature miRNA or its functional equivalent once it is accessible to processing machinery.

The term "non-synthetic" in the context of miRNA means that the miRNA is not "synthetic," as defined herein. Furthermore, it is contemplated that in embodiments of the invention that concern the use of synthetic miRNAs, the use of corresponding non-synthetic miRNAs is also considered an aspect of the invention, and vice versa. It will be understood that the term "providing" an agent is used to include "administering" the agent to a patient.

In certain embodiments, methods also include targeting an miRNA in a cell or organism. The term "corresponding to a miRNA" means a nucleic acid will be employed so as to mimic (provide the activity or function of) a selected miRNA.

Furthermore, it is contemplated that the nucleic acid compositions may be provided as part of a therapy to a patient, in conjunction with traditional therapies or preventative agents. Moreover, it is contemplated that any method discussed in the context of therapy may be applied as preventatively, particularly in a patient identified to be potentially in need of the therapy or at risk of the condition or disease for which a therapy is needed.

In addition, methods of the invention concern employing one or more nucleic acid corresponding to a miRNA and a therapeutic drug. The nucleic acid can enhance the effect or efficacy of the drug, reduce any side effects or toxicity, modify its bioavailability, and/or decrease the dosage or frequency needed. In certain embodiments, the therapeutic drug is a cancer therapeutic. Consequently, in some embodiments, there is a method of treating a precancer or cancer in a patient comprising administering to the patient a cancer therapeutic (i.e., a second therapeutic) and an effective amount of at least one nucleic acid molecule that improves the efficacy of the cancer therapeutic or protects non-cancer cells. Cancer therapies also include a variety of combination therapies with both chemical and radiation based treatments.

Generally, miRNA mimics can be given to decrease the activity of a nucleic acid targeted by the miRNA. Methods generally contemplated include providing or introducing one or more different nucleic acid molecules corresponding to one or more different genes. It is contemplated that the following, at least the following, or at most the following number of different nucleic acid or miRNA molecules may be detected, assessed, provided or introduced: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more, including any value or range derivable there between.

III. PHARMACEUTICAL FORMULATIONS AND DELIVERY

Methods include the delivery of an effective amount of a therapeutic nucleic acid comprising or consisting essentially of a mature miRNA sequence. An "effective amount" of the pharmaceutical composition, generally, is defined as that amount sufficient to detectably and repeatedly to achieve the stated desired result, for example, to ameliorate, reduce, minimize or limit the extent of the disease or its symptoms.

Other more rigorous definitions may apply, including elimination, eradication or cure of disease.

In certain embodiments, it is desired to kill cells, inhibit cell growth, inhibit metastasis, decrease tumor or tissue size, and/or reverse or reduce the malignant or disease phenotype of cells. The routes of administration will vary, naturally, with the location and nature of the lesion or site to be targeted, and include, e.g., intradermal, subcutaneous, regional, parenteral, intravenous, intramuscular, intranasal, systemic, and oral administration and formulation. Injection or perfusion of a therapeutic nucleic acid is specifically contemplated for discrete, solid, accessible precancers or cancers, or other accessible target areas. Local, regional, or systemic administration also may be appropriate.

In the case of surgical intervention, the present invention may be used preoperatively, to render an inoperable lesion subject to resection. Alternatively, the present invention may be used at the time of surgery, and/or thereafter, to treat residual or metastatic disease. For example, a resected tumor bed may be injected or perfused with a formulation comprising a therapeutic nucleic acid or combinations thereof. Administration may be continued post-resection, for example, by leaving a catheter implanted at the site of the surgery. Periodic post-surgical treatment also is envisioned. Continuous perfusion of a nucleic acid also is contemplated.

Continuous administration also may be applied where appropriate, for example, where a tumor or other undesired affected area is excised and the tumor bed or targeted site is treated to eliminate residual, microscopic disease. Delivery via syringe or cauterization is contemplated. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs.

Treatment regimens may vary as well and often depend on the type and/or location of a lesion, the target site, disease progression, and the health, immune condition, and age of the patient. Certain tumor types will require more aggressive treatment. The clinician will be best suited to make such decisions based on the known efficacy and toxicity (if any) of the therapeutic formulations.

In certain embodiments, the lesion or affected area being treated may not, at least initially, be resectable. Treatments with compositions of the invention may increase the resectability of the lesion due to shrinkage at the margins or by elimination of certain particularly invasive portions. Following treatments, resection may be possible. Additional treatments subsequent to resection may serve to eliminate microscopic residual disease at the tumor or targeted site.

Treatments may include various "unit doses." A unit dose is defined as containing a predetermined quantity of a therapeutic composition(s). The quantity to be administered, and the particular route and formulation, are within the skill of those in the clinical arts. A unit dose need not be administered as a single injection but may comprise continuous infusion over a set period of time. A unit dose may conveniently be described in terms of ng, µg, or mg of miRNA or miRNA mimic. Alternatively, the amount specified may be the amount administered as the average daily, average weekly, or average monthly dose.

A therapeutic nucleic acid can be administered to the patient in a dose or doses of about or of at least about 0.5, 1, 5, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 ng, µg or mg, or more, or any range derivable therein. Alternatively, the amount specified may be the amount administered as the average daily, average weekly, or average monthly dose, or it may be expressed in terms of mg/kg, where kg refers to the weight of the patient and the mg is specified above. In other embodiments, the amount specified is any number discussed above but expressed as mg/m$^2$ (with respect to tumor size or patient surface area). In some embodiments, a dose or regimen may be administered every 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 day(s), and/or 1, 2, 3, 4 weeks, and any range derivable therein, to a patient in need of treatment.

In some embodiments, the method for the delivery of a therapeutic nucleic acid is via local or systemic administration. However, the pharmaceutical compositions disclosed herein may also be administered parenterally, subcutaneously, intratracheally, intravenously, intradermally, intramuscularly, or even intraperitoneally as described in U.S. Pat. Nos. 5,543,158; 5,641,515 and 5,399,363 (each specifically incorporated herein by reference in its entirety).

Injection of nucleic acids may be delivered by syringe or any other method used for injection of a solution, as long as the nucleic acid and any associated components can pass through the particular gauge of needle required for injection. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, mixtures thereof, and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). Typically, the form must be sterile and must be fluid to the extent that easy syringability exists. It must be stable under the conditions of manufacture and storage and preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In certain formulations, a water-based formulation is employed while in others, it may be lipid-based. In particular embodiments of the invention, a composition comprising a nucleic acid of the invention is in a water-based formulation. In other embodiments, the formulation is lipid based.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral, intralesional, and intraperitoneal administration. In this connection, sterile aqueous media which can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards. As used herein, a "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically acceptable" refers to molecular entities and compositions that do not produce an allergic or similar untoward reaction when administered to a human. The nucleic acid(s) are administered in a manner compatible with the dosage formulation, and in such amount as will be therapeutically effective. The quantity to be administered depends on the subject to be treated, including, e.g., the aggressiveness of the disease or cancer, the size of any tumor(s) or lesions, the previous or other courses of treatment. Precise amounts of active ingredient required to be administered depend on the judgment of the practitioner. Suitable regimes for initial administration and subsequent administration are also variable, but are typified by an initial administration followed by other administrations. Such administration may be systemic, as a single dose, continuous over a period of time spanning 10, 20, 30, 40, 50, 60 minutes, and/or 1, 2, 3, 4, 5, 6, 7, 8, 9, 10, 11, 12, 13, 14, 15, 16, 17, 18, 19, 20, 21, 22, 23, 24 or more hours, and/or 1, 2, 3, 4, 5, 6, 7, days or more. Moreover, administration may be through a time release or sustained release mechanism, implemented by formulation and/or mode of administration. Other delivery systems suitable include, but are not limited to, time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing nucleic acids are described in, for example, U.S. Pat. No. 5,075,109. Other examples include nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include, but are not limited to, erosional systems in which the RNA molecule is contained in a formulation within a matrix (for example, as described in U.S. Pat. Nos. 4,452,775, 4,675,189, 5,736, 152, 4,667,013, 4,748,034 and 5,239,660, which are hereby incorporated by reference), or diffusional systems in which an active component controls the release rate (for example, as described in U.S. Pat. Nos. 3,832,253, 3,854,480, 5,133, 974 and 5,407,686, which are hereby incorporated by reference). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the RNA molecules. In addition, a pump-based hardware delivery system may be used to deliver one or more embodiments. Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules. Compositions and methods can be used to enhance delivery of RNA molecules (see Shim and Kwon (2010), which is incorporated herein by reference, for review). Compositions and methods for enhanced delivery can provide for efficient delivery through the circulation, appropriate biodistribution, efficient cellular transport, efficient intracellular processing, and the like. Formulations and compositions can include, but are not limited to one or more of chemical modification of RNA molecules, incorporation of an RNA molecule or RNA precursors into a viral or non-viral vector, targeting of RNA molecule delivery, and/or coupling RNA molecules with a cellular delivery enhancer.

In certain aspects chemically modified RNA molecules can include, with or without the chemical modifications discussed above, the conjugation of an RNA molecule to a carrier molecule. In certain aspects the carrier molecule is a natural or synthetic polymer. For example, a carrier molecule can be cholesterol or an RNA aptamer and the like. A carrier molecule can be conjugated to the RNA molecules at the 5' and/or 3' end of either the active or passenger strand, or at an internal nucleotide position. The carrier can be conjugated the either strand of an RNA molecules.

In a further aspect one or two strands of the RNA molecule can be encoded by or delivered with a viral vector. A variety of viral vectors know in the art can be modified to express or carry an RNA molecule in a target cell, for example herpes simplex virus-1 or lentiviral vectors have been used to enhance the delivery of siRNA.

In a still further aspect, an RNA molecule can be associated with a non-viral vector. Non-viral vectors can be coupled to targeting and delivery enhancing moieties, such as antibodies, various polymers (e.g., PEG), fusogenic peptides, linkers, cell penetrating peptides and the like. Non-viral vectors include, but are not limited to liposomes and lipoplexes, polymers and peptides, synthetic particles and the like. In certain aspects a liposome or lipoplex has a neutral, negative or positive charge and can comprise cardolipin, anisamide-conjugated polyethylene glycol, dioleoyl phosphatidylcholine, or a variety of other neutral, anionic, or cationic lipids or lipid conjugates. siRNAs can be complexed to cationic polymers (e.g., polyethylenimine (PEI)), biodegradable cationic polysaccharide (e.g., chitosan), or cationic polypeptides (e.g., atelocollagen, poly lysine, and protamine).

In certain aspects RNA delivery can be enhanced by targeting the RNA to a cell. Targeting moieties can be conjugated to a variety of delivery compositions and provide selective or specific binding to a target cell(s). Targeting moieties can include, but are not limited to moieties that bind to cell surface receptors, cell specific extracellular polypeptide, saccharides or lipids, and the like. For example, small molecules such as folate, peptides such as RGD containing peptides, and antibodies such as antibodies to epidermal growth factor receptor can be used to target specific cell types.

In a further aspect, delivery can be enhanced by moieties that interact with cellular mechanisms and machinery, such as uptake and intracellular trafficking. In certain aspects cell penetrating peptides (CPPs) (e.g., TAT and MPG from HIV-1, penetratin, polyarginine can be coupled with an siRNA or a delivery vector to enhance delivery into a cell. Fusogenic peptides (e.g., endodomain derivatives of HIV-1 envelope (HGP) or influenza fusogenic peptide (diINF-7)) can also be used to enhance cellular delivery.

A variety of delivery systems such as cholesterol-siRNA, RNA aptamers-siRNA, adenoviral vector, lentiviral vector, stable nucleic acid lipid particle (SNALP), cardiolipin analog-based liposome, DSPE-polyethylene glycol-DOTAP-cholesterol liposome, hyaluronan-DPPE liposome, neutral DOPC liposome, atelocollagen, chitosan, polyethylenimine, poly-lysine, protamine, RGD-polyethylene glycol-polyethylenimine, HER-2 liposome with histidine-lysine peptide, HIV antibody-protamine, argine, oligoarginine (9R) conjugated water soluble lipopolymer (WSLP), oligoarginine (15R), TAT-PAMAM, cholesterol-MPG-8, DOPE-cationic liposome, GALA peptide-PEG-MMP-2 cleavable peptide-DOPE and the like have been used to enhance the delivery of siRNA.

The optimal therapeutic dose range for the miRNA mimics in cancer patients is contemplated to be 0.01-5.0 mg of miRNA per kg of patient body weight (mg/kg). In some embodiments, it is contemplated that about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0 mg of an RNA molecule, or any range derivable therein, may be formulated in a composition and/or administered to a patient. In some embodiments, a patient may be administered 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0 mg/kg of an RNA molecule, or any range derivable therein, per dose or regimen, which may be administered every 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 day(s), and/or 1, 2, 3, 4 weeks, and any range derivable therein.

Injections can be intravenous (IV), intraperitoneal (IP), intramuscular (IM), intratumoral (IT), intratracheally (for pulmonary delivery), intravitreal (for eye diseases), or subcutaneous, all of which have been determined to be effective as a delivery method for RNA molecules described herein. Several delivery technologies are specifically contemplated, including, but not limited to, neutral lipid emulsion, (NLE), atelocollagen, SNALP, DiLA, and cyclodextrin, which are discussed in further detail below.

Neutral lipid emulsions (NLEs) are a collection of formulations that combine a neutral lipid, oil, and emulsifier with a miRNA mimic to produce complexes that enable delivery of miRNAs to tumors and other tissues following intravenous (IV) injection. One such formulation combines 1,2-dioleoyl-sn-glycero-3-phosphocholine (DOPC), squalene, Polysorbate 20 (Tween-20), and ascorbic acid at a ratio of 1:2.6:53.4:0.1 (w/w). The NLE components are mixed in a solvent like chloroform and then the solvent is removed using a rotary evaporator leaving a viscous solution. A miRNA mimic dissolved in PBS is added at a ratio of 1:2 (w/w) to the DOPC. In certain embodiments, the ratio of RNA molecule to DOPC is about, at least about, or at most about 0.1:1, 0:2:1, 0.3:1, 0.4:1, 0.5:1, 0.6:1, 0.7:1, 0.8:1, 0.9:1, 1:1, 1:0.9, 1:0.8, 1:0.7, 1:0.6, 1:0.5, 1:0.4; 1:0.3, 1:0.2, 1:0.1 and any range derivable therein. Sonication produces particles+miRNA that can be IV injected at rates of approximately 0.01-1 mg/kg in humans. In certain embodiments, the amount of this formulation is provided to a patient in amounts of 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0 mg/kg to a patient per dose or regimen, which may be administered every 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 day(s), and/or 1, 2, 3, 4 weeks, and any range derivable therein.

Atelocollagen/miRNA complexes are prepared by mixing equal volumes of atelocollagen (0.1% in PBS at pH 7.4) (Koken Co., Ltd.; Tokyo, Japan) and miRNA solution (20 µM miRNA) and rotating the mixtures for 1 hr at 4° C. The resulting miRNA/atelocollagen complexes are diluted in PBS to a final concentration of atelocollagen of 0.05%. In certain embodiments, the final percentage concentration of atelocollagen is about, about at least, or about at most 0.01%, 0.02%, 0.03%, 0.04%, 0.05%, 0.06%, 0.07%, 0.08%, 0.09%, 0.10%, 0.11%, 0.10%, 0.11%, 0.12%, 0.13, 0.14%, 0.15%, 0.16%, 0.17%, 0.18%, 0.19%, 0.20%, and any range derivable therein.

SNALP categorizes a collection of formulations developed by Tekmira for the systemic delivery of nucleic acids. The most published formulation contains the lipids 3-N-[(qmethoxypoly(ethylene glycol)2000)carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio. The lipid formulation is mixed with siRNA/miRNA and forms particles using the ethanol dilution method (Jeffs 2005, which is hereby incorporated by reference). In some embodiments, the ratio of lipid to nucleic acid (w:w) is, is at least, or is at most about 0.001:1, 0.002:1, 0.003:1, 0.004:1, 0.005:1, 0.006:1, 0.007:1, 0.008:1, 0.009:1, 0.01:1, 0.02:1, 0.03:1, 0.04:1, 0.05:1, 0.06:1, 0.07:1, 0.08:1, 0.09:1, 0.1:1, 0.2:1, 0.3:1, 0.4:1, 0.5:1, 0.6:1, 0.7:1, 0.8:1, 0.9:1, 1:1, 1:0.9, 1:0.8, 1:0.7, 1:0.6, 1:0.5, 1:0.4, 1:0.3, 1:0.2, 1:0.1, 1:0.09, 1:0.08, 1:0.07, 1:0.06, 1:0.05, 1:0.04, 1:0.03, 1:0.02, 1:0.01, 1:0.009, 1:0.008, 1:0.007, 1:0.006, 1:0.005, 1:0.004, 1:0.003, 1:0.002, 1:0.001, or any range derivable therein.

Tekmira claims to achieve greater than 90% encapsulation efficiency. Particle sizes are approximately 110 nm.

DiLA$^2$ defines a group of a variety of formulations developed by Marina Biotech Inc. (Biothell, Wash., USA) for the systemic delivery of small, dsRNAs. One formulation combines C18:1-norArg-NH$_3$C1-C16, cholesteryl hemisuccinate (CHEMS, Anatrace, CH210), cholesterol (Anatrace CH200), and DMPE-PEG2k (Genzyme) at ratios of 50:28:20:2 (w/w). A small, dsRNA is combined with the lipid formulation at an RNA:lipid ratio of between 1.7:1 to 5:1 (w/w). In some embodiments, the RNA:lipid ratio is about, at least about, or at most about 0.001:1, 0.002:1, 0.003:1, 0.004:1, 0.005:1, 0.006:1, 0.007:1, 0.008:1, 0.009:1, 0.01:1, 0.02:1, 0.03:1, 0.04:1, 0.05:1, 0.06:1, 0.07:1, 0.08:1, 0.09:1, 0.1:1, 0.2:1, 0.3:1, 0.4:1, 0.5:1, 0.6:1, 0.7:1, 0.8:1, 0.9:1, 1:1, 1:0.9, 1:0.8, 1:0.7, 1:0.6, 1:0.5, 1:0.4, 1:0.3, 1:0.2, 1:0.1, 1:0.09, 1:0.08, 1:0.07, 1:0.06, 1:0.05, 1:0.04, 1:0.03, 1:0.02, 1:0.01, 1:0.009, 1:0.008, 1:0.007, 1:0.006, 1:0.005, 1:0.004, 1:0.003, 1:0.002, 1:0.001, and any range derivable therein. The two components are mixed via an impinging stream and incubated for 1 hour to produce stable particles with diameters of approximately 125 nm.

Pharmaceuticals, Inc. (Pasadena, Calif., USA) has developed a delivery platform called RONDEL™ that features cyclodextrin-based particles. Cyclodextrin polycations (CDP) are mixed with an adamantane-PEG5000 (AD-PEG) conjugate at a 1:1 AD:CDP (mol/mol) ratio (Hu Lieskovan 2005, which is hereby incorporated by reference). Transferrin-modified AD-PEG (AD PEG-transferrin) can be added at a 1:1,000 AD-PEG-transferrin:AD-PEG (w/w) ratio to provide a targeting moiety to improve delivery to cancer cells with elevated transferrin levels. The mixture is added to an equal volume of RNA molecule at a charge ratio (positive charges from CDP to negative charges from miRNA backbone) of 3:1 (+/−). In certain embodiments, the charge ratio between the mixture and RNA molecules is about, at least about, or at most about 5:1, 4:1, 3:1, 2:1, 1:1, 1:2, 1:3, 1:4, 1:5, or any range derivable therein, An equal volume of 10% (w/v) glucose in water is added to the resulting polyplexes to give a final polyplex formulation in 5% (w/v) glucose (D5W) suitable for injection.

In some embodiments, particles are used to deliver a therapeutic nucleic acid. In some embodiments, the particle size is about, at least about, or at most about 10, 20, 30, 40, 50, 60, 70, 80, 90, 110, 110, 120, 130, 140, 150, 160, 170, 180, 190, 200, 210, 220, 230, 240, 250 nm, or any range derivable therein.

A. Combination Treatments

In certain embodiments, the compositions and methods involve a therapeutic nucleic acid. These compositions can be used in combination with a second therapy to enhance the effect of the miRNA therapy, or increase the therapeutic effect of another therapy being employed. These compositions would be provided in a combined amount effective to achieve the desired effect, such as the killing of a cancer cell and/or the inhibition of cellular hyperproliferation. This process may involve contacting the cells with the therapeutic nucleic acid or second therapy at the same or different time. This may be achieved by contacting the cell with one or more compositions or pharmacological formulation that includes one or more of the agents, or by contacting the cell with two or more distinct compositions or formulations, wherein one composition provides (1) therapeutic nucleic acid; and/or (2) a second therapy. A second composition or method may be administered that includes a chemotherapy, radiotherapy, surgical therapy, immunotherapy or gene therapy.

It is contemplated that one may provide a patient with the miRNA therapy and the second therapy within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

In certain embodiments, a course of treatment will last 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 days or more. It is contemplated that one agent may be given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, any combination thereof, and another agent is given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, or any combination thereof. Within a single day (24-hour period), the patient may be given one or multiple administrations of the agent(s). Moreover, after a course of treatment, it is contemplated that there is a period of time at which no treatment is administered. This time period may last 1, 2, 3, 4, 5, 6, 7 days, and/or 1, 2, 3, 4, 5 weeks, and/or 1, 2, 3, 4, 5, 6, 7, 8, 9, 10, 11, 12 months or more, depending on the condition of the patient, such as their prognosis, strength, health, etc.

Administration of any compound or therapy of the present invention to a patient will follow general protocols for the administration of such compounds, taking into account the toxicity, if any, of the vector or any protein or other agent. Therefore, in some embodiments there is a step of monitoring toxicity that is attributable to combination therapy. It is expected that the treatment cycles would be repeated as necessary. It also is contemplated that various standard therapies, as well as surgical intervention, may be applied in combination with the described therapy.

In specific aspects, it is contemplated that a second therapy, such as chemotherapy, radiotherapy, immunotherapy, surgical therapy or other gene therapy, is employed in combination with the miRNA therapy, as described herein.

Examples of chemotherapeutic agents include alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1; dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; and pharmaceutically acceptable salts, acids or derivatives of any of the above.

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly. Radiotherapy may be used to treat localized solid tumors, such as cancers of the skin, tongue, larynx, brain, breast, or cervix. It can also be used to treat leukemia and lymphoma (cancers of the blood-forming cells and lymphatic system, respectively).

Radiation therapy used according to the present invention may include, but is not limited to, the use of γ-rays, X-rays, and/or the directed delivery of radioisotopes to tumor cells. Other forms of DNA damaging factors are also contemplated such as microwaves, proton beam irradiation (U.S. Pat. Nos. 5,760,395 and 4,870,287) and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. Radiotherapy may comprise the use of radiolabeled antibodies to deliver doses of radiation directly to the cancer site (radioimmunotherapy). Once injected into the body, the antibodies actively seek out the cancer cells, which are destroyed by the cell-killing (cytotoxic) action of the radiation. This approach can minimize the risk of radiation damage to healthy cells.

Stereotactic radio-surgery (gamma knife) for brain and other tumors does not use a knife, but very precisely targeted beams of gamma radiotherapy from hundreds of different angles. Only one session of radiotherapy, taking about four to five hours, is needed. For this treatment a specially made metal frame is attached to the head. Then, several scans and x-rays are carried out to find the precise area where the treatment is needed. During the radiotherapy for brain tumors, the patient lies with their head in a large helmet, which has hundreds of holes in it to allow the radiotherapy beams through. Related approaches permit positioning for the treatment of tumors in other areas of the body.

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor or disease cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or by using gene delivery in combination with a tumor suppressor such as MDA-7 has been shown to enhance anti-tumor effects (Ju et al., 2000). Moreover, antibodies against any of these compounds can be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739,169; Hui and Hashimoto, 1998; Christodoulides et al., 1998), cytokine therapy e.g., interferons α, β and γ; IL-1, GM-CSF and TNF (Bukowski et al., 1998; Davidson et al., 1998; Hellstrand et al., 1998) gene therapy e.g., TNF, IL-1, IL-2, p53 (Qin et al., 1998; Austin-Ward and Villaseca, 1998; U.S. Pat. Nos. 5,830,880 and 5,846,945) and monoclonal antibodies e.g., anti-ganglioside GM2, anti-HER-2, anti-p185; Pietras et al., 1998; Hanibuchi et al., 1998; U.S. Pat. No. 5,824,311). Herceptin (trastuzumab) is a chimeric (mouse-human) monoclonal antibody that blocks the HER2-neu receptor. It possesses anti-tumor activity and has been approved for use in the treatment of malignant tumors (Dillman, 1999). A non-limiting list of several known anti-cancer immunotherapeutic agents and their targets includes (Generic Name/Target) Cetuximab/EGFR, Panitumuma/EGFR, Trastuzumab/erbB2 receptor, Bevacizumab/VEGF, Alemtuzumab/CD52, Gemtuzumab ozogamicin/CD33, Rituximab/CD20, Tositumomab/CD20, Matuzumab/EGFR, Ibritumomab tiuxetan/CD20, Tositumomab/CD20, HuPAM4/MUC1, MORAb-009/Mesothelin, G250/carbonic anhydrase IX, mAb 8H9/8H9 antigen, M195/CD33, Ipilimumab/CTLA4, HuLuc63/CS1, Alemtuzumab/CD53, Epratuzumab/CD22, BC8/CD45, HuJ591/Prostate specific membrane antigen, hA20/CD20, Lexatumumab/TRAIL receptor-2, Pertuzumab/HER-2 receptor, Mik-beta-1/IL-2R, RAV12/RAAG12, SGN-30/CD30, AME-133v/CD20, HeFi-1/CD30, BMS-663513/CD137, Volociximab/anti-α5β1 integrin, GC1008/TGFβ, HCD122/CD40, Siplizumab/CD2, MORAb-003/Folate receptor alpha, CNTO 328/IL-6, MDX-060/CD30, Ofatumumab/CD20, and SGN-33/CD33. It is contemplated that one or more of these therapies may be employed with the miRNA therapies described herein.

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Effect of Nucleotide Modifications in Passenger or Active Strands of miR-124 on Anti-Cell Proliferation Activity The activity of a miRNA depends on both its ability to interact with proteins of the RNA-Induced Silencing Complex (RISC) and its ability to interact with an mRNA target through hybridization. To determine which nucleotides in a double-stranded miR-124 could be modified without disrupting miRNA activity within cells, we used a series of double-stranded miR-124 mimics with 2' oxygen-methyl (2'O-Me)-modified nucleotides incorporated at two adjacent positions on the active strand or on the passenger strand of the double-stranded miRNA (Table 1). In addition to the 2'O-Me modifications, each passenger strand had a 5'-end modification consisting of an amino C6 nucleotide (primary amine group attached to a 6-carbon spacer) attached to the 5' terminal $PO_4^-$ group.

TABLE 1

Sequence and modification patterns of miR-124 mimics.
Nucleotide locations of 2'O-Me-modified nucleotides are indicated as bold, italicized, and underlined.

| Strand | Sequence (SEQ ID NO: 4) | Position of 2'O-Me-Modified Nucleotides | 5' Modification |
|---|---|---|---|
| Passenger | UGGCAUUCACCGCGUGCCUUAA | None | 5'-amino C6 |
| Passenger | *UG*GCAUUCACCGCGUGCCUUAA | 1,2 | 5'-amino C6 |
| Passenger | UG*GC*AUUCACCGCGUGCCUUAA | 3,4 | 5'-amino C6 |
| Passenger | UGGC*AU*UCACCGCGUGCCUUAA | 5,6 | 5'-amino C6 |
| Passenger | UGGCAU*UC*ACCGCGUGCCUUAA | 7,8 | 5'-amino C6 |
| Passenger | UGGCAUUC*AC*CGCGUGCCUUAA | 9,10 | 5'-amino C6 |
| Passenger | UGGCAUUCAC*CG*CGUGCCUUAA | 11,12 | 5'-amino C6 |
| Passenger | UGGCAUUCACCG*CG*UGCCUUAA | 13,14 | 5'-amino C6 |
| Passenger | UGGCAUUCACCGCG*UG*CCUUAA | 15,16 | 5'-amino C6 |
| Passenger | UGGCAUUCACCGCGUG*CC*UUAA | 17,18 | 5'-amino C6 |
| Passenger | UGGCAUUCACCGCGUGCC*UU*AA | 19,20 | 5'-amino C6 |
| Passenger | *UG*GCAUUCACCGCGUGCCUU*AA* | 1,2,21,22 | 5'-amino C6 |
| Passenger | *UGG*CAUUCACCGCGUGCCU*UAA* | 1,2,3,20,21,22 | 5'-amino C6 |
| Passenger | U*GG*CA*UU*CA*CC*GC*GU*GC*CU*UAA | 2,3,6,7,10,11,14,15,18,19 | 5'-amino C6 |
| Passenger | UGG*CA*UU*CA*CC*GC*GU*GC*CU*UA*A | 4,5,8,9,12,13,16,17,20,21 | 5'-amino C6 |

| Strand | Sequence (SEQ ID NO: 2) | Position of 2'O-Me-Modified Nucleotides | 5' Modification |
|---|---|---|---|
| Active | UUAAGGCACGCGGUGAAUGCCA | None | None |
| Active | *UU*AAGGCACGCGGUGAAUGCCA | 1,2 | None |
| Active | UU*AA*GGCACGCGGUGAAUGCCA | 3,4 | None |
| Active | UUAA*GG*CACGCGGUGAAUGCCA | 5,6 | None |
| Active | UUAAGG*CA*CGCGGUGAAUGCCA | 7,8 | None |
| Active | UUAAGGCA*CG*CGGUGAAUGCCA | 9,10 | None |
| Active | UUAAGGCACG*CG*GUGAAUGCCA | 11,12 | None |
| Active | UUAAGGCACGCG*GU*GAAUGCCA | 13,14 | None |
| Active | UUAAGGCACGCGGU*GA*AUGCCA | 15,16 | None |
| Active | UUAAGGCACGCGGUGA*AU*GCCA | 17,18 | None |
| Active | UUAAGGCACGCGGUGAAU*GC*CA | 19,20 | None |
| Active | *UU*AAGGCACGCGGUGAAUG*CA* | 1,2,21,22 | None |
| Active | *UUA*AGGCACGCGGUGAAU*GCCA* | 1,2,3,20,21,22 | None |
| Active | U*UA*AG*GC*AC*GC*GG*UG*AA*UG*CCA | 2,3,6,7,10,11,14,15,18,19 | None |
| Active | UU*AA*GG*CA*CG*CG*GU*GA*AU*GC*CA | 3,4,7,8,11,12,15,16,19,20 | None |

The inventors examined the effects of the oligonucleotide modifications on the activities of the miR-124 mimics. Synthetic, passenger strand oligonucleotide having a 5'-amino C6 modification and no 2'O-Me modifications was annealed to each of the synthetic, modified active strand oligonucleotides (Table 1). Synthetic, unmodified active strand oligonucleotide was annealed to each of the synthetic, modified passenger strand oligonucleotides (Table 1.) The lung cancer cell line (H460) was reverse transfected with the resultant double stranded oligonucleotides or with a negative control miRNA (Life Technologies, Inc./Ambion, Inc; Austin, Tex., USA; cat. no. AM17103) at final concentrations of 30 nM. Cell lines were transiently transfected using Lipofectamine 2000 (Life Technologies, Inc./Invitrogen Corp., Carlsbad, Calif., USA) according to the manufacturer's recommendations using the following parameters: 5,000 cells per well in a 96 well plate, 0.1-0.2 µl of Lipofectamine 2000 (cell line specific optimized), in 100 µl total volume of media. Cell viability assays were performed using the alamarBlue® reagent (Invitrogen Corp.; Carlsbad, Calif., USA; cat. no. DAL1100) according to the manufacturer's protocol at days 3, 4, and 7 following transfection. A fluorescent plate reader was used to measure accumulation of resorufin (560 nm excitation, 590 nm emission) which is the reduced substrate of alamarBlue®. Resorufin accumulation is indicative of the number of viable cells per well. The relative number of proliferating cells for each cell population transfected with a double-stranded miR-124 having 2'O-Me modifications was calculated by dividing the fluorescence of cells transfected with the unmodified miR-124 mimics by the fluorescence of cells transfected with a double-stranded miR-124s and multiplying the result by 100. Relative anti-proliferation values are shown in Table 2.

TABLE 2

Effect of 2'-O Me-modified nucleotides in miR-124 on proliferation of H460 lung cancer cells. Anti-cell proliferative activity of a synthetic, double-stranded miR-124 having no 2'O—Me modifications was set at 100%. Percentage anti-cell proliferation values greater than 100 indicate anti-proliferative activity that is higher than that of the unmodified miR-124 control. The indicated modifications were in the passenger strand or active strand only. All passenger strands had a 5'-amino C6 modification.

| 2'O—Me-Modified Nucleotide Positions | Percentage Anti-Cell Proliferation Activity | |
|---|---|---|
| Relative to SEQ ID NO: 4 (passenger) or NO: 2 (active) | Modification in Passenger Strand | Modification in Active Strand |
| 1, 2 | 111.31 | 27.75 |
| 3, 4 | 105.20 | 43.13 |
| 5, 6 | 99.32 | 94.45 |
| 7, 8 | 41.47 | 105.36 |
| 9, 10 | 35.86 | 60.84 |
| 11, 12 | 75.34 | 91.51 |
| 13, 14 | 91.39 | 53.85 |
| 15, 16 | 90.69 | 48.46 |
| 17, 18 | 110.14 | 84.37 |
| 19, 20 | 89.81 | 66.28 |
| 1, 2, 21, 22 | 109.48 | 26.28 |
| 1, 2, 3, 20, 21, 22 | 119.92 | 25.91 |

As shown in Table 2, 2'O-Me modifications in the passenger strand at positions 1+2; 3+4; 17+18; 1+2+21+22; and 1+2+3+20+21+22 and in the active strand at positions 7+8 resulted in increased anti-proliferative activity over that observed for the unmodified control miR-124. 2'O-Me modifications in the active strand at positions 1+2; 3+4; 9+10; 13+14; 15+16; 19+20; 1+2+21+22; and 1+2+3+20+21+22 and in the passenger strand at positions 7+8; 9+10; and 11+12 resulted in substantially impaired anti-proliferative activity when compared to the miR-124 mimic having no 2'-O Me modifications. 2'O-Me modifications at positions 5+6; 11+12; and 17+18 of the active strand and at positions 5+6; 13+14; 15+16; and 19+20 of the passenger strand had little detrimental effect on anti-proliferative activity.

Example 2

Effect of Combined Nucleotide Modifications in Passenger and Active Strands of miR-124 on Anti-Cell Proliferation Activity The inventors evaluated the anti-cell proliferation activity of miR-124 mimics having modified nucleotides in both the passenger and active strands. Various modified passenger and active strand oligonucleotides were annealed to form miR-124 mimics with modifications on both strands. Lung cancer (H460) and liver cancer (C3A) cell lines were reverse transfected with the various mimics as well as with a negative control miRNA (Ambion, cat. no. AM17103) at final concentrations of 30 nM. Lipofectamine 2000 (Invitrogen) was used according to the manufacturer's recommendations using the following parameters: 5,000 cells per well in a 96 well plate, 0.1-0.2 µl of Lipofectamine 2000 (cell line optimized), in 100 µl total volume of media. An alamarBlue® assay (Invitrogen, cat. no. DAL1100) was performed on the cells according to the manufacturer's protocol, on day six following transfection. A fluorescent plate reader was used to measure accumulation of resorufin (560 nm excitation, 590 nm emission) which is the reduced substrate in alamarBlue®. Resorufin fluorescence correlates with the number of viable cells per well. The relative number of proliferating cells for each transfected cell population was calculated by dividing the fluorescence of cells transfected with the unmodified miR-124 mimic by the fluorescence of cells transfected with the double-stranded 2'O-Me-modified miR-124 mimics and multiplying the result by 100. Results are shown in Table 3.

TABLE 3

Effects of nucleotide modifications in a double-stranded miR-124 mimic on anti-cell proliferation activity of lung cancer cells (H460) and liver cancer cells (C3A). Values for percentage of anti-cell proliferation activity that are greater than 100 indicate anti-proliferative activity that is higher with modified miR-124 mimics than that observed with unmodified miR-124. The indicated modifications were in the passenger strand, active strand, or both strands. All passenger strands had a 5'-amino C6 modification.

| Active Strand 2'O—Me-Modified Nucleotide Positions | Passenger Strand 2'O—Me-Modified Nucleotide Positions | Percentage Anti-Cell Proliferation Activity |
|---|---|---|
| None | None | 100 |
| None | 1, 2, 21, 22 | 125 |
| None | 1, 2, 3, 20, 21, 22 | 121 |
| 5, 6 | None | 98 |
| 5, 6 | 1, 2, 21, 22 | 113 |
| 5, 6 | 1, 2, 3, 20, 21, 22 | 106 |
| 7, 8 | None | 106 |
| 7, 8 | 1, 2, 21, 22 | 162 |
| 7, 8 | 1, 2, 3, 20, 21, 22 | 256 |
| 17, 18 | None | 95 |
| 17, 18 | 1, 2, 21, 22 | 125 |
| 17, 18 | 1, 2, 3, 20, 21, 22 | 134 |
| 1, 2, 3, 20, 21, 22 | None | 59 |
| 1, 2, 3, 20, 21, 22 | 1, 2, 21, 22 | 57 |
| 1, 2, 3, 20, 21, 22 | 1, 2, 3, 20, 21, 22 | 59 |

As shown in Table 3 (involving an active strand with SEQ ID NO:2 and a passenger strand with SEQ ID NO:4), most miR-124 mimics having 2'O-Me modifications at positions 5,6; 7,8; or 17,18 in the active strand have higher anti-cell proliferation activity than does the unmodified miR-124 mimic, regardless of the number of modifications in the passenger strand. Several mimics having modifications in both active and passenger strands have significantly greater anti-cell proliferation activities than would be expected based upon data from mimics having only a single modified strand which suggests synergistic effects of the modifications. For instance, the 7+8 2'O-Me-modified active strand combined with the 1+2+21+22 or with the 1+2+3+20+21+22 2'OMe-modified passenger strands are considerably more anti-proliferative than mimics having only one modified strand. Likewise, the 17+18 2'O-Me-modified active strand has significantly more activity than expected when combined with the 1+2+3+20+21+22 2'O-Me-modified passenger strand. These data suggest that 2'O-Me modifications not only enhance the anti-proliferative activities of miR-124 mimics but that certain combinations of modifications can be applied to significantly enhance the activities of a miR-124 mimic.

Example 3

Nucleotide Modifications in Both Active and Passenger Strands Contribute to Stability of miRNA Mimics Because a 2'OH is required for ribonucleases to cleave RNA molecules, incorporating 2'-modified nucleotides into RNA molecules can make them more resistant to nuclease digestion. The inventors used an in vitro stability assay and purified RNase A (Ambion, cat. no. AM2270) to compare the stabilities of the modified and unmodified miR-124 mimics.

miR-124 mimics were prepared by hybridizing complementary oligonucleotides having 2'O-Me-modified nucleotides at various positions and incubating the hybrids with 720 U of RNaseA at 37° C. for 30 min. Following the 30 min incubation dithiothreitol (DTT) was added to a final concentration of 10 mM and the mixture was heated at 60° C. for 10 min to inactivate RNase activity. RNA was reverse transcribed with MMLV-RT (Invitrogen, cat. no. 28025-021) using the hsa-miR-124 TaqMan® MicroRNA assay RT primer (Applied Biosystems Inc.; cat. no. 4427975, assay ID 000446). qRT-PCR was performed on the cDNA using the TaqMan® MicroRNA assay with a primer specific for hsa-miR-124 and Platinum Taq Polymerase (Invitrogen, cat. no. 10966-083), in a 7900HT Fast Real-Time PCR System (Applied Biosystems). Table 4 shows the effects of nucleotide modifications on the stability of various miR-124 mimics.

TABLE 4

Effects of strand modifications on the stability of double-stranded miR-124 mimics following incubation with RNase A. Passenger and active strand sequences are shown. Bold and italicized underlined letters indicate 2'O-Me-modified nucleotides. The active and passenger strands within each row were hybridized and incubated in an RNase A solution. The relative percentages of double-stranded mimics remaining after RNase A treatment were calculated by determining the percentage of double-stranded mimics remaining and dividing by the percentage of the unmodified double stranded mimic remaining. Values greater than 1.00 indicate modified mimics having more stability than the unmodified mimic. A value of 100 in the table would indicate that a modified miR-124 mimic was 100 times more stable than the unmodified miR-124 mimic. A-ID, active strand ID number; P-ID, passenger strand ID number. All passenger strands had a 5'-amino C6 modification.

| P-ID | Passenger (SEQ ID NO: 4) | Active (SEQ ID NO: 2) | A-ID | Relative amount of ds miR-124 mimic after RNase treatment |
|---|---|---|---|---|
| 101 | UGGCAUUCACCGCGU GCCUUAA | UUAAGG*CA*CGCGGUGA AUGCCA | KK22 | 1.29 |
| 102 | *UGG*CAUUCACCGCGU GCCU*UAA* | UUAAGG*CA*CGCGGUGA AUGCCA | KK22 | 1.54 |
| 107 | *UGGC*AUUCACCGCGU GCCU*UAA* | UUAAGG*CA*CGCGGUGA AUGCCA | KK22 | 2.02 |
| 108 | *UGGCAU*UCACCGCGU GCCU*UAA* | UUAAGG*CA*CGCGGUGA AUGCCA | KK22 | 1.04 |
| 101 | UGGCAUUCACCGCGU GCCUUAA | UUAAGGCACGCGGUGA AUGCCA | 111 | 1.00 |
| 102 | *UGG*CAUUCACCGCGU GCCU*UAA* | UUAAGGCACGCGGUGA AUGCCA | 111 | 9.74 |
| 107 | *UGGC*AUUCACCGCGU GCCU*UAA* | UUAAGGCACGCGGUGA AUGCCA | 111 | 21.45 |
| 108 | *UGGCAU*UCACCGCGU GCCU*UAA* | UUAAGGCACGCGGUGA AUGCCA | 111 | 9.12 |
| 101 | UGGCAUUCACCGCGU GCCUUAA | UUAAGG*CA*CGCGGUGA *AU*GCCA | 113 | 8.26 |
| 102 | *UGG*CAUUCACCGCGU GCCU*UAA* | UUAAGG*CA*CGCGGUGA *AU*GCCA | 113 | 9.53 |

TABLE 4-continued

Effects of strand modifications on the stability of double-stranded miR-124 mimics following incubation with RNase A. Passenger and active strand sequences are shown. Bold and italicized underlined letters indicate 2'-O-Me-modified nucleotides. The active and passenger strands within each row were hybridized and incubated in an RNase A solution. The relative percentages of double-stranded mimics remaining after RNase A treatment were calculated by determining the percentage of double-stranded mimics remaining and dividing by the percentage of the unmodified double stranded mimic remaining. Values greater than 1.00 indicate modified mimics having more stability than the unmodified mimic. A value of 100 in the table would indicate that a modified miR-124 mimic was 100 times more stable than the unmodified miR-124 mimic. A-ID, active strand ID number; P-ID, passenger strand ID number. All passenger strands had a 5'-amino C6 modification.

| P-ID | Passenger (SEQ ID NO: 4) | Active (SEQ ID NO: 2) | A-ID | Relative amount of ds miR-124 mimic after RNase treatment |
|---|---|---|---|---|
| 107 | *UGGC*AUUCACCGCGU GCCU*UAA* | UUAAGG*CA*CGCGGUGA *AU*GCCA | 113 | 4.74 |
| 108 | *UGGCAU*UCACCGCGU GCCU*UAA* | UUAAGG*CA*CACGGUGA *AU*GCCA | 113 | 36.90 |
| 101 | UGGCAUUCACCGCGU GCCUUAA | UUAAGG*CCA*CG*CG*GUGA AUGCCA | 117 | 35.73 |
| 102 | *UGG*CAUUCACCGCGU GCCU*UAA* | UUAAGG*CA*CG*CG*GUGA AUGCCA | 117 | 22.00 |
| 107 | *UGGC*AUUCACCGCGU GCCU*UAA* | UUAAGG*CA*CG*CG*GUGA AUGCCA | 117 | 24.12 |
| 108 | *UGGCAU*UCACCGCGU GCCU*UAA* | UUAAGG*CA*CG*CG*GUGA AUGCCA | 117 | 12.58 |
| 101 | UGGCAUUCACCGCGU GCCUUAA | UUAAGG*CACGCG*GUGA AUGCCA | 119 | 35.32 |
| 102 | *UGG*CAUUCACCGCGU GCCU*UAA* | UUAAGG*CACGCG*GUGA AUGCCA | 119 | 129.42 |
| 107 | *UGGC*UCACCGCGU GCCU*UAA* | UUAAGG*CACGCG*GUGA AUGCCA | 119 | 112.79 |
| 108 | *UGGCAU*UCACCGCGU GCCU*UAA* | UUAAGG*CACGCG*GUGA AUGCCA | 119 | 48.06 |
| 101 | UGGCAUUCACCGCGU GCCUUAA | UUAAGG*CACGCG*GUGA *AU*GCCA | 120 | 11.03 |
| 102 | *UGG*CAUUCACCGCGU GCCU*UGG* | UUAAGG*CACGCG*GUGA *AU*GCCA | 120 | 3.11 |
| 107 | *UGG*CAUUCACCGCGU GCCUU*UAA* | UUAAGG*CACGCG*GUGA *AU*GCCA | 120 | 16.52 |
| 108 | *UGGCAU*UCACCGCGU GCCU*UAA* | UUAAGG*CACGCG*GUGA *AU*GCCA | 120 | 30.30 |

The mimic having active and passenger strand combination A119/P102 is over 125 times more stable than the unmodified mimic. Heightened stability of mimics can profoundly improve pharmacodynamic properties during therapy with miRNAs.

In the absence of these data, one might predict that the mimic with the most 2'-O-Me-modified nucleotides would be the most stable, because it has the lowest number of nuclease-sensitive sites. Surprisingly, in our assay, the most modified mimic (A120/P108) was not observed to be the most stable mimic. These data suggest that simply counting the number of 2'-O-Me modifications is not an accurate reflection of or a predictable way for determining stability of modified double-stranded miR-124 mimics.

Example 4

Nucleotide Modifications in Both Active and Passenger Strands Contribute to Activity of miRNA Mimics The anti-proliferative activities of three of the most nuclease-resistant miR-124 mimics were evaluated and compared to the miR-124 mimic with no 2'-O-Me modifications. Lung cancer cells (H460) were reverse transfected with the four different double stranded miR-124 mimics and a negative control miRNA (Ambion, cat. no. AM17103) at final concentrations of 1, 3, and 10 nM. Lipofectamine 2000 (Invitrogen) was used according to the manufacturer's recommendations using the following parameters: 5,000 cells per well in a 96 well plate, 0.1-0.2 μl of Lipofectamine 2000 (cell line specific optimized), in 100 μl total volume of media. An alamarBlue® assay (Invitrogen, cat. no. DAL1100) was performed on the cells at 3 days post-transfection, according to the manufacturer's protocol. A fluorescent plate reader was used to measure accumulation of resorufin (560 nm excitation, 590 nm emission) which is the reduced substrate in alamarBlue®. Resorufin fluorescence correlates with the number of viable cells per well. The relative percentage of viable cells for each transfected cell population was calculated by dividing the fluorescence from cells transfected with a given concentration of the miR-124 mimic by the fluorescence from cells transfected with the same concentration of the negative control miRNA and multiplying the result by 100. Values less than 100% indicate that the miR-124 mimic reduced the number of viable cells in the population relative to cell populations that were transfected with the negative control miRNA. The results are shown in Table 5.

TABLE 5

Effects of 2'-O Me modifications on the anti-cell proliferation activity of miR-124 mimics following transfection of H460 lung cancer cells. Passenger and active strand sequences are shown. Bold and italicized and underlined letters indicate 2'O-Me-modified nucleotides. The active and passenger strands within each row were hybridized and transfected into H460 cells at the concentrations shown. A-ID, active strand ID number; P-ID, passenger strand ID number. Percentage viable cells is the percentage of cells that remain viable following transfection with the miR-124 mimic. Values for the negative control miRNA were set a 100%. All passenger strands had a 5'-amino C6 modification.

| P-ID | Passenger Strand | Active Strand | A-ID | Percentage Viable Cells | | |
|---|---|---|---|---|---|---|
| | | | | 1 nM | 3 nM | 10 nM |
| 101 | UGGCAUUCACCGCGUGC CUUAA | UUAAGGCACGCGGUGAA UGCCA | 111 | 72% | 47% | 41% |
| 102 | *UGG*CAUUCACCGCGUGC CU*UAA* | UUAAGG*CACGCG*GUGAA UGCCA | 119 | 49% | 36% | 29% |
| 107 | *UGGC*AUUCACCGCGUGC CU*UAA* | UUAAGG*CACGCG*GUGAA UGCCA | 119 | 48% | 35% | 28% |
| 108 | *UGGCAU*UCACCGCGUGC CU*UAA* | UUAAGG*CA*CGCGGUGA*A* *U*GCCA | 113 | 59% | 38% | 29% |

Mimic pairs P102/A119, P107/A119, and P108/A113 each demonstrated enhanced nuclease-stability (Table 4) and also exhibited increased anti-proliferative activity (Table 5). The modified miR-124 mimics have similar anti-proliferative activities as the standard miR-124 mimic effect when used at one-third the dose, indicating that the chosen modified miR-124a mimics are approximately three times more active than the standard miR-124 mimic. The three modified mimics have considerably improved anti-cell proliferation activities (Table 5) and nuclease stabilities (Table 4) than those observed for the non 2'-O Me-modified mimic.

Example 5

Gene Regulation by Modified miR-124 Mimics miRNAs function as guide sequences for the RNA-Induced Silencing Complex (RISC) regulation of mRNA transcription. After entering the RISC, a miRNA mimic can alter the mRNA transcription profiles of transfected cells by: (1) inducing RISC to cleave an mRNA that is bound to the miRNA, (2) altering the half-life of a bound mRNA by preventing it from interacting with ribosomes, and/or (3) causing changes in amounts of mRNAs that are regulated by genes that themselves are regulated by the miRNA mimic.

To address whether the modified miR-124 mimics have the same effects on mRNA expression that an unmodified miR-124 mimic has, we used mRNA arrays to profile gene transcription in H460 lung cancer cells transfected with one of two different negative control miRNAs (Ambion, cat. no. AM17111; Ambion, cat. no. AM17103), an unmodified miR-124 mimic, or three different modified miR-124 mimics (P102/A119, P107/A119, and P108/A113). miRNA mimics at 1 nm, 3 nM, or 10 nM were complexed with 0.2 μl of Lipofectamine 2000 and added to H460 cells at 5,000 per well in a 96 well plate, in 100 μl total volume of RPMI media. Cells were harvested at 3 days post transfection, and total RNA was extracted using the mirVana™ PARIS™ Kit (Ambion, cat. no. AM1556) following the manufacturer's recommended protocol.

mRNA array analyses were performed by Asuragen, Inc. (Austin, Tex., USA), according to the company's standard operating procedures. Using the MessageAmp™ II-96 aRNA Amplification Kit (Ambion, cat. no. 1819), 200 ng of input total RNA was labeled with biotin. cRNA yields were quantified using an Agilent 2100 Bioanalyzer capillary electrophoresis instrument (Agilent Technologies, Inc.). Labeled target was hybridized to Affymetrix mRNA arrays (Human HG-U133A 2.0 arrays) using the manufacturer's recommendations and the following parameters. Hybridizations were carried out at 45'C for 16 hr in an Affymetrix Model 640 hybridization oven. Arrays were washed and stained on an Affymetrix FS450 Fluidics station, running the wash script Midi_euk2v3_450. The arrays were scanned on an Affymetrix GeneChip Scanner 3000. Summaries of the image signal data, group mean values, p-values with significance flags, log ratios and gene annotations for every gene on the array were generated using the Affymetrix Statistical Algorithm MAS 5.0 (GCOS v1.3). Data were reported containing the Affymetrix data and result files (cabinet file) and containing the primary image and processed cell intensities of the arrays (.cel).

The mRNA array profiles for the various samples were compared to determine their similarities. Pearson product-moment correlation coefficients between the samples (complete probe set) were calculated and are shown in Tables 6, 7, and 8. Correlation coefficients for all samples were observed to be greater than 0.98.

TABLE 6

Pearson product-moment correlation coefficients following array analysis of gene expression after transfection of lung cancer cells with 1 nM of the indicated miRNA mimic. Sequences and 2'-O Me modifications of the P—passenger and A—active strands are shown in Table 5. All passenger strands had a 5'-amino C6 modification.

| P101/A111 | P102/A119 | P107/A119 | P108/A113 | |
|---|---|---|---|---|
| 1.000 | 0.998 | 0.996 | 0.997 | P101/A111 |
| | 1.000 | 0.997 | 0.998 | P102/A119 |
| | | 1.000 | 0.998 | P107/A119 |
| | | | 1.000 | P108/A113 |

TABLE 7

Pearson product-moment correlation coefficients following array analysis of gene expression after transfection of lung cancer cells with 3 nM of the indicated miRNA mimic. Sequences and 2'-O Me modifications of the P—passenger and A—active strands are shown in Table 5. All passenger strands had a 5'-amino C6 modification.

| P101/A111 | P102/A119 | P107/A119 | P108/A113 | |
|---|---|---|---|---|
| 1.000 | 0.995 | 0.991 | 0.988 | P101/A111 |
| | 1.000 | 0.996 | 0.995 | P102/A119 |
| | | 1.000 | 0.996 | P107/A119 |
| | | | 1.000 | P108/A113 |

TABLE 8

Pearson product-moment correlation coefficients following array analysis of gene expression after transfection of lung cancer cells with 10 nM of the indicated miRNA mimic. Sequences and 2'-O Me modifications of the P—passenger and A—active strands are shown in Table 5. All passenger strands had a 5'-amino C6 modification.

| P101/A111 | P102/A119 | P107/A119 | P108/A113 | |
|---|---|---|---|---|
| 1.000 | 0.987 | 0.985 | 0.980 | P101/A111 |
| | 1.000 | 0.992 | 0.990 | P102/A119 |
| | | 1.000 | 0.997 | P107/A119 |
| | | | 1.000 | P108/A113 |

Limiting analysis to those mRNAs whose expression levels were altered at least two-fold by any of the miR-124 mimics used, the strongest correlations were observed between cells transfected with 3 nM of the 2'-O Me modified miR-124 mimics and 10 nM of the unmodified miR-124 mimic (Table 9). This is unsurprising given the approximately three-fold greater activities for the 2'-O Me-modified miR-124 mimics than the miR-124 mimic with no 2'-O Me modifications that we observed in Example 4. These data reveal that the target specificities of the three modified miR-124 mimics are the same as the unmodified miR-124 mimic.

TABLE 9

Pearson product-moment correlation coefficients following array analysis of gene expression altered at least two-fold after transfection of lung cancer cells with 10 nM of the miR-124 mimic having no modified nucleotides (P101/A111) and 3 nM of other miR-124 mimics (P102/A119, P107/A119, P108/A113). Sequences and 2'-O Me modifications of the P—passenger and A—active strands are shown in Table 5.. All passenger strands had a 5'-amino C6 modification.

| P101/A111 | P102/A119 | P107/A119 | P108/A113 | |
|---|---|---|---|---|
| 1.000 | 0.949 | 0.939 | 0.944 | P101/A111 |
| | 1.000 | 0.981 | 0.968 | P102/A119 |
| | | 1.000 | 0.979 | P107/A119 |
| | | | 1.000 | P108/A113 |

In addition to global expression profiles, we compared the activity of 2'O-Me-modified and unmodified miR-124 mimics on known miR-124 target genes. Array data revealed that levels of two direct mRNA targets of miR-124, VAMP3 and ATP6VOE1, were significantly reduced in all of the miR-124-treated cell populations when compared to cells transfected with a negative control miRNA (Table 10).

TABLE 10

VAMP3 or ATP6VOE1 mRNA levels following transfection of H460 cells with the indicated miR-124 mimic at a concentration of 1 nM, 3 nM, or 10 nM. Values represent percentage expression compared to that observed following transfection of cells with a negative control miRNA (100%). Sequences and 2'-O Me modifications of the P-passenger and A-active strands are shown in Table 5. All passenger strands had a 5'-amino C6 modification.

| | Percentage Expression vs. Negative Control miRNA | | | | | |
|---|---|---|---|---|---|---|
| | VAMP3 | | | ATP6VOE1 | | |
| miR-124 Mimic | 1 nM | 3 nM | 10 nM | 1 nM | 3 nM | 10 nM |
| P101/A111 | 69.02 | 74.35 | 33.96 | 81.16 | 61.31 | 44.55 |
| P102/A119 | 72.44 | 34.75 | 14.85 | 76.27 | 47.62 | 38.36 |
| P107/A119 | 76.79 | 43.08 | 9.30 | 72.72 | 43.48 | 32.18 |
| P108/A113 | 56.48 | 28.54 | 11.11 | 72.30 | 44.90 | 30.20 |

Example 6

Pharmacokinetic Properties of 2'O-Me-Modified miR-124 Mimics

Improved circulation time and target cell uptake can enhance the effectiveness of treatment with therapeutic oligonucleotides. To determine if the 2'-O Me-modified miR-124 mimics had improved pharmacokinetic properties relative to the unmodified miR-124 mimic, mice having H460 lung cancer xenografts were repeatedly dosed with miR-124 mimics and then evaluated for circulating and tissue-associated levels of miR-124.

Lung tumor xenografts were induced in NOD/SCID mice by injecting $3 \times 10^6$ human lung cancer cells (H460) in 50% matrigel into the flanks of the mice (n=7). The mice were checked periodically for firm nodules at the injection sites to determine the time at which tumors had grown to ~100 mm$^3$. Tumors were detected at day 11, whereupon tail vein injections with either the unmodified mimic or one of the three 2'-O Me-modified mimics were initiated at a rate of 20 μg mimic per animal per dose. Doses were repeated once every two days for two weeks. Animals were sacrificed 10 or 60 minutes following the final dose given. Blood, tumors, and livers were recovered from each animal. RNA was isolated from each of the samples using the mirVana™ PARIS™ Kit (Ambion, cat no AM1556).

miR-124 levels in blood, tumor, and liver samples were measured by qRT-PCR 10 and 60 minutes after tail vein injections of unmodified (P101/A111) or modified mimics (P102/A119, P107/A119, P108/A113) of miR-124. miRNA levels were measured using a TaqMan® MicroRNA Assay (Applied Biosystems; Foster City, Calif., USA). To enable sample normalization, levels of miR-103, miR-191, and miR-24 were also measured by qRT-PCR using TaqMan® MicroRNA Assays. Prior to starting the reverse transcription (RT) reaction, 10 ng of total RNA was mixed with 0.5 μl of RT primer and enough water to bring the total volume to 5 μl. The RNA/primer mix was heated to 90° C. for 1 minute then transferred to 4° C. Water (2.85 μl), 10×RT buffer (1 μl), 2.5 mM dNTPs (1 μl), RIP (0.1 μl of 40 U/μl), and MMLV-RT (0.05 μl of 200 U/μl) were added to each tube on ice. RT reactions were incubated in a 384-well GeneAmp® PCR System 9700 (Applied Biosystems) at 4° C. for 30 minutes, then at 16° C. for 30 minutes, then at 42° C. for 30 minutes, then at 85° C. for 5 minutes.

PCR components (Table 11) were assembled on ice prior to the addition of cDNA (2 μl) from the RT reaction. Reactions were incubated in an ABI PRISM™ 7900HT Fast Real-Time PCR system (Applied Biosystems) at 95° C. for 1 minute, then for 50 cycles at 95° C. for 5 seconds and 60° C. for 30 seconds. Results were analyzed with the 7900HT Fast Real-Time PCR system SDS V2.3 software (Applied Biosystems).

TABLE 11

PCR components. All reaction components were as provided by the manufacturer (Applied Biosystems; Foster City, CA, USA) unless otherwise specified.

| Component | μl per 15 μl rxn | Final Concentration |
| --- | --- | --- |
| Nuclease-free water | 7.8 | |
| MgCl$_2$ (50 mM) (Invitrogen Corp.; Carlsbad, CA, USA) | 1.5 | 5 mM |
| 10X Platinum PCR Buffer, Minus Mg (Invitrogen Corp.; Carlsbad, CA, USA) | 1.5 | 1 X |
| dNTP mix (2.5 mM each) (Ambion, Inc.; Austin, TX USA) | 1.5 | 0.25 mM each |
| 20X TaqMan Assay Buffer | 0.3 | 0.4 X |
| 50X ROX Passive Reference | 0.3 | 1 X |
| Platinum ® Taq DNA Polymerase (5 U/μl) (Invitrogen) | 0.1 | 0.033 U/μl |
| cDNA from RT reaction | 2.0 | |

The qRT-PCR data from miR-103, miR-191, and miR-24 were initially assessed to identify samples with too little miRNA to accurately measure. These samples were not subjected to additional analysis. Samples in which the miR-124 Ct value exceeded 40 were also eliminated. The geometric mean of the miR-24, miR-103, and miR-191 Ct data for each remaining sample was calculated, and the resulting Ct was subtracted from the raw Ct readings for miR-124 in the corresponding sample to produce a dCt. The resulting normalized values for the samples were used to estimate the relative abundance of miR-124 in each of the samples. The changes in miR-124 levels in blood, liver, and tumor were calculated by subtracting the average dCts of samples taken from mice that were treated with a negative control miRNA (Life Technologies, Inc./Ambion, Inc; Austin, Tex., USA; cat. no. AM17103) from the average dCts of samples taken from mice treated with the various miR-124 mimics. The resulting ddCt values for each miR-124 mimic were used to calculate the fold increase in miR-124 levels in the various tissues by raising 2 to the power of the ddCt value. The miR-124 fold increases over endogenous levels observed in the various tissues following injection of each miRNA mimic are shown in Table 12.

TABLE 12

Circulation and tissue accumulation of miR-124 mimics in mice. Sequences and 2'-O Me modifications of the P-passenger and A-active strands are shown in Table 5. All passenger strands had a 5'-amino C6 modification.

| Time Post Final Injection | mir-124 Mimic | Blood Fold Increase | SD | Tumor Fold Increase | SD | Liver Fold Increase | SD |
| --- | --- | --- | --- | --- | --- | --- | --- |
| 10 min | P101/A111 | 52 | 5 | 139 | 27 | 18 | 3 |
| 10 min | P102/A119 | 347 | 39 | 135 | 53 | 95 | 9 |
| 10 min | P107/A119 | 1722 | 119 | 183 | 28 | 154 | 30 |
| 10 min | P108/A113 | 1779 | 61 | 381 | 105 | 245 | 15 |
| 60 min | P101/A111 | 3 | 1 | 4 | 1 | 3 | 2 |
| 60 min | P102/A119 | 40 | 11 | 92 | 47 | 6 | 3 |
| 60 min | P107/A119 | 73 | 17 | 50 | 26 | 16 | 3 |
| 60 min | P108/A113 | 118 | 8 | 73 | 5 | 17 | 4 |

Ten minutes after injecting mice with miR-124 mimics, the inventors observed miR-124 levels in blood that were 52-fold to 1,779-fold higher than levels observed after injection with a negative control miRNA. Elevated miR-124 levels were also observed in blood sixty minutes after injection with mimics. Injection with each of the 2'O-Me-modified mimics induced higher comparative blood levels of miR-124 than did injection with the unmodified mimic. Similar results were observed for miR-124 levels in liver tissues and in the xenograft tumors. The results indicate that the 2'O-Me-modified mimics used here result in enhanced blood, tumor, and tissue persistence as compared to an unmodified mimic.

REFERENCES

The following references, to the extent that they provide exemplary procedural or other details supplementary to those set forth herein, are specifically incorporated herein by reference.

Bagga et al., Cell, 122(4):553-563, 2005.

Calin and Croce, Nat. Rev. Cancer, 6(11):857-866, 2006.

Esquela-Kerscher and Slack, Nat. Rev. Cancer, 6(4):259-269, 2006.

Freireich et al., Cancer Chemother. Rep, 50(4):219-244, 1966.

Griffiths-Jones et al., Nucleic Acids Res., 34:D140-D144, 2006.

Hu-Lieskovan et al., Cancer Res., 65(19):8984-92, 2005.

Jeffs et al., Pharma. Res., 22(3):362-72, 2005.

Lau et al., Science, 294(5543):858-862, 2001.

Lagos-Quintana et al., RNA, 9(2):175-179, 2003.

Lee and Ambros, Science, 294(5543):862-864, 2001.

Lim et al., Nature, 433(7027):769-773, 2005.

Wiemer, Eur. J. Cancer, 43(10):1529-1544, 2007.

What is claimed is:

1. A method for treating a cancer in an individual in need thereof, comprising administering to the individual a double-stranded RNA molecule 19-22 basepairs in length comprising:
   (a) an active strand comprising a sequence that is at least 90% identical to a sequence according to SEQ ID NO: 1; and
   (b) a separate passenger strand comprising
      (i) a sequence that is at least 60% complementary to the active strand,
      (ii) a 5' end terminal nucleotide modification, and
      (iii) modified nucleotides in the first two and last two positions of the passenger strand.

2. The method of claim 1, wherein the active strand comprises a sequence according to SEQ ID NO 2.

3. The method of claim 1, wherein the passenger strand comprises a sequence according to SEQ ID NO: 4.

4. The method of claim 1, wherein the active strand comprises a sequence according to SEQ ID NO:2 and the passenger strand comprises a sequence according to SEQ ID NO: 4.

5. The method of claim 1, wherein the modified nucleotides comprise a sugar modification.

6. The method of claim 5, wherein the sugar modification is a 2'-O-Me modification.

7. The method of claim 1, wherein the 5' end terminal nucleotide modification of the passenger strand is a 5' terminal cap.

8. The method of claim 7, wherein the 5' terminal cap comprises a lower alkylamine group.

9. The method of claim 8, wherein the 5' terminal cap is a C4-C12 alkylamine group.

10. The method of claim 9, wherein the 5' terminal cap is a C6 alkylamine group.

11. The method of claim 3, wherein the passenger strand further comprises a modified nucleotide from 5' to 3' at positions 3, 4, 5, 6, 13, 14, 15, 16, 17, 18, 19, and/or 20 relative to SEQ ID NO: 4.

12. The method of claim 3, wherein the passenger strand further comprises two modified nucleotides from 5' to 3' at positions 3, 4, 5, 6, 13, 14, 15, 16, 17, 18, 19, and/or 20 relative to SEQ ID NO:4.

13. The method of claim 3, wherein the passenger strand further comprises modified nucleotides from 5' to 3' at positions: (a) 3 and 4; (b) 5 and 6; (c) 13 and 14; (d) 15 and 16; (e) 17 and 18; (f) 19 and 20; (g) 3 and 20; (h) 3, 4, and 20; or (i) 3, 4, 5, 6, and 20 relative to SEQ ID NO: 4.

14. The method of claim 2, wherein the active strand comprises a modified nucleotide from 5' to 3' at positions 5, 6, 7, 8, 9, 10, 11, 12, 17, and/or 18 relative to SEQ ID NO: 2.

15. The method of claim 2, wherein the active strand comprises two modified nucleotides from 5' to 3' at positions 5, 6, 7, 8, 9, 10, 11, 12, 17, and/or 18 relative to SEQ ID NO: 2.

16. The method of claim 2, wherein the active strand comprises modified nucleotides from 5' to 3' at positions: (a) 5 and 6; (b) 7 and 8;(c) 11 and 12; (d) 17 and 18; (e) 7, 8, 17, and 18; (f) 7, 8, 11, and 12; or (g) 7, 8, 9, 10, 11, and 12 relative to SEQ ID NO: 2.

17. The method of claim 1, wherein
   (a) the active strand comprises a sequence according to SEQ ID NO: 2, and one or more modified nucleotides from 5' to 3' at one or more of positions 5, 6, 7, 8, 11, 12, 17, and 18 relative to SEQ ID NO: 2; and
   (b) the passenger strand comprises a sequence according to SEQ ID NO: 4, and one or more modified nucleotides from 5' to 3' at one or more of positions 3, 4, 5, 6, 13, 14, 15, 16, 17, 18, 19, and 20 relative to SEQ ID NO: 4.

18. The method of claim 1, wherein
   (a) the active strand comprises a sequence according to SEQ ID NO: 2 and modified nucleotides from 5' to 3' at positions 5 and 6 relative to SEQ ID NO: 2; and
   (b) the passenger strand comprises a sequence according to SEQ ID NO: 4 and modified nucleotides from 5' to 3' at positions 3 and 20 relative to SEQ ID NO: 4.

19. The method of claim 1, wherein
   (a) the active strand comprises a sequence according to SEQ ID NO: 2 and modified nucleotides from 5' to 3' at positions 7 and 8 relative to SEQ ID NO: 2; and
   (b) the passenger strand comprises a sequence according to SEQ ID NO: 4 and modified nucleotides from 5' to 3' at positions 3 and 20 relative to SEQ ID NO: 4.

20. The method of claim 1, wherein
   (a) the active strand comprises a sequence according to SEQ ID NO: 2 and modified nucleotides from 5' to 3' at positions 17 and 18 relative to SEQ ID NO: 2; and
   (b) the passenger strand comprises a sequence according to SEQ ID NO: 4 and modified nucleotides from 5' to 3' at positions 3 and 20 relative to SEQ ID NO: 4.

21. The method of claim 1, wherein
   (a) the active strand comprises a sequence according to SEQ ID NO: 2 and modified nucleotides from 5' to 3' at positions 7, 8, 9, 10, 11, and 12 relative to SEQ ID NO: 2; and
   (b) the passenger strand comprises a sequence according to SEQ ID NO: 4 and modified nucleotides from 5' to 3' at positions 3 and 20 relative to SEQ ID NO: 4.

22. The method of claim 1, wherein
   (a) the active strand comprises a sequence according to SEQ ID NO: 2 and modified nucleotides from 5' to 3' at positions 7, 8, 9, 10, 11, and 12 relative to SEQ ID NO: 2; and
   (b) the passenger strand comprises a sequence according to SEQ ID NO: 4 and modified nucleotides from 5' to 3' at positions 3, 4, and 20 relative to SEQ ID NO: 4.

23. The method of claim 1, wherein
   (a) the active strand comprises a sequence according to SEQ ID NO: 2 and modified nucleotides from 5' to 3' at positions 7, 8, 17 and 18 relative to SEQ ID NO: 2; and
   (b) the passenger strand comprises a sequence according to SEQ ID NO: 4 and modified nucleotides from 5' to 3' at positions 3, 4, 5, 6 and 20 relative to SEQ ID NO: 4.

24. The method of claim 1, wherein the cancer is a lung cancer, liver cancer, breast cancer, cervical cancer, prostate carcinoma, or basal cell carcinoma.

* * * * *

SEQUENCE LISTING

<160> NUMBER OF SEQ ID NOS: 194

<210> SEQ ID NO 1
<211> LENGTH: 20
<212> TYPE: RNA
<213> ORGANISM: Artificial Sequence
<220> FEATURE:
<223> OTHER INFORMATION: Synthetic primer

<400> SEQUENCE: 1
uaaggcacgc ggugaaugcc                                               20

<210> SEQ ID NO 2
<211> LENGTH: 22
<212> TYPE: RNA
<213> ORGANISM: Artificial Sequence
<220> FEATURE:
<223> OTHER INFORMATION: Synthetic primer

<400> SEQUENCE: 2
uuaaggcacg cggugaaugc ca                                            22

<210> SEQ ID NO 3
<211> LENGTH: 20
<212> TYPE: RNA
<213> ORGANISM: Artificial Sequence
<220> FEATURE:
<223> OTHER INFORMATION: Synthetic primer

<400> SEQUENCE: 3
ggcauucacc gcgugccuua                                               20

<210> SEQ ID NO 4
<211> LENGTH: 22
<212> TYPE: RNA
<213> ORGANISM: Artificial Sequence
<220> FEATURE:
<223> OTHER INFORMATION: Synthetic primer

<400> SEQUENCE: 4
uggcauucac cgcgugccuu aa                                            22

<210> SEQ ID NO 5
<211> LENGTH: 19
<212> TYPE: RNA
<213> ORGANISM: Artificial Sequence
<220> FEATURE:
<223> OTHER INFORMATION: Synthetic primer

<400> SEQUENCE: 5
uaaggcacgc ggugaaugc                                                19

<210> SEQ ID NO 6
<211> LENGTH: 19
<212> TYPE: RNA
<213> ORGANISM: Artificial Sequence
<220> FEATURE:
<223> OTHER INFORMATION: Synthetic primer

<400> SEQUENCE: 6
uaaggcacgc ggugaaucc                                                19

<210> SEQ ID NO 7
<211> LENGTH: 19
<212> TYPE: RNA
<213> ORGANISM: Artificial Sequence

```
<220> FEATURE:
<223> OTHER INFORMATION: Synthetic primer

<400> SEQUENCE: 7
uaaggcacgc ggugaagcc                                                19

<210> SEQ ID NO 8
<211> LENGTH: 19
<212> TYPE: RNA
<213> ORGANISM: Artificial Sequence
<220> FEATURE:
<223> OTHER INFORMATION: Synthetic primer

<400> SEQUENCE: 8
uaaggcacgc ggugaugcc                                                19

<210> SEQ ID NO 9
<211> LENGTH: 19
<212> TYPE: RNA
<213> ORGANISM: Artificial Sequence
<220> FEATURE:
<223> OTHER INFORMATION: Synthetic primer

<400> SEQUENCE: 9
uaaggcacgc gguaaugcc                                                19

<210> SEQ ID NO 10
<211> LENGTH: 19
<212> TYPE: RNA
<213> ORGANISM: Artificial Sequence
<220> FEATURE:
<223> OTHER INFORMATION: Synthetic primer

<400> SEQUENCE: 10
uaaggcacgc gggaaugcc                                                19

<210> SEQ ID NO 11
<211> LENGTH: 19
<212> TYPE: RNA
<213> ORGANISM: Artificial Sequence
<220> FEATURE:
<223> OTHER INFORMATION: Synthetic primer

<400> SEQUENCE: 11
uaaggcacgc gugaaugcc                                                19

<210> SEQ ID NO 12
<211> LENGTH: 19
<212> TYPE: RNA
<213> ORGANISM: Artificial Sequence
<220> FEATURE:
<223> OTHER INFORMATION: Synthetic primer

<400> SEQUENCE: 12
uaaggcacgg gugaaugcc                                                19

<210> SEQ ID NO 13
<211> LENGTH: 19
<212> TYPE: RNA
<213> ORGANISM: Artificial Sequence
<220> FEATURE:
<223> OTHER INFORMATION: Synthetic primer

<400> SEQUENCE: 13
uaaggcaccg gugaaugcc                                                19
```

```
<210> SEQ ID NO 14
<211> LENGTH: 19
<212> TYPE: RNA
<213> ORGANISM: Artificial Sequence
<220> FEATURE:
<223> OTHER INFORMATION: Synthetic primer

<400> SEQUENCE: 14
uaaggcagcg gugaaugcc                                                    19

<210> SEQ ID NO 15
<211> LENGTH: 19
<212> TYPE: RNA
<213> ORGANISM: Artificial Sequence
<220> FEATURE:
<223> OTHER INFORMATION: Synthetic primer

<400> SEQUENCE: 15
uaaggccgcg gugaaugcc                                                    19

<210> SEQ ID NO 16
<211> LENGTH: 19
<212> TYPE: RNA
<213> ORGANISM: Artificial Sequence
<220> FEATURE:
<223> OTHER INFORMATION: Synthetic primer

<400> SEQUENCE: 16
uaaggacgcg gugaaugcc                                                    19

<210> SEQ ID NO 17
<211> LENGTH: 19
<212> TYPE: RNA
<213> ORGANISM: Artificial Sequence
<220> FEATURE:
<223> OTHER INFORMATION: Synthetic primer

<400> SEQUENCE: 17
uaagcacgcg gugaaugcc                                                    19

<210> SEQ ID NO 18
<211> LENGTH: 19
<212> TYPE: RNA
<213> ORGANISM: Artificial Sequence
<220> FEATURE:
<223> OTHER INFORMATION: Synthetic primer

<400> SEQUENCE: 18
uaggcacgcg gugaaugcc                                                    19

<210> SEQ ID NO 19
<211> LENGTH: 19
<212> TYPE: RNA
<213> ORGANISM: Artificial Sequence
<220> FEATURE:
<223> OTHER INFORMATION: Synthetic primer

<400> SEQUENCE: 19
aaggcacgcg gugaaugcc                                                    19

<210> SEQ ID NO 20
<211> LENGTH: 21
<212> TYPE: RNA
<213> ORGANISM: Artificial Sequence
<220> FEATURE:
<223> OTHER INFORMATION: Synthetic primer
```

```
<400> SEQUENCE: 20
uuaaggcacg cggugaaugc c                                              21

<210> SEQ ID NO 21
<211> LENGTH: 21
<212> TYPE: RNA
<213> ORGANISM: Artificial Sequence
<220> FEATURE:
<223> OTHER INFORMATION: Synthetic primer

<400> SEQUENCE: 21
uuaaggcacg cggugaaugc a                                              21

<210> SEQ ID NO 22
<211> LENGTH: 21
<212> TYPE: RNA
<213> ORGANISM: Artificial Sequence
<220> FEATURE:
<223> OTHER INFORMATION: Synthetic primer

<400> SEQUENCE: 22
uuaaggcacg cggugaaucc a                                              21

<210> SEQ ID NO 23
<211> LENGTH: 21
<212> TYPE: RNA
<213> ORGANISM: Artificial Sequence
<220> FEATURE:
<223> OTHER INFORMATION: Synthetic primer

<400> SEQUENCE: 23
uuaaggcacg cggugaagcc a                                              21

<210> SEQ ID NO 24
<211> LENGTH: 21
<212> TYPE: RNA
<213> ORGANISM: Artificial Sequence
<220> FEATURE:
<223> OTHER INFORMATION: Synthetic primer

<400> SEQUENCE: 24
uuaaggcacg cggugaugcc a                                              21

<210> SEQ ID NO 25
<211> LENGTH: 21
<212> TYPE: RNA
<213> ORGANISM: Artificial Sequence
<220> FEATURE:
<223> OTHER INFORMATION: Synthetic primer

<400> SEQUENCE: 25
uuaaggcacg cgguaaugcc a                                              21

<210> SEQ ID NO 26
<211> LENGTH: 21
<212> TYPE: RNA
<213> ORGANISM: Artificial Sequence
<220> FEATURE:
<223> OTHER INFORMATION: Synthetic primer

<400> SEQUENCE: 26
uuaaggcacg cgggaaugcc a                                              21

<210> SEQ ID NO 27
```

```
<211> LENGTH: 21
<212> TYPE: RNA
<213> ORGANISM: Artificial Sequence
<220> FEATURE:
<223> OTHER INFORMATION: Synthetic primer

<400> SEQUENCE: 27
uuaaggcacg cgugaaugcc a                                              21

<210> SEQ ID NO 28
<211> LENGTH: 21
<212> TYPE: RNA
<213> ORGANISM: Artificial Sequence
<220> FEATURE:
<223> OTHER INFORMATION: Synthetic primer

<400> SEQUENCE: 28
uuaaggcacg ggugaaugcc a                                              21

<210> SEQ ID NO 29
<211> LENGTH: 21
<212> TYPE: RNA
<213> ORGANISM: Artificial Sequence
<220> FEATURE:
<223> OTHER INFORMATION: Synthetic primer

<400> SEQUENCE: 29
uuaaggcacc ggugaaugcc a                                              21

<210> SEQ ID NO 30
<211> LENGTH: 21
<212> TYPE: RNA
<213> ORGANISM: Artificial Sequence
<220> FEATURE:
<223> OTHER INFORMATION: Synthetic primer

<400> SEQUENCE: 30
uuaaggcagc ggugaaugcc a                                              21

<210> SEQ ID NO 31
<211> LENGTH: 21
<212> TYPE: RNA
<213> ORGANISM: Artificial Sequence
<220> FEATURE:
<223> OTHER INFORMATION: Synthetic primer

<400> SEQUENCE: 31
uuaaggccgc ggugaaugcc a                                              21

<210> SEQ ID NO 32
<211> LENGTH: 21
<212> TYPE: RNA
<213> ORGANISM: Artificial Sequence
<220> FEATURE:
<223> OTHER INFORMATION: Synthetic primer

<400> SEQUENCE: 32
uuaaggacgc ggugaaugcc a                                              21

<210> SEQ ID NO 33
<211> LENGTH: 21
<212> TYPE: RNA
<213> ORGANISM: Artificial Sequence
<220> FEATURE:
<223> OTHER INFORMATION: Synthetic primer

<400> SEQUENCE: 33
```

```
uuaagcacgc ggugaaugcc a                                              21

<210> SEQ ID NO 34
<211> LENGTH: 21
<212> TYPE: RNA
<213> ORGANISM: Artificial Sequence
<220> FEATURE:
<223> OTHER INFORMATION: Synthetic primer

<400> SEQUENCE: 34
uuaggcacgc ggugaaugcc a                                              21

<210> SEQ ID NO 35
<211> LENGTH: 21
<212> TYPE: RNA
<213> ORGANISM: Artificial Sequence
<220> FEATURE:
<223> OTHER INFORMATION: Synthetic primer

<400> SEQUENCE: 35
uaaggcacgc ggugaaugcc a                                              21

<210> SEQ ID NO 36
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or u

<400> SEQUENCE: 36
naaggcacgc ggugaaugcc                                                20

<210> SEQ ID NO 37
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (2)..(2)
<223> OTHER INFORMATION: n is a, c, g, or u

<400> SEQUENCE: 37
unaggcacgc ggugaaugcc                                                20

<210> SEQ ID NO 38
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is a, c, g, or u

<400> SEQUENCE: 38
uanggcacgc ggugaaugcc                                                20

<210> SEQ ID NO 39
<211> LENGTH: 20
<212> TYPE: RNA
```

```
<213> ORGANISM: Artificial Sequence
<220> FEATURE:
<223> OTHER INFORMATION: Synthetic primer
<220> FEATURE:
<221> NAME/KEY: misc_feature
<222> LOCATION: (4)..(4)
<223> OTHER INFORMATION: n is a, c, g, or u

<400> SEQUENCE: 39
uaangcacgc ggugaaugcc                                               20

<210> SEQ ID NO 40
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (5)..(5)
<223> OTHER INFORMATION: n is a, c, g, or u

<400> SEQUENCE: 40
uaagncacgc ggugaaugcc                                               20

<210> SEQ ID NO 41
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: n is a, c, g, or u

<400> SEQUENCE: 41
uaaggnacgc ggugaaugcc                                               20

<210> SEQ ID NO 42
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (7)..(7)
<223> OTHER INFORMATION: n is a, c, g, or u

<400> SEQUENCE: 42
uaaggcncgc ggugaaugcc                                               20

<210> SEQ ID NO 43
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (8)..(8)
<223> OTHER INFORMATION: n is a, c, g, or u

<400> SEQUENCE: 43
uaaggcangc ggugaaugcc                                               20

<210> SEQ ID NO 44
<211> LENGTH: 20
```

```
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (9)..(9)
<223> OTHER INFORMATION: n is a, c, g, or u

<400> SEQUENCE: 44
uaaggcacnc ggugaaugcc                                              20

<210> SEQ ID NO 45
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (10)..(10)
<223> OTHER INFORMATION: n is a, c, g, or u

<400> SEQUENCE: 45
uaaggcacgn ggugaaugcc                                              20

<210> SEQ ID NO 46
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (11)..(11)
<223> OTHER INFORMATION: n is a, c, g, or u

<400> SEQUENCE: 46
uaaggcacgc ngugaaugcc                                              20

<210> SEQ ID NO 47
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (12)..(12)
<223> OTHER INFORMATION: n is a, c, g, or u

<400> SEQUENCE: 47
uaaggcacgc gnugaaugcc                                              20

<210> SEQ ID NO 48
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (13)..(13)
<223> OTHER INFORMATION: n is a, c, g, or u

<400> SEQUENCE: 48
uaaggcacgc ggngaaugcc                                              20

<210> SEQ ID NO 49
```

```
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (14)..(14)
<223> OTHER INFORMATION: n is a, c, g, or u

<400> SEQUENCE: 49
uaaggcacgc ggunaaugcc                                               20

<210> SEQ ID NO 50
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (15)..(15)
<223> OTHER INFORMATION: n is a, c, g, or u

<400> SEQUENCE: 50
uaaggcacgc ggugnaugcc                                               20

<210> SEQ ID NO 51
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (16)..(16)
<223> OTHER INFORMATION: n is a, c, g, or u

<400> SEQUENCE: 51
uaaggcacgc gguganugcc                                               20

<210> SEQ ID NO 52
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (17)..(17)
<223> OTHER INFORMATION: n is a, c, g, or u

<400> SEQUENCE: 52
uaaggcacgc ggugaangcc                                               20

<210> SEQ ID NO 53
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (18)..(18)
<223> OTHER INFORMATION: n is a, c, g, or u

<400> SEQUENCE: 53
uaaggcacgc ggugaauncc                                               20
```

```
<210> SEQ ID NO 54
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (19)..(19)
<223> OTHER INFORMATION: n is a, c, g, or u

<400> SEQUENCE: 54
uaaggcacgc ggugaaugnc                                              20

<210> SEQ ID NO 55
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (20)..(20)
<223> OTHER INFORMATION: n is a, c, g, or u

<400> SEQUENCE: 55
uaaggcacgc ggugaaugcn                                              20

<210> SEQ ID NO 56
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or u

<400> SEQUENCE: 56
nuaaggcacg cggugaaugc c                                            21

<210> SEQ ID NO 57
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (2)..(2)
<223> OTHER INFORMATION: n is a, c, g, or u

<400> SEQUENCE: 57
unaaggcacg cggugaaugc c                                            21

<210> SEQ ID NO 58
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is a, c, g, or u

<400> SEQUENCE: 58
uanaggcacg cggugaaugc c                                            21
```

```
<210> SEQ ID NO 59
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (4)..(4)
<223> OTHER INFORMATION: n is a, c, g, or u

<400> SEQUENCE: 59
uaanggcacg cggugaaugc c                                              21

<210> SEQ ID NO 60
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (5)..(5)
<223> OTHER INFORMATION: n is a, c, g, or u

<400> SEQUENCE: 60
uaagngcacg cggugaaugc c                                              21

<210> SEQ ID NO 61
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: n is a, c, g, or u

<400> SEQUENCE: 61
uaaggncacg cggugaaugc c                                              21

<210> SEQ ID NO 62
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (7)..(7)
<223> OTHER INFORMATION: n is a, c, g, or u

<400> SEQUENCE: 62
uaaggcnacg cggugaaugc c                                              21

<210> SEQ ID NO 63
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (8)..(8)
<223> OTHER INFORMATION: n is a, c, g, or u

<400> SEQUENCE: 63
uaaggcancg cggugaaugc c                                              21
```

```
<210> SEQ ID NO 64
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (9)..(9)
<223> OTHER INFORMATION: n is a, c, g, or u

<400> SEQUENCE: 64
uaaggcacng cggugaaugc c                                              21

<210> SEQ ID NO 65
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (10)..(10)
<223> OTHER INFORMATION: n is a, c, g, or u

<400> SEQUENCE: 65
uaaggcacgn cggugaaugc c                                              21

<210> SEQ ID NO 66
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (11)..(11)
<223> OTHER INFORMATION: n is a, c, g, or u

<400> SEQUENCE: 66
uaaggcacgc nggugaaugc c                                              21

<210> SEQ ID NO 67
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (12)..(12)
<223> OTHER INFORMATION: n is a, c, g, or u

<400> SEQUENCE: 67
uaaggcacgc gngugaaugc c                                              21

<210> SEQ ID NO 68
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (13)..(13)
<223> OTHER INFORMATION: n is a, c, g, or u

<400> SEQUENCE: 68
```
uaaggcacgc ggnugaaugc c                                              21

<210> SEQ ID NO 69
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (14)..(14)
<223> OTHER INFORMATION: n is a, c, g, or u

<400> SEQUENCE: 69
uaaggcacgc ggungaaugc c                                              21

<210> SEQ ID NO 70
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (15)..(15)
<223> OTHER INFORMATION: n is a, c, g, or u

<400> SEQUENCE: 70
uaaggcacgc ggugnaaugc c                                              21

<210> SEQ ID NO 71
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (16)..(16)
<223> OTHER INFORMATION: n is a, c, g, or u

<400> SEQUENCE: 71
uaaggcacgc gguganaugc c                                              21

<210> SEQ ID NO 72
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (17)..(17)
<223> OTHER INFORMATION: n is a, c, g, or u

<400> SEQUENCE: 72
uaaggcacgc ggugaanugc c                                              21

<210> SEQ ID NO 73
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (18)..(18)
<223> OTHER INFORMATION: n is a, c, g, or u

<400> SEQUENCE: 73

```
uaaggcacgc ggugaaungc c                                              21

<210> SEQ ID NO 74
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (19)..(19)
<223> OTHER INFORMATION: n is a, c, g, or u

<400> SEQUENCE: 74
uaaggcacgc ggugaaugnc c                                              21

<210> SEQ ID NO 75
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (20)..(20)
<223> OTHER INFORMATION: n is a, c, g, or u

<400> SEQUENCE: 75
uaaggcacgc ggugaaugcn c                                              21

<210> SEQ ID NO 76
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (21)..(21)
<223> OTHER INFORMATION: n is a, c, g, or u

<400> SEQUENCE: 76
uaaggcacgc ggugaaugcc n                                              21

<210> SEQ ID NO 77
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or u

<400> SEQUENCE: 77
nuaaggcacg cggugaaugc ca                                             22

<210> SEQ ID NO 78
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (2)..(2)
<223> OTHER INFORMATION: n is a, c, g, or u
```

```
<400> SEQUENCE: 78
unaaggcacg cggugaaugc ca                                            22

<210> SEQ ID NO 79
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is a, c, g, or u

<400> SEQUENCE: 79
uunaggcacg cggugaaugc ca                                            22

<210> SEQ ID NO 80
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (4)..(4)
<223> OTHER INFORMATION: n is a, c, g, or u

<400> SEQUENCE: 80
uuanggcacg cggugaaugc ca                                            22

<210> SEQ ID NO 81
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (5)..(5)
<223> OTHER INFORMATION: n is a, c, g, or u

<400> SEQUENCE: 81
uuaangcacg cggugaaugc ca                                            22

<210> SEQ ID NO 82
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: n is a, c, g, or u

<400> SEQUENCE: 82
uuaagncacg cggugaaugc ca                                            22

<210> SEQ ID NO 83
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (7)..(7)
<223> OTHER INFORMATION: n is a, c, g, or u
```

```
<400> SEQUENCE: 83
uuaaggnacg cggugaaugc ca                                              22

<210> SEQ ID NO 84
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (8)..(8)
<223> OTHER INFORMATION: n is a, c, g, or u

<400> SEQUENCE: 84
uuaaggcncg cggugaaugc ca                                              22

<210> SEQ ID NO 85
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (9)..(9)
<223> OTHER INFORMATION: n is a, c, g, or u

<400> SEQUENCE: 85
uuaaggcang cggugaaugc ca                                              22

<210> SEQ ID NO 86
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (10)..(10)
<223> OTHER INFORMATION: n is a, c, g, or u

<400> SEQUENCE: 86
uuaaggcacn cggugaaugc ca                                              22

<210> SEQ ID NO 87
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (11)..(11)
<223> OTHER INFORMATION: n is a, c, g, or u

<400> SEQUENCE: 87
uuaaggcacg nggugaaugc ca                                              22

<210> SEQ ID NO 88
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (12)..(12)
```

<223> OTHER INFORMATION: n is a, c, g, or u

<400> SEQUENCE: 88
uuaaggcacg cngugaaugc ca                                          22

<210> SEQ ID NO 89
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (13)..(13)
<223> OTHER INFORMATION: n is a, c, g, or u

<400> SEQUENCE: 89
uuaaggcacg cgnugaaugc ca                                          22

<210> SEQ ID NO 90
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (14)..(14)
<223> OTHER INFORMATION: n is a, c, g, or u

<400> SEQUENCE: 90
uuaaggcacg cggngaaugc ca                                          22

<210> SEQ ID NO 91
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (15)..(15)
<223> OTHER INFORMATION: n is a, c, g, or u

<400> SEQUENCE: 91
uuaaggcacg cggunaaugc ca                                          22

<210> SEQ ID NO 92
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (16)..(16)
<223> OTHER INFORMATION: n is a, c, g, or u

<400> SEQUENCE: 92
uuaaggcacg cggugnaugc ca                                          22

<210> SEQ ID NO 93
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature

```
<222> LOCATION: (17)..(17)
<223> OTHER INFORMATION: n is a, c, g, or u

<400> SEQUENCE: 93
uuaaggcacg cgguganugc ca                                              22

<210> SEQ ID NO 94
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (18)..(18)
<223> OTHER INFORMATION: n is a, c, g, or u

<400> SEQUENCE: 94
uuaaggcacg cggugaangc ca                                              22

<210> SEQ ID NO 95
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (19)..(19)
<223> OTHER INFORMATION: n is a, c, g, or u

<400> SEQUENCE: 95
uuaaggcacg cggugaaunc ca                                              22

<210> SEQ ID NO 96
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (20)..(20)
<223> OTHER INFORMATION: n is a, c, g, or u

<400> SEQUENCE: 96
uuaaggcacg cggugaaugn ca                                              22

<210> SEQ ID NO 97
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (21)..(21)
<223> OTHER INFORMATION: n is a, c, g, or u

<400> SEQUENCE: 97
uuaaggcacg cggugaaugc na                                              22

<210> SEQ ID NO 98
<211> LENGTH: 22
<212> TYPE: RNA
<213> ORGANISM: Artificial Sequence
<220> FEATURE:
<223> OTHER INFORMATION: Synthetic primer
<220> FEATURE:
```

```
<221> NAME/KEY: misc_feature
<222> LOCATION: (22)..(22)
<223> OTHER INFORMATION: n is a, c, g, or u

<400> SEQUENCE: 98
uuaaggcacg cggugaaugc cn                                            22

<210> SEQ ID NO 99
<211> LENGTH: 19
<212> TYPE: RNA
<213> ORGANISM: Artificial Sequence
<220> FEATURE:
<223> OTHER INFORMATION: Synthetic primer

<400> SEQUENCE: 99
ggcauucacc gcgugccuu                                                19

<210> SEQ ID NO 100
<211> LENGTH: 19
<212> TYPE: RNA
<213> ORGANISM: Artificial Sequence
<220> FEATURE:
<223> OTHER INFORMATION: Synthetic primer

<400> SEQUENCE: 100
ggcauucacc gcgugccua                                                19

<210> SEQ ID NO 101
<211> LENGTH: 19
<212> TYPE: RNA
<213> ORGANISM: Artificial Sequence
<220> FEATURE:
<223> OTHER INFORMATION: Synthetic primer

<400> SEQUENCE: 101
ggcauucacc gcgugcuua                                                19

<210> SEQ ID NO 102
<211> LENGTH: 19
<212> TYPE: RNA
<213> ORGANISM: Artificial Sequence
<220> FEATURE:
<223> OTHER INFORMATION: Synthetic primer

<400> SEQUENCE: 102
ggcauucacc gcguccuua                                                19

<210> SEQ ID NO 103
<211> LENGTH: 19
<212> TYPE: RNA
<213> ORGANISM: Artificial Sequence
<220> FEATURE:
<223> OTHER INFORMATION: Synthetic primer

<400> SEQUENCE: 103
ggcauucacc gcggccuua                                                19

<210> SEQ ID NO 104
<211> LENGTH: 19
<212> TYPE: RNA
<213> ORGANISM: Artificial Sequence
<220> FEATURE:
<223> OTHER INFORMATION: Synthetic primer

<400> SEQUENCE: 104
ggcauucacc gcugccuua                                                19
```

<210> SEQ ID NO 105
<211> LENGTH: 19
<212> TYPE: RNA
<213> ORGANISM: Artificial Sequence
<220> FEATURE:
<223> OTHER INFORMATION: Synthetic primer

<400> SEQUENCE: 105
ggcauucacc ggugccuua                                                  19

<210> SEQ ID NO 106
<211> LENGTH: 19
<212> TYPE: RNA
<213> ORGANISM: Artificial Sequence
<220> FEATURE:
<223> OTHER INFORMATION: Synthetic primer

<400> SEQUENCE: 106
ggcauucacc cgugccuua                                                  19

<210> SEQ ID NO 107
<211> LENGTH: 19
<212> TYPE: RNA
<213> ORGANISM: Artificial Sequence
<220> FEATURE:
<223> OTHER INFORMATION: Synthetic primer

<400> SEQUENCE: 107
ggcauucacg cgugccuua                                                  19

<210> SEQ ID NO 108
<211> LENGTH: 19
<212> TYPE: RNA
<213> ORGANISM: Artificial Sequence
<220> FEATURE:
<223> OTHER INFORMATION: Synthetic primer

<400> SEQUENCE: 108
ggcauucccg cgugccuua                                                  19

<210> SEQ ID NO 109
<211> LENGTH: 19
<212> TYPE: RNA
<213> ORGANISM: Artificial Sequence
<220> FEATURE:
<223> OTHER INFORMATION: Synthetic primer

<400> SEQUENCE: 109
ggcauuaccg cgugccuua                                                  19

<210> SEQ ID NO 110
<211> LENGTH: 19
<212> TYPE: RNA
<213> ORGANISM: Artificial Sequence
<220> FEATURE:
<223> OTHER INFORMATION: Synthetic primer

<400> SEQUENCE: 110
ggcaucaccg cgugccuua                                                  19

<210> SEQ ID NO 111
<211> LENGTH: 19
<212> TYPE: RNA
<213> ORGANISM: Artificial Sequence
<220> FEATURE:

<223> OTHER INFORMATION: Synthetic primer

<400> SEQUENCE: 111
ggcuucaccg cgugccuua                                                                19

<210> SEQ ID NO 112
<211> LENGTH: 19
<212> TYPE: RNA
<213> ORGANISM: Artificial Sequence
<220> FEATURE:
<223> OTHER INFORMATION: Synthetic primer

<400> SEQUENCE: 112
ggauucaccg cgugccuua                                                                19

<210> SEQ ID NO 113
<211> LENGTH: 19
<212> TYPE: RNA
<213> ORGANISM: Artificial Sequence
<220> FEATURE:
<223> OTHER INFORMATION: Synthetic primer

<400> SEQUENCE: 113
gcauucaccg cgugccuua                                                                19

<210> SEQ ID NO 114
<211> LENGTH: 21
<212> TYPE: RNA
<213> ORGANISM: Artificial Sequence
<220> FEATURE:
<223> OTHER INFORMATION: Synthetic primer

<400> SEQUENCE: 114
uggcauucac cgcgugccuu a                                                             21

<210> SEQ ID NO 115
<211> LENGTH: 21
<212> TYPE: RNA
<213> ORGANISM: Artificial Sequence
<220> FEATURE:
<223> OTHER INFORMATION: Synthetic primer

<400> SEQUENCE: 115
uggcauucac cgcgugccua a                                                             21

<210> SEQ ID NO 116
<211> LENGTH: 21
<212> TYPE: RNA
<213> ORGANISM: Artificial Sequence
<220> FEATURE:
<223> OTHER INFORMATION: Synthetic primer

<400> SEQUENCE: 116
uggcauucac cgcgugcuua a                                                             21

<210> SEQ ID NO 117
<211> LENGTH: 21
<212> TYPE: RNA
<213> ORGANISM: Artificial Sequence
<220> FEATURE:
<223> OTHER INFORMATION: Synthetic primer

<400> SEQUENCE: 117
uggcauucac cgcguccuua a                                                             21

```
<210> SEQ ID NO 118
<211> LENGTH: 21
<212> TYPE: RNA
<213> ORGANISM: Artificial Sequence
<220> FEATURE:
<223> OTHER INFORMATION: Synthetic primer

<400> SEQUENCE: 118
uggcauucac cgcggccuua a                                              21

<210> SEQ ID NO 119
<211> LENGTH: 21
<212> TYPE: RNA
<213> ORGANISM: Artificial Sequence
<220> FEATURE:
<223> OTHER INFORMATION: Synthetic primer

<400> SEQUENCE: 119
uggcauucac cgcugccuua a                                              21

<210> SEQ ID NO 120
<211> LENGTH: 21
<212> TYPE: RNA
<213> ORGANISM: Artificial Sequence
<220> FEATURE:
<223> OTHER INFORMATION: Synthetic primer

<400> SEQUENCE: 120
uggcauucac cggugccuua a                                              21

<210> SEQ ID NO 121
<211> LENGTH: 21
<212> TYPE: RNA
<213> ORGANISM: Artificial Sequence
<220> FEATURE:
<223> OTHER INFORMATION: Synthetic primer

<400> SEQUENCE: 121
uggcauucac ccgugccuua a                                              21

<210> SEQ ID NO 122
<211> LENGTH: 21
<212> TYPE: RNA
<213> ORGANISM: Artificial Sequence
<220> FEATURE:
<223> OTHER INFORMATION: Synthetic primer

<400> SEQUENCE: 122
uggcauucac gcgugccuua a                                              21

<210> SEQ ID NO 123
<211> LENGTH: 21
<212> TYPE: RNA
<213> ORGANISM: Artificial Sequence
<220> FEATURE:
<223> OTHER INFORMATION: Synthetic primer

<400> SEQUENCE: 123
uggcauuccc gcgugccuua a                                              21

<210> SEQ ID NO 124
<211> LENGTH: 21
<212> TYPE: RNA
<213> ORGANISM: Artificial Sequence
<220> FEATURE:
<223> OTHER INFORMATION: Synthetic primer
```

-continued

<400> SEQUENCE: 124
uggcauuacc gcgugccuua a                                              21

<210> SEQ ID NO 125
<211> LENGTH: 21
<212> TYPE: RNA
<213> ORGANISM: Artificial Sequence
<220> FEATURE:
<223> OTHER INFORMATION: Synthetic primer

<400> SEQUENCE: 125
uggcaucacc gcgugccuua a                                              21

<210> SEQ ID NO 126
<211> LENGTH: 21
<212> TYPE: RNA
<213> ORGANISM: Artificial Sequence
<220> FEATURE:
<223> OTHER INFORMATION: Synthetic primer

<400> SEQUENCE: 126
uggcuucacc gcgugccuua a                                              21

<210> SEQ ID NO 127
<211> LENGTH: 21
<212> TYPE: RNA
<213> ORGANISM: Artificial Sequence
<220> FEATURE:
<223> OTHER INFORMATION: Synthetic primer

<400> SEQUENCE: 127
uggauucacc gcgugccuua a                                              21

<210> SEQ ID NO 128
<211> LENGTH: 21
<212> TYPE: RNA
<213> ORGANISM: Artificial Sequence
<220> FEATURE:
<223> OTHER INFORMATION: Synthetic primer

<400> SEQUENCE: 128
ugcauucacc gcgugccuua a                                              21

<210> SEQ ID NO 129
<211> LENGTH: 21
<212> TYPE: RNA
<213> ORGANISM: Artificial Sequence
<220> FEATURE:
<223> OTHER INFORMATION: Synthetic primer

<400> SEQUENCE: 129
ugcauucacc gcgugccuua a                                              21

<210> SEQ ID NO 130
<211> LENGTH: 21
<212> TYPE: RNA
<213> ORGANISM: Artificial Sequence
<220> FEATURE:
<223> OTHER INFORMATION: Synthetic primer

<400> SEQUENCE: 130
ggcauucacc gcgugccuua a                                              21

<210> SEQ ID NO 131
<211> LENGTH: 20

```
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or u

<400> SEQUENCE: 131
ngcauucacc gcgugccuua                                                     20

<210> SEQ ID NO 132
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (2)..(2)
<223> OTHER INFORMATION: n is a, c, g, or u

<400> SEQUENCE: 132
gncauucacc gcgugccuua                                                     20

<210> SEQ ID NO 133
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is a, c, g, or u

<400> SEQUENCE: 133
ggnauucacc gcgugccuua                                                     20

<210> SEQ ID NO 134
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (4)..(4)
<223> OTHER INFORMATION: n is a, c, g, or u

<400> SEQUENCE: 134
ggcnuucacc gcgugccuua                                                     20

<210> SEQ ID NO 135
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (5)..(5)
<223> OTHER INFORMATION: n is a, c, g, or u

<400> SEQUENCE: 135
ggcanucacc gcgugccuua                                                     20

<210> SEQ ID NO 136
```

```
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: n is a, c, g, or u

<400> SEQUENCE: 136
ggcauncacc gcgugccuua                                                  20

<210> SEQ ID NO 137
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (7)..(7)
<223> OTHER INFORMATION: n is a, c, g, or u

<400> SEQUENCE: 137
ggcauunacc gcgugccuua                                                  20

<210> SEQ ID NO 138
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (8)..(8)
<223> OTHER INFORMATION: n is a, c, g, or u

<400> SEQUENCE: 138
ggcauucncc gcgugccuua                                                  20

<210> SEQ ID NO 139
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (9)..(9)
<223> OTHER INFORMATION: n is a, c, g, or u

<400> SEQUENCE: 139
ggcauucanc gcgugccuua                                                  20

<210> SEQ ID NO 140
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (10)..(10)
<223> OTHER INFORMATION: n is a, c, g, or u

<400> SEQUENCE: 140
ggcauucacn gcgugccuua                                                  20
```

```
<210> SEQ ID NO 141
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (11)..(11)
<223> OTHER INFORMATION: n is a, c, g, or u

<400> SEQUENCE: 141
ggcauucacc ncgugccuua                                               20

<210> SEQ ID NO 142
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (12)..(12)
<223> OTHER INFORMATION: n is a, c, g, or u

<400> SEQUENCE: 142
ggcauucacc gngugccuua                                               20

<210> SEQ ID NO 143
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (13)..(13)
<223> OTHER INFORMATION: n is a, c, g, or u

<400> SEQUENCE: 143
ggcauucacc gcnugccuua                                               20

<210> SEQ ID NO 144
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (14)..(14)
<223> OTHER INFORMATION: n is a, c, g, or u

<400> SEQUENCE: 144
ggcauucacc gcgngccuua                                               20

<210> SEQ ID NO 145
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (15)..(15)
<223> OTHER INFORMATION: n is a, c, g, or u

<400> SEQUENCE: 145
ggcauucacc gcgunccuua                                               20
```

<210> SEQ ID NO 146
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (16)..(16)
<223> OTHER INFORMATION: n is a, c, g, or u

<400> SEQUENCE: 146
ggcauucacc gcgugncuua                                              20

<210> SEQ ID NO 147
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (17)..(17)
<223> OTHER INFORMATION: n is a, c, g, or u

<400> SEQUENCE: 147
ggcauucacc gcgugcnuua                                              20

<210> SEQ ID NO 148
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (18)..(18)
<223> OTHER INFORMATION: n is a, c, g, or u

<400> SEQUENCE: 148
ggcauucacc gcgugccnua                                              20

<210> SEQ ID NO 149
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (19)..(19)
<223> OTHER INFORMATION: n is a, c, g, or u

<400> SEQUENCE: 149
ggcauucacc gcgugccuna                                              20

<210> SEQ ID NO 150
<211> LENGTH: 20
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (20)..(20)
<223> OTHER INFORMATION: n is a, c, g, or u

<400> SEQUENCE: 150
ggcauucacc gcgugccuun                                              20

<210> SEQ ID NO 151
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or u

<400> SEQUENCE: 151
nggcauucac cgcgugccuu a                                              21

<210> SEQ ID NO 152
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (2)..(2)
<223> OTHER INFORMATION: n is a, c, g, or u

<400> SEQUENCE: 152
gngcauucac cgcgugccuu a                                              21

<210> SEQ ID NO 153
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is a, c, g, or u

<400> SEQUENCE: 153
ggncauucac cgcgugccuu a                                              21

<210> SEQ ID NO 154
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (4)..(4)
<223> OTHER INFORMATION: n is a, c, g, or u

<400> SEQUENCE: 154
ggcnauucac cgcgugccuu a                                              21

<210> SEQ ID NO 155
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (5)..(5)
<223> OTHER INFORMATION: n is a, c, g, or u

<400> SEQUENCE: 155
ggcanuucac cgcgugccuu a                                              21

<210> SEQ ID NO 156
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: n is a, c, g, or u

<400> SEQUENCE: 156
ggcaunucac cgcgugccuu a                                              21

<210> SEQ ID NO 157
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (7)..(7)
<223> OTHER INFORMATION: n is a, c, g, or u

<400> SEQUENCE: 157
ggcauuncac cgcgugccuu a                                              21

<210> SEQ ID NO 158
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (8)..(8)
<223> OTHER INFORMATION: n is a, c, g, or u

<400> SEQUENCE: 158
ggcauucnac cgcgugccuu a                                              21

<210> SEQ ID NO 159
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (9)..(9)
<223> OTHER INFORMATION: n is a, c, g, or u

<400> SEQUENCE: 159
ggcauucanc cgcgugccuu a                                              21

<210> SEQ ID NO 160
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (10)..(10)
<223> OTHER INFORMATION: n is a, c, g, or u

<400> SEQUENCE: 160

```
ggcauucacn cgcgugccuu a                                              21

<210> SEQ ID NO 161
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (11)..(11)
<223> OTHER INFORMATION: n is a, c, g, or u

<400> SEQUENCE: 161
ggcauucacc ngcgugccuu a                                              21

<210> SEQ ID NO 162
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (12)..(12)
<223> OTHER INFORMATION: n is a, c, g, or u

<400> SEQUENCE: 162
ggcauucacc gncgugccuu a                                              21

<210> SEQ ID NO 163
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (13)..(13)
<223> OTHER INFORMATION: n is a, c, g, or u

<400> SEQUENCE: 163
ggcauucacc gcngugccuu a                                              21

<210> SEQ ID NO 164
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (14)..(14)
<223> OTHER INFORMATION: n is a, c, g, or u

<400> SEQUENCE: 164
ggcauucacc gcgnugccuu a                                              21

<210> SEQ ID NO 165
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (15)..(15)
<223> OTHER INFORMATION: n is a, c, g, or u
```

```
<400> SEQUENCE: 165
ggcauucacc gcgungccuu a                                              21

<210> SEQ ID NO 166
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (16)..(16)
<223> OTHER INFORMATION: n is a, c, g, or u

<400> SEQUENCE: 166
ggcauucacc gcgugnccuu a                                              21

<210> SEQ ID NO 167
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (17)..(17)
<223> OTHER INFORMATION: n is a, c, g, or u

<400> SEQUENCE: 167
ggcauucacc gcgugcncuu a                                              21

<210> SEQ ID NO 168
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (18)..(18)
<223> OTHER INFORMATION: n is a, c, g, or u

<400> SEQUENCE: 168
ggcauucacc gcgugccnuu a                                              21

<210> SEQ ID NO 169
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (19)..(19)
<223> OTHER INFORMATION: n is a, c, g, or u

<400> SEQUENCE: 169
ggcauucacc gcgugccunu a                                              21

<210> SEQ ID NO 170
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (20)..(20)
<223> OTHER INFORMATION: n is a, c, g, or u
```

```
<400> SEQUENCE: 170
ggcauucacc gcgugccuun a                                              21

<210> SEQ ID NO 171
<211> LENGTH: 21
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (21)..(21)
<223> OTHER INFORMATION: n is a, c, g, or u

<400> SEQUENCE: 171
ggcauucacc gcgugccuua n                                              21

<210> SEQ ID NO 172
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or u

<400> SEQUENCE: 172
nggcauucac cgcgugccuu aa                                             22

<210> SEQ ID NO 173
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (2)..(2)
<223> OTHER INFORMATION: n is a, c, g, or u

<400> SEQUENCE: 173
ungcauucac cgcgugccuu aa                                             22

<210> SEQ ID NO 174
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is a, c, g, or u

<400> SEQUENCE: 174
ugncauucac cgcgugccuu aa                                             22

<210> SEQ ID NO 175
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (4)..(4)
```

```
<223> OTHER INFORMATION: n is a, c, g, or u

<400> SEQUENCE: 175
uggnauucac cgcgugccuu aa                                              22

<210> SEQ ID NO 176
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (5)..(5)
<223> OTHER INFORMATION: n is a, c, g, or u

<400> SEQUENCE: 176
uggcnuucac cgcgugccuu aa                                              22

<210> SEQ ID NO 177
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: n is a, c, g, or u

<400> SEQUENCE: 177
uggcanucac cgcgugccuu aa                                              22

<210> SEQ ID NO 178
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (7)..(7)
<223> OTHER INFORMATION: n is a, c, g, or u

<400> SEQUENCE: 178
uggcauncac cgcgugccuu aa                                              22

<210> SEQ ID NO 179
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (8)..(8)
<223> OTHER INFORMATION: n is a, c, g, or u

<400> SEQUENCE: 179
uggcauunac cgcgugccuu aa                                              22

<210> SEQ ID NO 180
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
```

```
<222> LOCATION: (9)..(9)
<223> OTHER INFORMATION: n is a, c, g, or u

<400> SEQUENCE: 180
uggcauucnc cgcgugccuu aa                                              22

<210> SEQ ID NO 181
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (10)..(10)
<223> OTHER INFORMATION: n is a, c, g, or u

<400> SEQUENCE: 181
uggcauucan cgcgugccuu aa                                              22

<210> SEQ ID NO 182
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (11)..(11)
<223> OTHER INFORMATION: n is a, c, g, or u

<400> SEQUENCE: 182
uggcauucac ngcgugccuu aa                                              22

<210> SEQ ID NO 183
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (12)..(12)
<223> OTHER INFORMATION: n is a, c, g, or u

<400> SEQUENCE: 183
uggcauucac cncgugccuu aa                                              22

<210> SEQ ID NO 184
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (13)..(13)
<223> OTHER INFORMATION: n is a, c, g, or u

<400> SEQUENCE: 184
uggcauucac cgngugccuu aa                                              22

<210> SEQ ID NO 185
<211> LENGTH: 22
<212> TYPE: RNA
<213> ORGANISM: Artificial Sequence
<220> FEATURE:
<223> OTHER INFORMATION: Synthetic primer
<220> FEATURE:
```

-continued

<221> NAME/KEY: misc_feature
<222> LOCATION: (14)..(14)
<223> OTHER INFORMATION: n is a, c, g, or u

<400> SEQUENCE: 185
uggcauucac cgcnugccuu aa                                              22

<210> SEQ ID NO 186
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (15)..(15)
<223> OTHER INFORMATION: n is a, c, g, or u

<400> SEQUENCE: 186
uggcauucac cgcgngccuu aa                                              22

<210> SEQ ID NO 187
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (16)..(16)
<223> OTHER INFORMATION: n is a, c, g, or u

<400> SEQUENCE: 187
uggcauucac cgcgunccuu aa                                              22

<210> SEQ ID NO 188
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (17)..(17)
<223> OTHER INFORMATION: n is a, c, g, or u

<400> SEQUENCE: 188
uggcauucac cgcgugncuu aa                                              22

<210> SEQ ID NO 189
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (18)..(18)
<223> OTHER INFORMATION: n is a, c, g, or u

<400> SEQUENCE: 189
uggcauucac cgcgugcnuu aa                                              22

<210> SEQ ID NO 190
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (19)..(19)
<223> OTHER INFORMATION: n is a, c, g, or u

<400> SEQUENCE: 190
uggcauucac cgcgugccnu aa                                    22

<210> SEQ ID NO 191
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (20)..(20)
<223> OTHER INFORMATION: n is a, c, g, or u

<400> SEQUENCE: 191
uggcauucac cgcgugccun aa                                    22

<210> SEQ ID NO 192
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (21)..(21)
<223> OTHER INFORMATION: n is a, c, g, or u

<400> SEQUENCE: 192
uggcauucac cgcgugccuu na                                    22

<210> SEQ ID NO 193
<211> LENGTH: 22
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (22)..(22)
<223> OTHER INFORMATION: n is a, c, g, or u

<400> SEQUENCE: 193
uggcauucac cgcgugccuu an                                    22

<210> SEQ ID NO 194
<211> LENGTH: 24
<212> TYPE: RNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (10)..(11)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u
<220> FEATURE:
<221> NAME/KEY: misc_feature
<222> LOCATION: (23)..(24)

```
<223> OTHER INFORMATION: n is a, c, g, or u

<400> SEQUENCE: 194
nggcagugun nuuaggugnu ugnn                                              24
```